(12) United States Patent
Lovat et al.

(10) Patent No.: US 12,275,780 B2
(45) Date of Patent: Apr. 15, 2025

(54) MONOCLONAL ANTIBODIES AGAINST AMBRA-1

(71) Applicant: AMLO Biosciences Limited, Newcastle Upon Tyne (GB)

(72) Inventors: Penny Lovat, Newcastle Upon Tyne (GB); Marie Labus, Newcastle Upon Tyne (GB); Rob Ellis, Newcastle Upon Tyne (GB); Ashleigh McConnell, Newcastle Upon Tyne (GB)

(73) Assignee: AMLO Biosciences Limited, Newcastle Upon Tyne (GB)

( * ) Notice: Subject to any disclaimer, the term of this patent is extended or adjusted under 35 U.S.C. 154(b) by 1007 days.

(21) Appl. No.: 17/309,218

(22) PCT Filed: Nov. 4, 2019

(86) PCT No.: PCT/GB2019/053120
§ 371 (c)(1),
(2) Date: May 7, 2021

(87) PCT Pub. No.: WO2020/099828
PCT Pub. Date: May 22, 2020

(65) Prior Publication Data
US 2021/0324059 A1 Oct. 21, 2021

(30) Foreign Application Priority Data

Nov. 15, 2018 (GB) ..................................... 1818618
Aug. 6, 2019 (GB) ..................................... 1911211

(51) Int. Cl.
*C07K 16/18* (2006.01)
*A61K 45/06* (2006.01)
*G01N 33/574* (2006.01)

(52) U.S. Cl.
CPC .............. *C07K 16/18* (2013.01); *A61K 45/06* (2013.01); *G01N 33/5743* (2013.01); *C07K 2317/33* (2013.01); *C07K 2317/565* (2013.01); *C07K 2317/567* (2013.01); *G01N 2333/4703* (2013.01); *G01N 2800/52* (2013.01)

(58) Field of Classification Search
CPC .............. C07K 16/18; C07K 2317/565; C07K 2317/567; G01N 33/5743; A61K 2039/505
USPC ........................................................ 436/512
See application file for complete search history.

(56) References Cited

U.S. PATENT DOCUMENTS 5,641,870 A 6/1997 Rinderknecht et al.

FOREIGN PATENT DOCUMENTS

| EP | 404097 | 6/1990 | | |
|---|---|---|---|---|
| WO | WO-9311161 A1 | 6/1993 | | |
| WO | WO-2009033743 A1 * | 3/2009 | .............. | C07K 16/18 |
| WO | WO-2016075440 | 5/2016 | | |
| WO | WO-2016075440 A1 * | 5/2016 | .............. | A61P 35/00 |
| WO | WO-2020099828 A1 | 5/2020 | | |

OTHER PUBLICATIONS

Capizzi et al., MIR7-3HG, a MYC-dependent modulator of cell proliferation, inhibits autophagy by a regulatory loop involving AMBRA1, (2017), Autophagy, 2017, vol. 13, No. 3, 554-566. (Year: 2017).*
"Ambra1 (G-6): sc-398204", Santa Cruz Biotechnology, Inc. [https://www.scbt.com/scbt/product/ambra1-antibody-g-6], (Aug. 24, 2019), 1 pg.
"International Application No. PCT/GB2019/053120, International Search Report and Written Opinion mailed Jan. 17, 2020", (Jan. 17, 2020), 15 pgs.
"United Kingdom Application GB1818618.9, Search Report dated May 1, 2019", (May 1, 2019), 4 pgs.
Bird, R. E., et al., "Single-chain antigen-binding proteins", Science, vol. 242, issue 4877 [abstract only], (Oct. 21, 1988), 423-426.
Chothia, Cyrus, et al., "Canonical Structures for the Hypervariable Regions of Immunoglobulins", J. Mol. Biol., 196, (1987), 901-917.
Huston, J. S., et al., "Protein engineering of antibody binding sites: recovery of specific activity in an anti-digoxin single-chain Fv analogue produced in *Escherichia coli*", PNAS, 85 (16) 5879-5883, (Aug. 1, 1988), 5879-5883.
Langedijk, Johannes P.M., et al., "Helical peptide arrays for lead identification and interaction site mapping", Analytical Biochemistry, vol. 417, Issue 1, (Oct. 1, 2011), 149-155.
McCarty, Kenneth S., et al., "Use of a Monoclonal Anti-Estrogen Receptor Antibody in the Immunohistochemical Evaluation of Human Tumors", Cancer Research (Suppl.), 46, 4244s-4248s, (Aug. 1986), 4244s-4248s.
Riker, Adam I., et al., "The gene expression profiles of primary and metastatic melanoma yields a transition point of tumor progression and metastasis", BMC Medical Genomics 2008, 1:13, (Apr. 28, 2008), 16 pgs.
Strappazzon, Flavie, et al., "Prosurvival Ambra1 turns into a propoptotic BH3-like protein during mitochondrial apoptosis", Autophagy, 12:6, 963-975, (Apr. 28, 2016), 963-975.
Tang, Diana Y.L., et al., "Prognostic impact of autophagy biomarkers for cutaneous melanoma", Frontiers in Oncology, vol. 6, Art. 236, (Nov. 9, 2016), 6 pgs.

(Continued)

*Primary Examiner* — Gregory S Emch
*Assistant Examiner* — Omar Ramadan
(74) *Attorney, Agent, or Firm* — Schwegman Lundberg & Woessner, P.A.

(57) ABSTRACT

The present invention relates inter alia to the development of monoclonal antibodies against Ambra-1 and methods for determining whether a subject with melanoma has an increased risk of metastasis using said antibodies.

16 Claims, 12 Drawing Sheets

Specification includes a Sequence Listing.

(56) References Cited

OTHER PUBLICATIONS

Timmerman, Peter, et al., "Functional reconstruction and synthetic mimicry of a conformational epitope using CLIPS technology", Journal of Molecular Recognition, vol. 20, issue 5 [abstract only], (Dec. 12, 2007), 283-299.

Verykiou, S., et al., "Peri-tumoural expression of pro-autophagic Ambra-1 as a prognostic biomarker for melanoma", Journal of Investigative Dermatology (2013), vol. 133, Supplement 1, p. S232, (May 1, 2013), S232.

Ward, E. Sally, et al., "Binding activities of a repertoire of single immunoglobulin variable domains secreted from *Escherichia coli*", Nature, 341 [abstract only], (Oct. 12, 1989), 544-546.

Zapata, Gerardo, et al., "Engineering linear F(ab*) fragments for efficient production in *Escherichia coli* and enhanced antiproliferative activity", Protein Eng. 8 (10) (abstract), (Oct. 1, 1995), 1057-1062.

Lim, Andrea, et al., "Defining the Functional Role of the Autophagy Regulatory Gene Ambra-1 in Melanoma invasion and Metastasis", Newcastle University, (2013), 1 pg.

Whitaker, S., et al., "Proautophagic Ambra-1 as biomarker of differentiation in cutaneous squamous carcinoma", British Society of Investigative Dermatology Annual Meeting; British Journal of Dermatology (2014) 170, pp. e6-e40 [abstract], (Apr. 15, 2014), 1 pg.

"International Application No. PCT GB2019 053120, International Preliminary Report on Patentability mailed May 27, 2021" 8 pgs.

* cited by examiner

MONOCLONAL ANTIBODIES AGAINST AMBRA-1

PRIORITY CLAIM TO RELATED APPLICATIONS

This application is a U.S. national stage filing under 35 U.S.C. § 371 from International Application No. PCT/GB2019/053120, filed on 4 Nov. 2019, and published as WO2020/099828 on 22 May 2020, which claims the benefit under 35 U.S.C. 119 to United Kingdom Application No. 1818618.9, filed on 15 Nov. 2018, and to United Kingdom Application No. 1911211.9, filed on 6 Aug. 2019, the benefit of priority of each of which is claimed herein, and which applications and publication are hereby incorporated herein by reference in their entirety.

FIELD OF THE INVENTION

The present invention relates inter alia to the development of monoclonal antibodies against Ambra-1 and methods for determining whether a subject with melanoma has an increased risk of metastasis using said antibodies.

BACKGROUND TO THE INVENTION

Following diagnosis with melanoma, patient prognosis is presently based on clinico-pathological criteria within the primary tumour. Although robust, AJCC staging criteria can only broadly categorise risk of disease progression based on epidemiological data from cohorts of other patients with similar staging in prior clinical reviews.

Currently, patients with thin melanomas are categorised as AJCC stage Ia/b and considered as being at a low risk of metastasis. However, 10% of AJCC Ia/b patients develop distant disease, and as such are mis-diagnosed based on current disease stratification. The ability to stratify this group of seemingly 'low-risk' patients more accurately would have a major impact on patient follow-up, the intensity of investigation, and the instigation of targeted adjuvant therapies in a trial or therapeutic setting.

Ambra-1 (activating molecule in Beclin-1 regulated autophagy protein 1) is a WD40-containing protein. Studies have implicated Ambra-1 in the control of autophagy and cellular differentiation. Immunohistochemical expression of epidermal Ambra-1 has also been identified as a biomarker for disease progression in melanoma (WO 2016/075440 A1). However, there remains a need to improve prognosis of metastasis in subjects suffering from melanoma. There also remains a need to improve treatment of patients suffering from melanoma and to decrease the likelihood of progression to metastasis.

It is an aim of some embodiments of the present invention to at least partially mitigate some of the problems identified in the prior art.

SUMMARY OF CERTAIN EMBODIMENTS OF THE INVENTION

Certain aspects of the present invention relate to the development of monoclonal antibodies against Ambra-1 and methods of using the same.

Antibodies described herein allow the improved detection of Ambra-1 as compared to known research grade polyclonal antibodies (Abcam Biochemicals, Cambridge, UK; 69501). In particular, the anti-Ambra-1 antibodies described herein have improved specificity to Ambra-1 as compared to research grade antibodies. Unexpectedly, these anti-Ambra-1 antibodies provide superior staining of epidermal keratinocytes in line with their differentiation status. The anti-Ambra-1 antibodies described herein also show superior specific staining of melanoma tumor cells as compared to the research grade antibodies.

The loss of Ambra-1 staining in the epidermal keratinocytes is associated with an increased risk of tumor spread. The loss of Ambra-1 is due to a loss of terminal differentiation of keratinocytes. The accurate assessment of Ambra-1 expression is important in determining metastatic risk. The superior specific staining of the antibodies described herein may allow more accurate assessment of loss of Ambra-1 expression as compared to research grade antibodies. For example, inaccurate detection using research grade antibodies against Ambra-1 may lead to the risk of a subject erroneously being determined as having an increased risk of metastasis. In such a scenario, the subject may undergo unnecessary psychological distress and/or medical procedures when in fact the subject is at a low risk of metastasis. Use of the antibodies described herein aims to mitigate such risks. Use of the antibodies described herein provides improved ease, accuracy and speed of determining Ambra-1 expression.

Due to the low purity of commercially available Ambra-1 and difficulty in producing this protein in mammalian expression systems, fully human, recombinant monoclonal antibodies were generated using a synthesized peptide sequence of the Ambra-1 epitope and Human Combinatorial Antibody Libraries (HUCAL, Bio-Rad). The epitope was conjugated to a larger carrier protein to raise the antibodies. Importantly, the antibodies described herein can be produced identically by sequence, securing consistent and reliable antibody production for clinical in vitro diagnostic use.

Further antibodies are also described herein that allow improved detection of loricrin as compared to known research grade polyclonal antibodies (Abcam Biochemicals, Cambridge, UK; 24722). Unexpectedly, these anti-loricrin antibodies show superior specific staining of uppermost terminally differentiated keratinocytes within the epidermis. In contrast, research grade polyclonal antibodies against loricrin stain several layers of differentiated keratinocytes. Thus, the anti-Loricrin antibodies described herein provide improved ease, accuracy and speed of determining Loricrin expression.

The more consistent and distinct pattern of expression of the anti-Ambra-1 (and optionally anti-Loricrin) antibodies described herein facilitates rapid and accurate identification of those subjects having decreased or loss of expression of Ambra-1 (and optionally Loricrin). In certain embodiments, the clear pattern of expression obtained using the antibodies described herein allows rapid and accurate identification of decreased or loss of expression of Ambra-1 (and optionally Loricrin) by visual assessment. Thus, certain aspects of the invention relate to improved methods for determining whether a subject with melanoma has an increased risk of metastasis. Accordingly, certain aspects of the present invention provide inter alia:

a method for determining whether a subject with melanoma has an increased risk of metastasis, the method comprising:
(i) determining the expression of Ambra-1 in a tissue sample obtained from the subject using a monoclonal antibody against Ambra-1 as described herein, wherein the tissue sample comprises tissue overlying a primary melanoma; and (ii) comparing the expression obtained in (i) with a reference tissue or levels obtained therefrom,
wherein a decrease in the expression of Ambra-1 in the tissue sample compared to the reference tissues or levels, or a loss of expression of Ambra-1 in the tissue sample, is indicative of an increased risk of metastasis;
use of antibodies against Ambra-1 as described herein for determining whether a subject with melanoma has an increased risk of metastasis;
an antibody that competes for binding to Ambra-1 with the antibodies as described herein;
an antibody that binds to the same epitope as the antibodies as described herein;
a method of labelling Ambra-1 in a tissue sample overlying a melanoma, the method comprising:
(a) contacting the tissue sample with a monoclonal antibody against Ambra-1 as described herein; and
(b) visualising the antibody in the tissue sample with a reagent that generates a detectable signal;
a method for determining a treatment regime for a subject suffering from melanoma, the method comprising:
(i) determining the expression of Ambra-1 in a tissue sample obtained from the subject using a monoclonal antibody against Ambra-1 as described herein, wherein the tissue sample comprises tissue overlying a primary melanoma; and
(ii) comparing the expression obtained in (i) with a reference tissue or levels obtained therefrom, and
(iii) (a) if expression of Ambra-1 is normal, following a normal recognized care pathway, or
(b) if expression of Ambra-1 is decreased or lost, treating the subject with a systemic anti-cancer treatment regime;
a method of treating a subject suffering from melanoma, the method comprising:
(i) determining the expression of Ambra-1 in a tissue sample obtained from the subject using a monoclonal antibody against Ambra-1 as described herein, wherein the tissue sample comprises tissue overlying a primary melanoma; and
(ii) comparing the expression obtained in (i) with a reference tissue or levels obtained therefrom, and
if there is a decrease in the expression of Ambra-1 in the tissue sample compared to the reference tissue or levels, or a loss of expression of Ambra-1, administering a therapeutic agent to the subject;
a method of treating a subject suffering from melanoma, the method comprising administering a therapeutic agent to the subject, wherein the subject has been identified as having decreased or a loss of expression of Ambra-1 as described herein;
an in vitro assay for predicting an increased risk of metastasis in a subject suffering from melanoma, the assay comprising:
contacting a tissue sample obtained from the subject with an antibody against Ambra-1 as described herein, wherein the tissue sample comprises tissue overlying a primary melanoma and the presence of Ambra-1 creates an Ambra-1-antibody complex; and
detecting and/or quantifying the Ambra-1-antibody complex; and
a kit for predicting an increased risk of developing metastasis of a subject suffering from melanoma, the kit comprising an antibody against Ambra-1 as described herein.

DETAILED DESCRIPTION OF CERTAIN EMBODIMENTS

Embodiments of the invention will now be described by way of example only, and with reference to the accompanying Figures in which.

Figure 11:
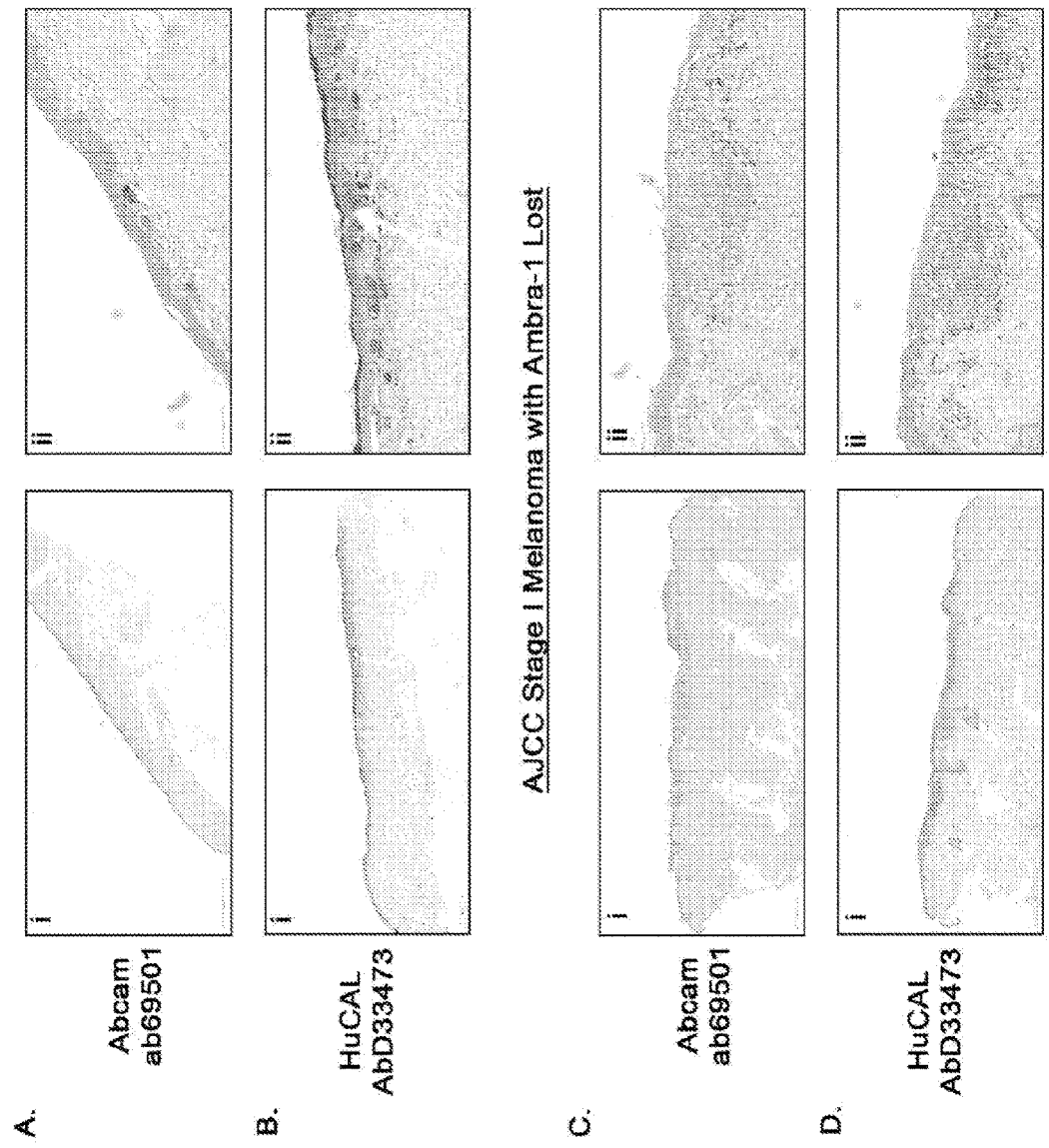

FIG. 11 shows expression of Ambra-1 in AJCC Stage I Melanoma. A) Photomicrograph of AJCC Stage I Melanoma with maintained Ambra-1, detected using Abcam antibody ab69501 (diluted 1/350), or B) HuCAL antibody AbD33473 (0.342 µg/ml) using DAB (brown) chromogen. C) Photomicrograph of AJCC Stage I Melanoma with Ambra-1 lost, detected using Abcam antibody ab69501 (diluted 1/350), or D) HuCAL antibody AbD33473 (0.342 µg/ml) using DAB (brown) chromogen. A,B,C,D i.) Magnification approximately 4× or ii.)×10.

Figure 12:
Figure 12:
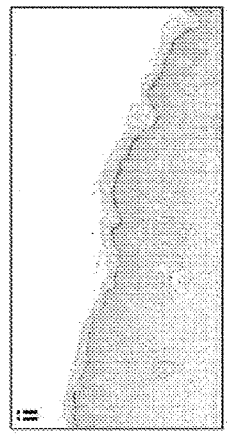
Figure 12:
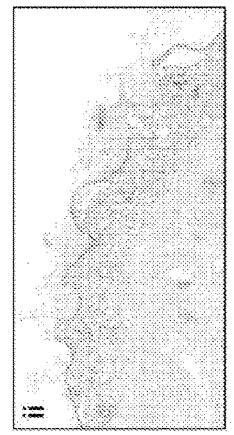
Figure 12:
Figure 12:
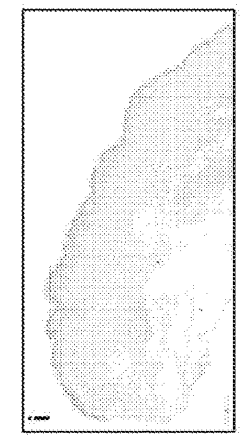
Figure 12:
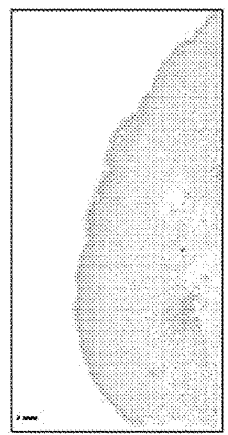
Figure 12:
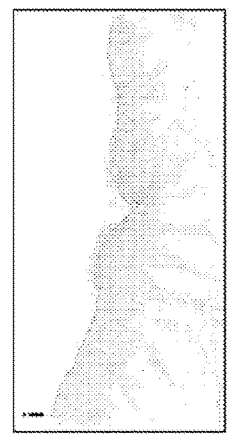
Figure 12:
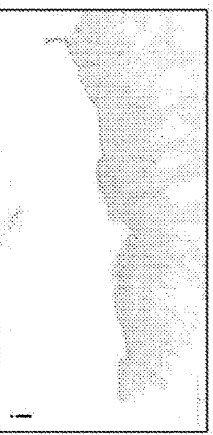

FIG. 12 shows expression of Loricrin in AJCC Stage I Melanoma. A) Photomicrograph of AJCC Stage I Melanoma with maintained Loricrin detected using Abcam antibody ab176322 (diluted 1/2000) using DAB (brown) chromogen, or B) HuCAL antibody AbD33047 (14 µg/ml) using fast red (red) chromogen. C) Photomicrograph of AJCC Stage I Melanoma with Loricrin lost, detected using Abcam antibody ab176322 (diluted 1/2000) using DAB (brown) chromogen, or D) HuCAL antibody AbD33047 (14 µg/ml) using fast red (red) chromogen. A,B,C,D i.) Magnification approximately 4× or ii.)×10.

Sequence listing
SEQ ID NO: 1 shows the amino acid sequence of HCDR1 of the anti-Ambra-1 antibody (SYWIH);

SEQ ID NO: 2 shows the amino acid sequence of HCDR2 of the anti-Ambra-1 antibody (TIFPSRSYTTYSPSFQG);

SEQ ID NO: 3 shows the amino acid sequence of HCDR3 of the anti-Ambra-1 antibody (DTPSTALKSPFDY);

SEQ ID NO: 4 shows the amino acid sequence of LCDR1 of the anti-Ambra-1 antibody (SGSSSNIGYNYVY);

SEQ ID NO: 5 shows the amino acid sequence of LCDR2 of the anti-Ambra-1 antibody (ENNKRPS);

SEQ ID NO: 6 shows the amino acid sequence of LCDR3 of the anti-Ambra-1 antibody (SSWDSHSNSYV);

SEQ ID NO: 7 shows the amino acid sequence of HCFR1 of the anti-Ambra-1 antibody (EVQLVQSGAEVKKPGESLKISCKGSGYSFS);

SEQ ID NO: 8 shows the amino acid sequence of HCFR2 of the anti-Ambra-1 antibody (WVRQMPGKGLEWMG);

SEQ ID NO: 9 shows the amino acid sequence of HCFR3 of the anti-Ambra-1 antibody (QVTISADKSISTAYLQWSSLKASDTAMYYCAR);

SEQ ID NO: 10 shows the amino acid sequence of HCFR4 of the anti-Ambra-1 antibody (WGQGTLVTVSS);

SEQ ID NO: 11 shows the amino acid sequence of LCFR1 of the anti-Ambra-1 antibody (DIVLTQPPSVSGAPGQRVTISC);

SEQ ID NO: 12 shows the amino acid sequence of LCFR2 of the anti-Ambra-1 antibody (WYQQLPGTAPKLLIY);

SEQ ID NO: 13 shows the amino acid sequence of LCFR3 of the anti-Ambra-1 antibody (GVPDRFSGSKSGTSASLAITGLQAEDEADYYC);

SEQ ID NO: 14 shows the amino acid sequence of LCFR4 of the anti-Ambra-1 antibody (FGGGTKLTVLGQ);

SEQ ID NO: 15 shows the amino acid sequence of the $V_H$ domain of the anti-Ambra-1 antibody;
EVQLVQSGAEVKKPGESLKISCKGSGYSFSSYWIHWVRQMPGKGLEWMGTIFPSRSYTTYSPSFQGQVTI

SADKSISTAYLQWSSLKASDTAMYYCARDTPSTALKSPFDYWGQGTLVTVSS

SEQ ID NO: 16 shows the amino acid sequence of the $V_L$ domain of the anti-Ambra-1 antibody;
DIVLTQPPSVSGAPGQRVTISCSGSSSNIGYNYVYWYQQLPGTAPKLLIYENNKRPSGVPDRFSGSKSGT

SASLAITGLQAEDEADYYCSSWDSHSNSYVFGGGTKLTVLGQ

SEQ ID NO: 17 shows the amino acid sequence of the Fd chain ($V_H$ domain and constant domain) of the Fab region of the anti-Ambra-1 antibody;
EVQLVQSGAEVKKPGESLKISCKGSGYSFSSYWIHWVRQMPGKGLEWMGTIFPSRSYTTYSPSFQGQVTISADKSIS

TAYLQWSSLKASDTAMYYCARDTPSTALKSPFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYICNVNHKPSNTKVDKKVEPKS

SEQ ID NO: 18 shows the amino acid sequence of the light chain ($V_L$ domain and constant domain) of the Fab region of the anti-Ambra-1 antibody;
DIVLTQPPSVSGAPGQRVTISCSGSSSNIGYNYVYWYQQLPGTAPKLLIYENNKRPSGVPDRFSGSKSGTSASLAIT

GLQAEDEADYYCSSWDSHSNSYVFGGGTKLTVLGQPKAAPSVTLFPPSSEELQANKATLVCLISDFYPGAVTVAWKA

DSSPVKAGVETTTPSKQSNNKYAASSYLSLTPEQWKSHRSYSCQVTHEGSTVEKTVAPTEA

SEQ ID NO: 19 shows the nucleic acid sequence encoding the Fd chain of the Fab region and tags (alkaline phosphatase dimerization domain sequence (AP), FLAG tag (DYKDDDDK) and His6 tag of the anti-Ambra-1 antibody;
GAAGTGCAATTGGTGCAGAGCGGTGCGGAAGTGAAAAAACCGGGCGAAAGCCTGAAAATTAGCTGCAAAGGCTCCGG

ATATAGCTTCTCTTCTTACTGGATCCATTGGGTGCGCCAGATGCCGGGCAAAGGTCTCGAGTGGATGGGCACTATCT

TCCCGTCTCGTAGCTACACCACTTATAGCCCGAGCTTTCAGGGCCAGGTGACCATTAGCGCGGATAAAAGCATCAGC

ACCGCGTATCTGCAATGGAGCAGCCTGAAAGCGAGCGATACCGCGATGTATTATTGCGCGCGTGACACTCCGTCTAC

TGCTCTGAAATCTCCGTTCGATTACTGGGGCCAAGGCACCCTGGTGACTGTTAGCTCAGCGTCGACCAAAGGCCCGA

-continued

```
GCGTGTTTCCGCTGGCCCCGAGCAGCAAAAGCACCAGCGGCGGCACCGCCGCACTGGGCTGCCTGGTGAAAGATTAT
TTCCCGGAACCAGTGACCGTGAGCTGGAACAGCGGTGCCCTGACCAGCGGCGTGCATACCTTTCCGGCGGTGCTGCA
AAGCAGCGGCCTGTATAGCCTGAGCAGCGTTGTGACCGTGCCGAGCAGCAGCCTGGGCACCCAGACCTATATTTGCA
ACGTCAACCATAAACCGAGCAACACCCAAAGTCGATAAAAAAGTCGAACCGAAAAGCGAATTCAAGGCTGAAATGCCT
GTTCTGGAAAACCGGGCTGCTCAGGGCGATATTACTACACCCGGCGGTGCTCGCCGTTTAACGGGTGATCAGACTGC
CGCTCTGCGTGATTCTCTTAGCGATAAACCTGCAAAAAATATTATTTTGCTGATTGGCGATGGGATGGGGGACTCGG
AAATTACTGCCGCACGTAATTATGCCGAAGGTGCGGGCGGCTTTTTTAAAGGTATAGATGCCTTACCGCTTACCGGG
CAATACACTCACTATGCGCTGAATAGAAAAACCGGCAAACCGGACTACGTCACCAGCTCGGCTGCATCAGCAACCGC
CTGGTCAACCGGTGTCAAAACCTATAACGGCGCGCTGGGCGTCGATATTCACGAAAAAGATCACCCAACGATTCTGG
AAATGGCAAAAGCCGCAGGTCTGGCGACCGGTAACGTTTCTACCGCAGAGTTGCAGGATGCCACGCCCGCTGCGCTG
GTGGCACATGTGACCTCGCGCAAATGCTACGGTCCGAGCGCGACCAGTGAAAAATGTCCGGGTAACGCTCTGGAAAA
AGGCGGAAAAGGATCGATTACCGAACAGCTGCTTAACGCTCGTGCCGACGTTACGCTTGGCGGCGGCGCAAAAACCT
TTGCTGAAACGGCAACCGCTGGTGAATGGCAGGGAAAAACGCTGCGTGAACAGGCACAGGCGCGTGGTTATCAGTTG
GTGAGCGATGCTGCCTCACTGAACTCGGTGACGGAAGCGAATCAGCAAAAACCCCTGCTTGGCCTGTTTGCTGACGG
CAATATGCCAGTGCGCTGGCTAGGACCGAAAGCAACGTACCATGGCAATATCGATAAGCCCGCAGTCACCTGTACGC
CAAATCCGCAACGTAATGACAGTGTACCAACCCTGGCGCAGATGACCGACAAAGCCATTGAATTGTTGAGTAAAAAT
GAGAAAGGCTTTTTCCTGCAAGTTGAAGGTGCGTCAATCGATAAACAGGATCATGCTGCGAATCCTTGTGGGCAAAT
TGGCGAGACGGTCGATCTCGATGAAGCCGTACAACGGGCGCTGGAGTTCGCTAAAAAGGAGGGTAACACGCTGGTCA
TAGTCACCGCTGATCACGCCCACGCCAGCCAGATTGTTGCGCCGGATACCAAAGCTCCGGGCCTCACCCAGGCGCTA
AATACCAAAGATGGCGCAGTGATGGTGATGAGTTACGGGAACTCCGAAGAGGATTCACAAGAACATACCGGCAGTCA
GTTGCGTATTGCGGCGTATGGCCCGCATGCCGCCAATGTTGTTGGACTGACCGACCAGACCGATCTCTTCTACACCA
TGAAAGCCGCTCTGGGGCTGAAAGGCGCGCCGGACTATAAAGATGACGATGACAAAGGCGCGCCGCACCATCATCAC
CATCAC
```

SEQ ID NO: 20 shows the nucleic acid sequence encoding the light chain of the Fab region of the anti-Ambra-1 antibody;

```
GATATCGTGCTGACCCAGCCGCCGAGCGTGAGCGGTGCACCGGGCCAGCGCGTGACCATTAGCTGTAGCGGCAGCAG
CAGCAACATTGGTTACAACTACGTGTACTGGTACCAGCAGCTGCCGGGCACGGCGCCGAAACTGCTGATCTACGAAA
ACAACAAACGCCCCGAGCGGCGTGCCGGATCGCTTTAGCGGATCCAAAAGCGGCACCAGCGCCAGCCTGGCGATTACC
GGCCTGCAAGCAGAAGACGAAGCGGATTATTACTGCTCTTCTTGGGACTCTCATTCTAACTCTTACGTGTTTGGCGG
CGGCACGAAGTTAACCGTTCTTGGCCAGCCGAAAGCCGCCCCAAGCGTGACCCTGTTTCCGCCGAGCAGCGAAGAAC
TGCAAGCCAACAAAGCCACCCTGGTTTGCCTGATCAGCGATTTTTATCCGGGTGCCGTGACCGTGGCCTGGAAAGCC
GATAGCAGCCCGGTGAAAGCCGGCGTGGAAACCACCACCCCGAGCAAACAGAGCAACAACAAATATGCCGCCAGCAG
CTATCTGAGCCTGACCCCGGAACAGTGGAAAAGCCATCGCAGCTATAGTTGTCAAGTGACCCATGAAGGCAGCACCG
TGGAAAAAACCGTGGCCCCGACCGAGGCC
```

SEQ ID NO: 21 shows the amino acid sequence of human Ambra-1;

```
MKVVPEKNAVRILWGRERGARAMGAQRLLQELVEDKTRWMKWEGKRVELPDSPRSTFLLAFSPDRTLLASTHVNHNI
YITEVKTGKCVHSLIGHRRTPWCVTFHPTISGLIASGCLDGEVRIWDLHGGSESWFTDSNNAIASLAFHPTAQLLLI
ATANEIHFWDWSRREPFAVVKTASEMERVRLVRFDPLGHYLLTAIVNPSNQQGDDEPEIPIDGTELSHYRQRALLQS
QPVRRTPLLHNFLHMLSSRSSGIQVGEQSTVQDSATPSPPPPPPQPSTERPRTSAYIRLRQRVSYPTAECCQHLGIL
CLCSRCSGTRVPSLLPHQDSVPPASARATTPSFSFVQTEPFHPPEQASSTQQDQGLLNRPSAFSTVQSSTAGNTLRN
LSLGPTRRSLGGPLSSHPSRYHREIAPGLTGSEWTRTVLSLNSRSEAESMPPPRTSASSVSLLSVLRQQEGGSQASV
YTSATEGRGFPASGLATESDGGNGSSQNNSGSIRHELQCDLRRFFLEYDRLQELDQSLSGEAPQTQQAQEMLNNNIE
```

-continued

SERPGPSHQPTPHSSENNSNLSRGHLNRCRACHNLLTFNNDTLRWERTTPNYSSGEASSSWQVPSSFESVPSSGSQL

PPLERTEGQTPSSSRLELSSSASPQEERTVGVAFNQETGHWERIYTQSSRSGTVSQEALHQDMPEESSEEDSLRRRL

LESSLISLSRYDGAGSREHPIYPDPARLSPAAYYAQRMIQYLSRRDSIRQRSMRYQQNRLRSSTSSSSSDNQGPSVE

GTDLEFEDFEDNGDRSRHRAPRNARMSAPSLGREVPRRELLPEYLPYAGIFHERGQPGLATHSSVNRVLAGAVIGDG

QSAVASNIANTTYRLQWWDETKEDLPEISNASVNVLVQNCKIYNDASCDISADGQLLAAFIPSSQRGFPDEGILAVY

SLAPHNLGEMLYTKRFGPNAISVSLSPMGRYVMVGLASRRILLHPSTEHMVAQVERLQQAHGGETSMRRVENVLYPM

PADQRRHVSINSARWLPEPGLGLAYGTNKGDLVICRPEALNSGVEYYWDQLNETVFTVHSNSRSSERPGTSRATWRT

DRDMGLMNAIGLQPRNPATSVTSQGTQTLALQLQNAETQEREVPEPGTAASGPGEGEGSEYGASGEDALSRIQRLM

AEGGMTAVVQREQSTTMASMGGFGNNIIVSHRIHRSSQTGTEPGAAHTSSPQPSTSRGLLPEAGQLAERGLSPRTAS

WDQPGTPGREPTQPTLPSSSPVPIPVSLPSAEGPTLHCELTNNNHLLDGGSSRGDAAGPRGEPRNR

SEQ ID NO: 22 shows the amino acid sequence of HCDR1 of the anti-Loricrin antibody (DYYIH);

SEQ ID NO: 23 shows the amino acid sequence of HCDR2 of the anti-Loricrin antibody (VISPNSGKTNYAQKFQG);

SEQ ID NO: 24 shows the amino acid sequence of HCDR3 of the anti-Loricrin antibody (DLYPDSSAFDI);

SEQ ID NO: 25 shows the amino acid sequence of LCDR1 of the anti-Loricrin antibody (SGDNLGDKYAH);

SEQ ID NO: 26 shows the amino acid sequence of LCDR2 of the anti-Loricrin antibody (DDNERPS);

SEQ ID NO: 27 shows the amino acid sequence of LCDR3 of the anti-Loricrin antibody (QSYDSGNRV);

SEQ ID NO: 28 shows the amino acid sequence of HCFR1 of the anti-Loricrin antibody (QVQLVQSGAEVKKPGASVKVSCKASGYTFN);

SEQ ID NO: 29 shows the amino acid sequence of HCFR2 of the anti-Loricrin antibody (WVRQAPGQGLEWMG);

SEQ ID NO: 30 shows the amino acid sequence of HCFR3 of the anti-Loricrin antibody (RVTMTRDTSISTAYMELSRLRSEDTAVYYCAR);

SEQ ID NO: 31 shows the amino acid sequence of HCFR4 of the anti-Loricrin antibody (WGQGTLVTVSS);

SEQ ID NO: 32 shows the amino acid sequence of LCFR1 of the anti-Loricrin antibody (DIELTQPPSVSVSPGQTASITC);

SEQ ID NO: 33 shows the amino acid sequence of LCFR2 of the anti-Loricrin antibody (WYQQKPGQAPVLVIY);

SEQ ID NO: 34 shows the amino acid sequence of LCFR3 of the anti-Loricrin antibody (GIPERFSGSNSGNTATLTISGTQAEDEADYYC);

SEQ ID NO: 35 shows the amino acid sequence of LCFR4 of the anti-Loricrin antibody (FGGGTKLTVLGQ);

SEQ ID NO: 36 shows the amino acid sequence of the $V_H$ domain of the anti-Loricrin antibody;
QVQLVQSGAEVKKPGASVKVSCKASGYTFNDYYIHWVRQAPGQGLEWMGVISPNSGKTNYAQKFQGRVTM

TRDTSISTAYMELSRLRSEDTAVYYCARDLYPDSSAFDIWGQGTLVTVSS

SEQ ID NO: 37 shows the amino acid sequence of the $V_L$ domain of the anti-Loricrin antibody;
DIELTQPPSVSVSPGQTASITCSGDNLGDKYAHWYQQKPGQAPVLVIYDDNERPSGIPERFSGSNSGNTATLTISGT

QAEDEADYYCQSYDSGNRVFGGGTKLTVLGQ

SEQ ID NO: 38 shows the amino acid sequence of the Fd chain ($V_H$ domain and constant domain) of the Fab region of the anti-Loricrin antibody;
QVQLVQSGAEVKKPGASVKVSCKASGYTFNDYYIHWVRQAPGQGLEWMGVISPNSGKTNYAQKFQGRVTMTRDTSIS

TAYMELSRLRSEDTAVYYCARDLYPDSSAFDIWGQGTLVTVSSASTKGPSVFPLAPSSKSTSGGTAALGCLVKDYFP

EPVTVSWNSGALTSGVHTFPAVLQSSGLYSLSSVVTVPSSSLGTQTYICNVNHKPSNTKVDKKVEPKS

SEQ ID NO: 39 shows the amino acid sequence of the light chain (V_L domain and constant domain) of the Fab region of the anti-Loricrin antibody;
DIELTQPPSVSVSPGQTASITCSGDNLGDKYAHWYQQKPGQAPVLVIYDDNERPSGIPERFSGSNSGNTATLTISGT

QAEDEADYYCQSYDSGNRVFGGGTKLTVLGQPKAAPSVTLFPPSSEELQANKATLVCLISDFYPGAVTVAWKADSSP

VKAGVETTTPSKQSNNKYAASSYLSLTPEQWKSHRSYSCQVTHEGSTVEKTVAPTEA

SEQ ID NO: 40 shows the nucleic acid sequence encoding the Fd chain of the Fab region and tags (alkaline phosphatase dimerization domain sequence (AP), FLAG tag (DYKDDDDK) and His6 tag (HHHHHH)) of the anti-Loricrin antibody;
CAGGTGCAATTGGTGCAGAGCGGTGCGGAAGTGAAAAAACCGGGTGCCAGCGTGAAAGTTAGCTGCAAAGCGTCCGG

ATATACCTTCAACGACTACTACATCCATTGGGTGCGCCAGGCCCCGGGCCAGGGCCTCGAGTGGATGGGCGTTATCT

CTCCGAACTCTGGCAAAACGAACTACGCGCAGAAATTTCAGGGCCGGGTGACCATGACCCGTGATACCAGCATTAGC

ACCGCGTATATGGAACTGAGCCGTCTGCGTAGCGAAGATACGGCCGTGTATTATTGCGCGCGTGACCTGTACCCGGA

CTCTTCTGCTTTCGATATCTGGGGCCAAGGCACCCTGGTGACTGTTAGCTCAGCGTCGACCAAAGGCCCGAGCGTGT

TTCCGCTGGCCCCGAGCAGCAAAAGCACCAGCGGCGGCACCGCCGCACTGGGCTGCCTGGTGAAAGATTATTTCCCG

GAACCAGTGACCGTGAGCTGGAACAGCGGTGCCCTGACCAGCGGCGTGCATACCTTTCCGGCGGTGCTGCAAAGCAG

CGGCCTGTATAGCCTGAGCAGCGTTGTGACCGTGCCGAGCAGCAGCCTGGGCACCCAGACCTATATTTGCAACGTCA

ACCATAAACCGAGCAACACCAAAGTCGATAAAAAAGTCGAACCGAAAAGCGAATTCAAGGCTGAAATGCCTGTTCTG

GAAAACCGGGCTGCTCAGGGCGATATTACTACACCCGGCGGTGCTCGCCGTTTAACGGGTGATCAGACTGCCGCTCT

GCGTGATTCTCTTAGCGATAAACCTGCAAAAAATATTATTTTGCTGATTGGCGATGGGATGGGGGACTCGGAAATTA

CTGCCGCACGTAATTATGCCGAAGGTGCGGGCGGCTTTTTTAAAGGTATAGATGCCTTACCGCTTACCGGGCAATAC

ACTCACTATGCGCTGAATAGAAAAACCGGCAAACCGGACTACGTCACCAGCTCGGCTGCATCAGCAACCGCCTGGTC

AACCGGTGTCAAAACCTATAACGGCGCGCTGGGCGTCGATATTCACGAAAAAGATCACCCAACGATTCTGGAAATGG

CAAAAGCCGCAGGTCTGGCGACCGGTAACGTTTCTACCGCAGAGTTGCAGGATGCCACGCCCGCTGCGCTGGTGGCA

CATGTGACCTCGCGCAAATGCTACGGTCCGAGCGCGACCAGTGAAAAATGTCCGGGTAACGCTCTGGAAAAAGGCGG

AAAAGGATCGATTACCGAACAGCTGCTTAACGCTCGTGCCGACGTTACGCTTGGCGGCGGCGCAAAAACCTTTGCTG

AAACGGCAACCGCTGGTGAATGGCAGGGAAAAACGCTGCGTGAACAGGCACAGGCGCGTGGTTATCAGTTGGTGAGC

GATGCTGCCTCACTGAACTCGGTGACGGAAGCGAATCAGCAAAAACCCCTGCTTGGCCTGTTTGCTGACGGCAATAT

GCCAGTGCGCTGGCTAGGACCGAAAGCAACGTACCATGGCAATATCGATAAGCCCGCAGTCACCTGTACGCCAAATC

CGCAACGTAATGACAGTGTACCAACCCTGGCGCAGATGACCGACAAAGCCATTGAATTGTTGAGTAAAAATGAGAAA

GGCTTTTTCCTGCAAGTTGAAGGTGCGTCAATCGATAAACAGGATCATGCTGCGAATCCTTGTGGGCAAATTGGCGA

GACGGTCGATCTCGATGAAGCCGTACAACGGGCGCTGGAGTTCGCTAAAAAGGAGGGTAACACGCTGGTCATAGTCA

CCGCTGATCACGCCCACGCCAGCCAGATTGTTGCGCCGGATACCAAAGCTCCGGGCCTCACCCAGGCGCTAAATACC

AAAGATGGCGCAGTGATGGTGATGAGTTACGGGAACTCCGAAGAGGATTCACAAGAACATACCGGCAGTCAGTTGCG

TATTGCGGCGTATGGCCCGCATGCCGCCAATGTTGTTGGACTGACCGACCAGACCGATCTCTTCTACACCATGAAAG

CCGCTCTGGGGCTGAAAGGCGCGCCGGACTATAAAGATGACGATGACAAAGGCGCGCCGCACCATCATCACCATCAC

SEQ ID NO: 41 shows the nucleic acid sequence encoding the light chain of the Fab region of the anti-Loricrin antibody;
GATATCGAACTGACCCAGCCGCCGAGCGTGAGCGTGAGCCCGGGCCAGACCGCGAGCATTACCTGTAGCG

GCGATAACCTGGGTGACAAATACGCTCATTGGTACCAGCAGAAACCGGGCCAGGCGCCGGTGCTGGTGAT

CTACGACGACAACGAACGTCCGAGCGGCATCCCGGAACGTTTTAGCGGATCCAACAGCGGCAACACCGCG

ACCCTGACCATTAGCGGCACCCAGGCGGAAGACGAAGCGGATTATTACTGCCAGTCTTACGACTCTGGTA

ACCGTGTGTTTGGCGGCGGCACGAAGTTAACCGTTCTTGGCCAGCCGAAAGCCGCCCCAAGCGTGACCCT

GTTTCCGCCGAGCAGCGAAGAACTGCAAGCCAACAAAGCCACCCTGGTTTGCCTGATCAGCGATTTTTAT

CCGGGTGCCGTGACCGTGGCCTGGAAAGCCGATAGCAGCCCGGTGAAAGCCGGCGTGGAAACCACCACCC

-continued

CGAGCAAACAGAGCAACAACAAATATGCCGCCAGCAGCTATCTGAGCCTGACCCCGGAACAGTGGAAAAG

CCATCGCAGCTATAGTTGTCAAGTGACCCATGAAGGCAGCACCGTGGAAAAAACCGTGGCCCCGACCGAG

GCC

SEQ ID NO: 42 shows the amino acid sequence of human Loricrin;
MSYQKKQPTPQPPVDCVKTSGGGGGGGSGGGGCGFFGGGGSGGGSSGSGCGYSGGGGYSGGGCGGGSSGGGGGGGI

GGCGGGSGGSVKYSGGGGSSGGGSGCFSSGGGGSGCFSSGGGGSSGGGSGCFSSGGGGSSGGGSGCFSSGGGGFSGQ

AVQCQSYGGVSSGGSSGGGSGCFSSGGGGGSVCGYSGGGSGCGGGSSGGSGSGYVSSQQVTQTSCAPQPSYGGGSSG

GGGSGGGSGCFSSGGGGGSSGCGGGSSGIGSGCIISGGGSVCGGGSSGGGGGGSSVGGSGSGKGVPICHQTQQKQAPT

WPSK

SEQ ID NO: 43 shows the amino acid sequence of an exemplary epitope tag
(DYKDDDDK)

SEQ ID NO: 44 shows the amino acid sequence of an exemplary epitope tag
(GKPIPNPLLGLDST)

SEQ ID NO: 45 shows the amino acid sequence of an exemplary epitope tag
(WSHPQFEK)

SEQ ID NO: 46 shows the amino acid sequence of the peptide to which anti-Ambra-1 antibodies
were raised
(CGGSSRGDAAGPRGEPRNR)

SEQ ID NO: 47 shows the amino acid sequence of the His6 tag
(HHHHHH)

SEQ ID NO: 48 shows the Ambra-1 C-terminal sequence used for replacement analysis in
epitope mapping
(VSLPSAEGPTLHCELTNNNHLLDGGSSRGDAAGPRGEPRNR)

SEQ ID NO: 49 shows the REPNET epitope of the Anti-Ambra-1 antibodies
(DGGSSRGDAAGPRGEPRNR)

SEQ ID NO: 50 shows the LIN epitope of the Anti-Ambra-1 antibodies
(HLLDGGSSR)

SEQ ID NO: 51 shows the LOOP epitope of the Anti-Ambra-1 antibodies
(NHLLDGGSSR)

SEQ ID NO: 52 shows a core epitope of the Anti-Ambra-1 antibodies
(EPRN)

SEQ ID NO: 53 shows a core epitope of the Anti-Ambra-1 antibodies
(EPR)

SEQ ID NO: 54 shows an epitope of the Anti-Loricrin antibodies
(SYQKKQPTPGPPVDCVKTS)

SEQ ID NO: 55 shows an epitope of the Anti-Loricrin antibodies
(GGGGIGGPGGGSGGSVKYS)

SEQ ID NO: 56 shows an epitope of the Anti-Loricrin antibodies
(GSSGGGSGCFSSGGG)

SEQ ID NO: 57 shows an epitope of the Anti-Loricrin antibodies
(GIGSGCIISGGGSVCGGGS)

SEQ ID NO: 58 shows an epitope of the Anti-Loricrin antibodies
(GSSGGGGGGSSVGGSGSGK)

SEQ ID NO: 59 shows an epitope of the Anti-Loricrin antibodies
(GVCICHQTQQK)

SEQ ID NO: 60 shows a core epitope of the Anti-Loricrin antibodies
(VKYS)

SEQ ID NO: 61 shows a core epitope of the Anti-Loricrin antibodies
(CFS)

The practice of embodiments of the present invention employs, unless otherwise indicated, conventional techniques of chemistry, molecular biology, pharmaceutical formulation, pharmacology and medicine, which are within the skill of those working in the art.

Most general chemistry techniques can be found in Comprehensive Heterocyclic Chemistry IF (Katritzky et al., 1996, published by Pergamon Press); Comprehensive Organic Functional Group Transformations (Katritzky et al., 1995, published by Pergamon Press); Comprehensive Organic Synthesis (Trost et al. 1991, published by Pergamon); Heterocyclic Chemistry (Joule et al. published by Chapman & Hall); Protective Groups in Organic Synthesis (Greene et al., 1999, published by Wiley-Interscience); and Protecting Groups (Kocienski et al., 1994).

Most general molecular biology techniques can be found in Sambrook et al, Molecular Cloning, A Laboratory Manual (2001) Cold Harbor-Laboratory Press, Cold Spring Harbor, N.Y. or Ausubel et al., Current Protocols in Molecular Biology (1990) published by John Wiley and Sons, N.Y.

Most general pharmaceutical formulation techniques can be found in Pharmaceutical Preformulation and Formulation ($2^{nd}$ Edition edited by Mark Gibson) and Pharmaceutical Excipients: Properties, Functionality and Applications in Research and Industry (edited by Otilia M Y Koo, published by Wiley).

Most general pharmacological techniques can be found in A Textbook of Clinical Pharmacology and Therapeutics ($5^{th}$ Edition published by Arnold Hodder).

Most general techniques on the prescribing, dispensing and administering of medicines can be found in the British National Formulary 72 (published jointly by BMJ Publishing Group Ltd and Royal Pharmaceutical Society).

Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, $2^{nd}$ ed., 2002, CRC Press; The Dictionary of Cell and Molecular Biology, $3^{rd}$ ed., Academic Press; and the Oxford University Press, provide a person skilled in the art with a general dictionary of many of the terms used in this disclosure. For chemical terms, the skilled person may refer to the International Union of Pure and Applied Chemistry (IUPAC).

Units, prefixes and symbols are denoted in their Système International d'Unités (SI) accepted form. Numeric ranges are inclusive of the numbers defining the range.

Methods for Determining Risk of Progression to Metastatic Melanoma

The invention provides a method for determining whether a subject with melanoma has an increased risk of metastasis. Typically, the method is in vitro. The subject may be a human or an animal suffering from melanoma. In some embodiments, the subject is a horse, cat or dog. Typically, the subject is a human. In some embodiments, the subject has already been diagnosed as having melanoma.

As used herein, the term "metastasis" refers to the recurrence or disease progression that may occur locally (such as local recurrence and in transit disease), regionally (such as nodal micro-metastasis or macro-metastasis), or distally (such as brain, lung and other tissues). In some embodiments, the term "metastasis" is used to refer to metastatic disease following a primary melanoma. Typically, metastasis originating from a primary melanoma may spread to the lungs and/or brain of the subject as well as other locations.

The stage of a melanoma is a description of how widespread it is. This includes its thickness in the skin, whether it has spread to nearby lymph nodes or any other organs, and certain other factors. The stage is based on the results of the physical exam, biopsies, and any imaging tests (CT or MRI scan, etc.) or other tests that have been done. Such tests will be known to those skilled in the art. The system most often used to stage melanoma is the American Joint Commission on Cancer (AJCC) TNM system. The table below describes the features identifying each stage.

| | Stage 1 |
|---|---|
| 1a Tumour | <1.00 mm without ulceration; no lymph node involvement, no distant metastases. |
| 1b Tumour | <1.00 mm with ulceration or Clark level IV or V tumour 1.01-2.0 mm without ulceration; no lymph node involvement; no distant metastases. |
| | Stage 2 |
| 2a Tumour | 1.0-2.0 mm with ulceration; tumour 2.01-4.0 mm without ulceration; no lymph node involvement; no distant metastases. |
| 2b Tumour | 2.01-4 mm with ulceration. |
| 2b Tumour | >4.0 mm without ulceration; no lymph node involvement; no distant metastases. |
| 2c Tumour | >4.0 mm with ulceration; no nodal involvement; no distant metastases. |
| | Stage 3 |
| 3a | Tumour of any thickness without ulceration with 1 positive lymph node and micro-metastasis or macro-metastasis. |
| 3b | Tumour of any thickness without ulceration with 2-3 positive lymph nodes and micro-metastasis or macro-metastasis. |
| 3c | Tumour of any thickness and macro-metastasis OR in-transit met(s)/satellite(s) without metastatic lymph nodes, OR 4 or more metastatic lymph nodes, matted nodes or combinations of in-transit met(s)/satellite(s), OR ulcerated melanoma and metastatic lymph node(s). |
| | Stage 4 |
| 4 | Tumour of any thickness with any nodes and any metastases |

In some embodiments, the subject is suffering from AJCC stage 1, stage 2, stage 3 or stage melanoma. In some embodiments, the subject is suffering from AJCC stage 1a, stage 1 b, stage 2a, stage 2b or stage 2c melanoma. In some embodiments, the subject is suffering from AJCC stage 1a or stage 1b melanoma. In some embodiments, the methods further comprise staging a primary tumour present in a tissue sample obtained from a subject in accordance with AJCC staging. In some embodiments the patient has ulcerated melanoma.

The method for determining whether a subject with melanoma has an increased risk of metastasis comprises determining the expression of Ambra-1 in a tissue sample obtained from the subject.

The tissue sample comprises tissue overlying a primary melanoma. As used herein, the term "primary melanoma" refers to a malignant tumour on the skin at the site of origin, regardless of thickness, in patients without clinical or histologic evidence of regional or distant metastatic disease. The wording "tissue overlying a primary melanoma", refers to epidermal tissue situated between a primary melanoma and the surface of the skin.

In some embodiments, the tissue sample comprises at least a portion of the peri-tumoral epidermis overlying the primary melanoma. In some embodiments, the tissue sample further comprises a portion of normal tissue adjacent to the primary melanoma. The term "normal tissue" includes, for example, "normal epidermis" which is healthy (i.e. disease-free). In some embodiments, the normal tissue is epidermis that lies adjacent to the primary melanoma, for example, within a cuff of normal skin taken with the primary melanoma sample. The term "peri-tumoral epidermis" refers to epidermal tissue overlying or situated around a tumor.

In some embodiments, the method comprises determining the expression levels of Ambra-1 in the epidermis. Keratinocytes are cells which constitute about 90% of the epidermis. Thus, in some embodiments, the tissue sample comprises keratinocytes overlying the primary melanoma. Typically, the subject may be identified as being at increased risk of metastasis, wherein said identification comprises determining that the subject has a decrease or loss of expression of Ambra-1 in keratinocytes overlying the primary melanoma of the subject.

In some embodiments, the tissue sample has previously been obtained from the subject such that the sampling itself does not form a part of the methods of the invention. The sample may have been obtained immediately prior to the method, or hours, days or weeks prior to the method. In other embodiments, a method of the invention may additionally comprise the step of obtaining the tissue sample from the subject.

The expression of Ambra-1 is determined using a monoclonal antibody against Ambra-1 as described herein. Typically, the expression of Ambra-1 is determined by contacting the tissue with the antibody and detecting the presence of the bound antibody. For example, presence of the bound antibody may be detected by visualising the antibody in the tissue sample with a reagent that generates a detectable signal (e.g. a detection moiety as described herein).

In some embodiments, the method comprises contacting the tissue with the antibody under conditions permissive for binding of the anti-Ambra-1 antibody to Ambra-1 and detecting whether a complex is formed between the anti-Ambra-1 antibody and Ambra-1. Such methods may be in vitro or in vivo methods. Typically, the presence of the bound antibody is detected by immunoassays such as immunohistochemistry (IHC), immunofluorescence (IF), immunoblotting, flow cytometry (e.g., FACS™) or enzyme-linked immunosorbent assay (ELISA).

The method for determining whether a subject with melanoma has an increased risk of metastasis further comprises comparing the expression of Ambra-1 determined for the tissue sample obtained from the subject with a reference tissue or levels obtained therefrom.

In some embodiments, the reference comprises levels of Ambra-1 expression that are characteristic of normal tissue. Typically, reference levels of Ambra-1 may be obtained by determining the expression of Ambra-1 in a reference tissue. In some embodiments, the expression levels of Ambra-1 in a reference tissue are determined by visual or automated assessment. In some embodiments, reference levels of Ambra-1 expression that are characteristic of normal tissue are obtained by determining expression levels in tissue samples obtained from one or more (e.g. a cohort) of healthy subjects.

In some embodiments, the reference tissue comprises normal tissue. In some embodiments, the normal tissue comprises epidermis from a site which does not include a primary melanoma. In some embodiments, the reference tissue (or levels obtained therefrom) is an internal reference (i.e. obtained from the subject). In some embodiments, the reference tissue is normal tissue obtained from a site adjacent to the primary melanoma. In other embodiments, the reference tissue is obtained from a site of the subject which is remote from the primary melanoma. Thus, in some embodiments, the reference level is the level of expression of Ambra-1 in normal tissue. The reference tissue may be taken from normal epidermis and the reference level is a level of expression in the keratinocytes of the normal epidermis. The expression of Ambra-1 in the reference tissue, for example, to generate reference levels, can be determined using the methods described herein.

Advantageously, the anti-Ambra-1 antibodies described herein consistently stain tumour cells. Thus, the reference tissue may also comprise the tumour cells below the epidermis. Detection of Ambra-1 in tumour cells adjacent to the epidermis (where Ambra-1 expression may be decreased or lost) may act as a positive control in the methods described herein.

Typically, the tissue sample may be a biopsy, or a section thereof, obtained from the subject. A tissue sample, such as a biopsy, can be obtained through a variety of sampling methods known to those skilled in the art, including a punch biopsy, shave biopsy, wide local excision and other means. Aptly, the tumour sample is taken from a surgical site from which the primary melanoma has been excised from a subject.

Typically, the tissue sample may be frozen, fresh, fixed (e.g. formalin fixed), centrifuged, and/or embedded (e.g. paraffin embedded), etc. The tissue sample may be or have been subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the Ambra-1 in the sample. Likewise, biopsies may also be subjected to post-collection preparative and storage techniques, e.g., fixation. A tissue sample, or a section thereof, may be mounted on a solid support, such as a slide.

In the method for determining whether a subject with melanoma has an increased risk of metastasis, a decrease in the expression of Ambra-1 in the tissue sample compared to the reference tissue or levels, or a loss of expression of Ambra-1 in the tissue sample, is indicative of an increased risk of metastasis.

For example, a decrease or loss in the expression of Ambra-1 may be a level of expression of Ambra-1 less than about 75% of the respective reference level.

In some embodiments, a decrease in expression of Ambra-1 is a level of expression of Ambra-1 from about 25% to about 75% of the respective reference level. In some embodiments, a loss of expression of Ambra-1 is a level of expression of Ambra-1 less than about 25% of the reference level of the relevant protein. Normal expression is understood to mean that the expression of Ambra-1 is greater than about 75% of the reference level. Thus, in some embodiments, the expression level of Ambra-1 in the tissue sample is from about 25% to about 75% of the reference level. In some embodiments, the expression level of Ambra-1 is no greater than 75%, no greater than 70%, no greater than 60%, no greater than 50%, no greater than 40% or no greater than 30% of the reference level. In some embodiments, there is substantially no expression of Ambra-1 in the tissue sample. In certain embodiments, the expression of Ambra-1 is less than 25%.

The term "comparing" and "compare" may refer to a comparison of corresponding parameters or levels, e.g., an absolute amount is compared to an absolute reference amount while a concentration is compared to a reference concentration or a signal intensity signal obtained from the tissue sample is compared to the same type of signal intensity obtained from the reference. The comparison may be carried out manually, for example by visual assessment, or it may be automated (e.g. using an automated scanner or computer-assisted). Thus, the comparison may be carried out by a computing device.

In certain embodiments, the expression of Ambra-1 is scored on the basis of the intensity and/or proportion of positive cells in the tissue sample. Scoring methods have been described and are well known to one of ordinary skill in the art.

In one embodiment, an intensity score may be defined as follows: 0=no appreciable staining in the cells, 1=faint/barely perceptible partial staining in the cytoplasm and/or nucleus of the cells, 2=weak to moderate staining of the cytoplasm and/or nucleus of the cells, and 3=strong staining of the cytoplasm and/or nucleus of the cells. A proportion score may be defined as follows: 0=less than 5%, 1=from 5% to 25%, 2=from 26% to 50%, 3=from 51% to 75%, and 4=more than 75%. A total score may be calculated by multiplying the intensity score and the proportion score, producing a total range of 0 to 12. In certain embodiments, scores of 0 to 3 may be indicative of decrease or loss of expression. In certain embodiments, scores of 4 to 12 may be indicative of an increase in expression.

In another embodiment, a H-score may be calculated (McCarty et al., Cancer Res. 1986 46(8 Supl):4244s-4248s). An intensity score may be defined as follows:

| | |
|---|---|
| 1 = | faint/barely perceptible partial (e.g. weak) staining in the cells |
| 2 = | moderate staining of the cells; |
| 3 = | strong staining of the cells. |

The H score combines components of staining intensity with the percentage of positive cells. It has a value between 0 and 300 and is defined as:

1*(percentage of cells staining at 1+ intensity);
+2*(percentage of cells staining at 2+ intensity);
+3*(percentage of cells staining at 3+ intensity);
=H score.

A H-score of about 100, 110, 120, 130, 140, 150 or above may indicate increased expression of Ambra-1. Conversely, a H-score of less than about 150, 140, 130, 120, 110 or 100 may indicate decreased expression of Ambra-1.

In certain embodiments, "weak", "moderate" or "strong" staining of the cells is relative to levels of Ambra-1 characteristic of the reference or normal tissue.

In certain embodiments, the method of comparing the expression of Ambra-1 comprises outputting, optionally on a computer, (i) an indication of the expression levels of Ambra-1 and (ii) this indicates whether the subject has an increased risk of metastasis.

In certain embodiments, an increased risk of metastasis means a 7-year metastasis-free (also known as "disease-free") survival rate of less than 50%, for example less than 40%, for example less than 30%, for example less than 20%, for example less than 10%, for example less than 5%.

The methods described herein allow subjects with melanoma to be stratified into those more likely to develop metastasis and those less likely to develop metastasis. Advantageously, the methods of the invention help to identify which subjects with melanoma are most likely to benefit from treatment with a therapeutic agent. Typically, methods of the invention enable treatment with a therapeutic agent for a subject who would otherwise not have been eligible for treatment with a therapeutic agent.

Antibodies Against Ambra-1

Antibodies against Ambra-1 are used to determine the expression of Ambra-1 in a tissue sample obtained from the subject.

Antibodies against Ambra-1 include any monoclonal antibodies, including chimeric antibodies, humanized antibodies, bi-specific antibodies and domains and fragments of monoclonal antibodies including Fab, Fab', F(ab')2, scFv, dsFv, ds-scFv, dimers, minibodies, diabodies, and multimers thereof. Monoclonal antibodies can be fragmented using conventional techniques. Monoclonal antibodies may be from any animal origin, including birds and mammals (e.g., human, murine, donkey, sheep, rabbit, goat, guinea pig, camel, horse, or chicken), transgenic animals, or from recombinant sources. Typically, the monoclonal antibodies against Ambra-1 are fully human. Monoclonal antibodies may be prepared using any methods known to those skilled in the art, including by recombination. Aptly, the antibodies of the invention exclude polyclonal antibodies such as research-grade antibodies.

Typically, the antibody against Ambra-1 is isolated. An "isolated" antibody is an antibody that has been identified and separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In certain embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain.

In certain embodiments, the antibody against Ambra-1 is a fragment that specifically binds Ambra-1. An "antibody fragment" is a portion of an intact antibody that includes an antigen binding site of the intact antibody and thus retaining the ability to bind Ambra-1. Antibody fragments include:

(i) Fab fragments, having $V_L$, $C_L$, $V_H$ and CH1 domains;
(ii) Fab' fragments, which is a Fab fragment having one or more cysteine residues at the C-terminus of the CH1 domain;

(iii) Fd fragments having V$_H$ and CH1 domains;
(iv) Fd' fragments having V$_H$ and CH1 domains and one or more cysteine residues at the C-terminus of the CH1 domain;
(v) Fv fragments having the V$_L$ and V$_H$ domains of a single arm of an antibody;
(vi) dAb fragments (Ward et al., Nature 341, 544-546 (1989)) which consist of a VH domain;
(vii) isolated CDR regions, including any one or more of SEQ ID Nos 1 to 6;
(viii) F(ab')2 fragments, a bivalent fragment including two Fab' fragments linked by a disulphide bridge at the hinge region;
(ix) single chain antibody molecules (e.g. single chain Fv; scFv) (Bird et al, Science 242:423-426 (1988); and Huston et al., PNAS (USA) 85:5879-5883 (1988));
(x) "diabodies" with two antigen binding sites, comprising a heavy chain variable domain (VH) connected to a light chain variable domain (VL) in the same polypeptide chain (see, e.g., EP 404,097 and WO 93/11161;
(xi) "linear antibodies" comprising a pair of tandem Fd segments (VH-CH1-VH-CH1) which, together with complementary light chain polypeptides, form a pair of antigen binding regions (Zapata et al. Protein Eng. 8 (10): 1057-1062 (1995); and U.S. Pat. No. 5,641,870).

Typically, the antibody against Ambra-1 is a recombinant monoclonal antibody. A "recombinant monoclonal antibody" is an antibody or antibody fragment produced using recombinant antibody coding genes. In certain embodiments, the antibodies of the invention are generated from a human combinatorial antibody library (e.g. HuCAL, Bio-Rad).

Typically, the antibody against Ambra-1 is a monovalent Fab or bivalent Fab fragment. A "bivalent Fab fragment" may be considered as equivalent to a F(ab')2 fragment and formed via dimerization. For example, a bivalent Fab fragment is formed via dimerization of a synthetic double helix loop helix motif (dHLX) or a bacterial alkaline phosphatase (AP) domain. In certain embodiments, the antibody against Ambra-1 comprises a dimerization domain sequence and one or more linker sequences.

In certain embodiments, the antibody against Ambra-1 is a recombinant monoclonal antibody fragment converted into an immunoglobulin (Ig) format. For example, when an Fc region is required, the variable heavy and light chain genes may be cloned into vectors with the desired constant regions and co-transfected for expression in mammalian cells using methods known to those skilled in the art. In certain embodiments, antibody fragments are converted to human IgA, IgE, IgG1, IgG2, IgG3 or IgM.

In certain embodiments, the antibody against Ambra-1 is labelled with at least one epitope tag. Typical epitope tags include His6, Flag (e.g. DYKDDDDK), V5 (e.g. GKPIPN-PLLGLDST), Strep (e.g. WSHPQFEK) and/or any combination thereof. Typically, the antibody against Ambra-1 is a monovalent Fab or bivalent Fab fragment with one or more (e.g. two) epitopes.

In certain embodiments, the antibody against Ambra-1 is conjugated to an enzyme and/or fluorescent label.

In certain embodiments, the antibody specifically binds to Ambra-1. In other words, the antibodies against Ambra-1 bind Ambra-1 with a binding dissociation equilibrium constant (K$_D$) of less than about 30 nM, less than about 20 nM, less than about 10 nm, less than about 1 nm or less than about 200 μm. The skilled person would understand techniques for measuring binding strengths (e.g. koff-rate determination; 'secondary screening') include, for example, Bio-Layer Interferometry (e.g. using the Pall ForteBio Octet® System).

In certain embodiments, the antibody against Ambra-1 comprises the following heavy chain variable domain complementarity determining regions (CDRs):
(a) HCDR1 comprising the amino acid sequence of SEQ ID NO: 1;
(b) HCDR2 comprising the amino acid sequence of SEQ ID NO: 2; and
(c) HCDR3 comprising the amino acid sequence of SEQ ID NO: 3.

In certain embodiments, the antibody against Ambra-1 further comprises the following light chain variable domain CDRs:
(d) LCDR1 comprising the amino acid sequence of SEQ ID NO: 4
(e) LCDR2 comprising the amino acid sequence of SEQ ID NO: 5; and
(f) LCDR3 comprising the amino acid sequence of SEQ ID NO: 6.

As used herein, the term "Complementarity Determining Regions" (CDRs) refers to the amino acid residues of an antibody variable domain the presence of which are necessary for antigen binding. Each variable domain typically has three CDR regions identified as CDR1, CDR2 and CDR3. Each complementarity determining region may comprise amino acid residues from a "complementarity determining region" as defined by Kabat (i.e. about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, MD (1991)) and/or those residues from a "hypervariable loop" (i.e. about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a CDR region can include amino acids from both a CDR region defined according to Kabat and a hypervariable loop.

Unless otherwise specified herein, numbering of amino acid residues in the Fc region or constant region is according to the EU numbering system, also called the EU index, as described in Kabat et al.

In certain embodiments, the antibody against Ambra-1 further comprises the following heavy chain variable domain framework regions (FRs):
(a) HCFR1 comprising the amino acid sequence of SEQ ID NO: 7;
(b) HCFR2 comprising the amino acid sequence of SEQ ID NO: 8;
(c) HCFR3 comprising the amino acid sequence of SEQ ID NO: 9; and
(d) HCFR4 comprising the amino acid sequence of SEQ ID NO: 10.

In certain embodiments, the antibody against Ambra-1 further comprises the following light chain variable domain FRs:
(e) LCFR1 comprising the amino acid sequence of SEQ ID NO: 11;
(f) LCFR2 comprising the amino acid sequence of SEQ ID NO: 12;

(g) LCFR3 comprising the amino acid sequence of SEQ ID NO: 13; and (h) LCFR4 comprising the amino acid sequence of SEQ ID NO: 14.

As used herein, "Framework regions (FRs)" are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues.

If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

In certain embodiments, the antibody against Ambra-1 further comprises an antibody variable domain comprising:

(a) a $V_H$ sequence having at least 90%, at least 95%, at least 96%, at least 97%, at least 98%, at least 99% or more sequence identity to the amino acid sequence of SEQ ID NO: 15;

(b) a $V_L$ sequence having at least 90%, at least 95%, at least 96%, at least 97%, at least 98%, at least 99% or more sequence identity to the amino acid sequence of SEQ ID NO 16; or (c) a $V_H$ sequence as in (a) and a $V_L$ sequence as in (b).

In certain embodiments, the antibody against Ambra-1 comprises:

(d) a $V_H$ sequence comprising SEQ ID NO: 15;

(e) a $V_L$ sequence comprising SEQ ID NO: 16; or (f) a $V_H$ sequence as in (d) and a $V_L$ sequence as in (e).

As used herein, "antibody variable domain" refers to the portions of the light and heavy chains of antibody molecules that include amino acid sequences of the CDRs (i.e., CDR1, CDR2, and CDR3) and the FRs (i.e., FR1, FR2, FR3 and FR4). $V_H$ refers to the variable domain of the heavy chain. $V_L$ refers to the variable domain of the light chain.

As used herein, "sequence identity" refers to a sequence having the specified percentage of amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid sequences. Suitable programs to determine percent sequence identity include for example the BLAST suite of programs available from the U.S. Government's National Center for Biotechnology Information BLAST web site. Comparisons between two sequences can be carried using either the BLASTN or BLASTP algorithm. BLASTN is used to compare nucleic acid sequences, while BLASTP is used to compare amino acid sequences. ALIGN, ALIGN-2 (Genentech, South San Francisco, California) or MegAlign, available from DNASTAR, are additional publicly available software programs that can be used to align sequences. One skilled in the art can determine appropriate parameters for maximal alignment by alignment software. In certain embodiments, the default parameters of the alignment software are used.

In certain embodiments, the antibody against Ambra-1 comprises a Fab fragment comprising the Fd chain of SEQ ID NO:17; and/or the light chain of SEQ ID NO:18. Typically, such antibodies further comprise one or more dimerization domain sequences, one or more linker sequences and/or one or more epitope tags as described herein.

The invention provides use of antibodies against Ambra-1 as described herein. Typically, the antibodies against Ambra-1 are used in the methods described herein of determining whether a subject with melanoma has an increased risk of metastasis.

The invention also provides antibodies that compete for binding to Ambra-1 with antibodies as described herein. Typically, competition assays are used to identify an antibody that competes for binding to Ambra-1. In an exemplary competition assay, immobilized Ambra-1 is incubated in a solution comprising a first labelled antibody that binds to Ambra-1 and a second unlabelled antibody that is being tested for its ability to compete with the first antibody for binding to Ambra-1. The second antibody may be present in a hybridoma supernatant. As a control, immobilized Ambra-1 may be incubated in a solution comprising the first labelled antibody but not the second unlabelled antibody. After incubation under conditions permissive for binding of the first antibody to Ambra-1 excess unbound antibody may be removed, and the amount of label associated with immobilized Ambra-1 measured. If the amount of label associated with immobilized Ambra-1 is substantially reduced in the test sample relative to the control sample, then that indicates that the second antibody is competing with the first antibody for binding to Ambra-1. See, e.g., Harlow et al. Antibodies: A Laboratory Manual. Ch.14 (Cold Spring Harbor Laboratory, Cold Spring Harbor, NY, 1988).

In certain embodiments, antibodies that compete for binding to Ambra-1 bind to the same epitope (e.g., a linear or a conformational epitope) as the antibodies described herein. Detailed exemplary methods for mapping an epitope to which an antibody binds are provided in Morris "*Epitope Mapping Protocols,*" in Methods in Molecular Biology Vol. 66 (Humana Press, Totowa, NJ, 1996).

Certain aspects of the present invention further provide isolated nucleic acids that encode any of the antibodies described herein. Also provided is a vector (e.g., an expression vector) comprising the nucleic acid for expressing any of the antibodies described herein. Also provided are host cells comprising the preceding nucleic acids and/or vectors.

Certain aspects of the present invention further provide immunoconjugates comprising any of the antibodies described herein conjugated to one or more capture agents. As described herein, a capture agent typically comprises a binding and/or detection moiety (e.g. an enzyme and/or fluorescent label).

Certain aspects of the present invention further provide antibodies that bind to the same epitope as the anti-Ambra-1 antibody as defined herein. In certain embodiments, the invention provides antibodies that bind specifically to peptides near the carboxyl-terminus of human Ambra-1.

As used herein, the term "epitope" means a protein determinant capable of specific binding to an antibody. Typically, an epitope comprises chemically active surface groupings of molecules such as amino acids or sugar side chains usually having specific three-dimensional structural and charge characteristics. The epitope may comprise amino acid residues directly involved in the binding and optionally additional amino acid residues that are not directly involved in the binding.

As used herein, an antibody that "specifically" binds to an epitope refers to an antibody that recognizes the epitope while only having little or no detectable reactivity with other portions of Ambra-1. Such relative specificity can be determined e.g. by competition assays, foot-printing techniques or mass spectrometry techniques as known in the art.

In certain embodiments, the epitope comprises peptide antigenic determinants within single peptide chains of Ambra-1. In certain embodiments, the epitope comprises conformational antigenic determinants comprising one or more contiguous amino acids on a particular chain and/or on spatially contiguous but separate peptide chains. In certain embodiments, the epitope comprises post-translational antigenic determinants comprising molecular structures (e.g. carbohydrate groups) covalently attached to Ambra-1.

The epitope may comprise any suitable number and/or type of amino acids, in any suitable position as defined herein. For example, the epitope may comprise about 3 to about 10 amino acids, typically about 3 to about 8 amino acids, in or more contiguous or non-contiguous locations with respect to the amino acid sequence of Ambra-1 as set forth in SEQ ID NO: 21, 46, or 48.

In certain embodiments, the invention provides antibodies that bind to Ambra-1, wherein said antibodies specifically bind to a region comprising 8, 9, 10, 11, 12, 13, 14, 15, 16, 17, 18, 19, 20 or more of the amino acids 1270 to 1298 of human Ambra-1 sequence shown in SEQ ID NO: 21. Typically, such antibodies specifically bind to a region comprising amino acids 1280 to 1281 of SEQ ID NO: 21, amino acids 1294 to 1296 of SEQ ID NO: 21 and/or amino acids 1294 to 1297 of SEQ ID NO: 21.

In certain embodiments, the invention provides antibodies that bind to Ambra-1, wherein said antibodies specifically bind to a region comprising 8, 9, 10, 11, 12, 13, 14, 15 or more of CGGSSRGDAAGPRGEPRNR (SEQ ID NO: 46). Typically, such antibodies specifically bind to a region comprising at least EPRN (SEQ ID NO: 52) or at least EPR (SEQ ID NO: 53) of Ambra-1.

In certain embodiments, the invention provides antibodies that bind to Ambra-1, wherein said antibodies specifically bind to a region comprising 8, 9, 10, 11, 12, 13, 14, 15 or more of DGGSSRGDAAGPRGEPRNR (SEQ ID NO: 49). Typically, such antibodies specifically bind to a region comprising at least DG, EPRN (SEQ ID NO: 52) and/or EPR (SEQ ID NO: 53) of Ambra-1.

In certain embodiments, the invention provides antibodies that bind to Ambra-1, wherein said antibodies specifically bind to a region comprising HLLDGGSSR (SEQ ID NO: 50) and/or EPR (SEQ ID NO: 53) of Ambra-1.

In certain embodiments, the invention provides antibodies that bind to Ambra-1, wherein said antibodies specifically bind to a region comprising NHLLDGGSSR (SEQ ID NO: 51) and/or EPR (SEQ ID NO: 53) of Ambra-1.

In certain embodiments, the invention provides antibodies that specifically bind to Ambra-1, wherein said antibody specifically binds to:
  (i) amino acids 1280-1281 and/or 1294-1296 of human Ambra-1 (SEQ ID NO:21);
  (ii) amino acids 1277-1285 and/or 1294-1296 of human Ambra-1 (SEQ ID NO:21);
  (iii) amino acids 1276-1285 and/or 1294-1296 of human Ambra-1 (SEQ ID NO:21);
  (iii) amino acids 1280-1296 of human Ambra-1 (SEQ ID NO:21);
  (iv) amino acids 1276-1296 of human Ambra-1 (SEQ ID NO: 21)
  (v) amino acids 1280-1298 of human Ambra-1 (SEQ ID NO:21); and/or
  (vi) amino acids 1276-1298 of human Ambra-1 (SEQ ID NO:21).

In certain embodiments, the invention provides a method of labelling Ambra-1 in a tissue sample overlying a primary melanoma, the method comprising:
  (a) contacting the tissue sample with a monoclonal antibody against Ambra-1 as defined herein; and
  (b) visualising the antibody in the tissue sample with a reagent that generates a detectable signal.

The tissue sample may comprise at least a portion of a peri-tumoral epidermis overlying the primary melanoma. Typically, the tissue sample comprises keratinocytes overlying the primary melanoma. Typically, the method comprises determining the expression of Ambra-1 in the keratinocytes. Typically, the tissue sample is a biopsy, or a section thereof, obtained from a subject suffering from melanoma.

Antibodies Against Loricrin

In certain embodiments, the methods for determining whether a subject with melanoma has an increased risk of metastasis further comprises determining the expression level of Loricrin in the tissue sample. Typically, the expression level of Loricrin is determined using an antibody, e.g. a monoclonal antibody.

Antibodies against Loricrin include any antibodies as described above, including e.g. recombinant monoclonal antibodies.

In certain embodiments, the antibody against Loricrin is isolated.

In certain embodiments, the antibody against Loricrin is a fragment that specifically binds Loricrin.

In certain embodiments, the antibody against Loricrin is labelled with at least one epitope tag as described above. Typically, the antibody against Loricrin is a monovalent Fab or bivalent Fab fragment with one or more (e.g. two) epitopes as described above.

In certain embodiments, the antibody against Loricrin is conjugated to an enzyme and/or fluorescent label as described above.

In certain embodiments, the antibody specifically binds to Loricrin. In other words, the antibodies against Loricrin bind Loricrin with a binding dissociation equilibrium constant ($K_D$) of less than about 30 nM, less than about 20 nM, less than about 10 nm, less than about 1 nm or less than about 200 μm. The skilled person would understand techniques for measuring binding strengths include, for example, Bio-Layer Interferometry (e.g. using the Pall ForteBio Octet® System).

In certain embodiments, the method for determining whether a subject with melanoma has an increased risk of metastasis further comprises:
  (iii) determining the expression level of Loricrin in the tissue sample using a monoclonal antibody against Loricrin; and
  (iv) comparing the expression level obtained in (iii) with a reference tissue or levels obtained therefrom,
  wherein a decrease in the expression of Ambra-1 and Loricrin in the tissue sample compared to the reference tissue or levels, or a loss of expression of Ambra-1 and Loricrin in the tissue, is indicative of an increased risk of metastasis.

In certain embodiments, the method of determining the expression of Loricrin in the tissue sample comprises:
(a) contacting the tissue sample with the antibody against Loricrin; and
(b) visualising the antibody in the tissue sample with a reagent that generates a detectable signal.

Typically, the tissue sample comprises at least a portion of a peri-tumoral epidermis overlying the primary melanoma and the method comprises determining the expression of Loricrin in the stratum corneum of the epidermis.

In certain embodiments, the antibody against Loricrin comprises the following heavy chain variable domain complementarity determining regions (CDRs):
(a) HCDR1 comprising the amino acid sequence of SEQ ID NO: 22;
(b) HCDR2 comprising the amino acid sequence of SEQ ID NO: 23; and
(c) HCDR3 comprising the amino acid sequence of SEQ ID NO: 24.

In certain embodiments, the antibody against Loricrin further comprises the following light chain variable domain CDRs:
(d) LCDR1 comprising the amino acid sequence of SEQ ID NO: 25
(e) LCDR2 comprising the amino acid sequence of SEQ ID NO: 26;
(f) LCDR3 comprising the amino acid sequence of SEQ ID NO: 27.

In certain embodiments, the antibody against Loricrin further comprises the following heavy chain variable domain framework regions (FRs):
(a) HCFR1 comprising the amino acid sequence of SEQ ID NO: 28;
(b) HCFR2 comprising the amino acid sequence of SEQ ID NO:29;
(c) HCFR3 comprising the amino acid sequence of SEQ ID NO: 30; and
(d) HCFR4 comprising the amino acid sequence of SEQ ID NO: 31.

In certain embodiments, the antibody against Loricrin further comprises the following light chain variable domain FRs:
(e) LCFR1 comprising the amino acid sequence of SEQ ID NO: 32;
(f) LCFR2 comprising the amino acid sequence of SEQ ID NO: 33;
(g) LCFR3 comprising the amino acid sequence of SEQ ID NO: 34; and
(h) LCFR4 comprising the amino acid sequence of SEQ ID NO: 35.

In certain embodiments, the antibody against Loricrin further comprises an antibody variable domain comprising:
(a) a $V_H$ sequence having at least 90%, at least 95%, at least 96%, at least 97%, at least 98%, at least 99% or more sequence identity to the amino acid sequence of SEQ ID NO: 36;
(b) a $V_L$ sequence having at least 90%, at least 95%, at least 96%, at least 97%, at least 98%, at least 99% or more sequence identity to the amino acid sequence of SEQ ID NO 37; or
(c) a $V_H$ sequence as in (a) and a $V_L$ sequence as in (b).

In certain embodiments, the antibody against Loricrin comprises:
(d) a $V_H$ sequence comprising SEQ ID NO:36;
(e) a $V_L$ sequence comprising SEQ ID NO: 37; or
(f) a $V_H$ sequence as in (d) and a $V_L$ sequence as in (e).

In certain embodiments, the antibody against Loricrin comprises a Fab fragment comprising:
(a) the Fd chain of SEQ ID NO: 38;
(b) the light chain of SEQ ID NO: 39;
(c) a dimerization domain sequence;
(d) one or more linker sequences; and/or
(e) one or more epitope tags.

The invention provides use of antibodies against Loricrin as described herein in methods of determining whether a subject with melanoma has an increased risk of metastasis. The antibodies against Loricrin may be used in any method, assay or kit described herein.

The invention also provides antibodies that compete for binding to Loricrin with antibodies as described herein.

The invention further provides antibodies that bind to the same epitope as the anti-Loricrin antibody as defined herein.

In certain embodiments, the epitope comprises peptide antigenic determinants within single peptide chains of Loricrin. In certain embodiments, the epitope comprises conformational antigenic determinants comprising one or more contiguous amino acids on a particular chain and/or on spatially contiguous but separate peptide chains. In certain embodiments, the epitope comprise post-translational antigenic determinants comprising molecular structures (e.g. carbohydrate groups) covalently attached to Loricrin.

The epitope may comprise any suitable number and/or type of amino acids, in any suitable position as defined herein. For example, the epitope may comprise about 10 to about 20 amino acids, typically about 15 amino acids, in or more contiguous or non-contiguous locations with respect to the amino acid sequence of Loricrin as set forth in SEQ ID NO: 42.

In certain embodiments, the invention provides antibodies that bind to Loricrin, wherein said antibodies specifically bind to a region comprising 8, 9, 10, 11, 12, 13, 14, 15 or more of the amino acids 2 to 20 of human Loricrin sequence shown in SEQ ID NO: 42. Typically, such antibodies specifically bind to a region comprising SYQKKQPTPGPPVDCVKTS (SEQ ID NO: 54).

In certain embodiments, the invention provides antibodies that bind to Loricrin, wherein said antibodies specifically bind to a region comprising 8, 9, 10, 11, 12, 13, 14, 15 or more of the amino acids 73 to 91 of human Loricrin sequence shown in SEQ ID NO: 42. Typically, such antibodies specifically bind to a region comprising GGG-GIGGPGGGSGGSVKYS (SEQ ID NO: 55).

Typically, such antibodies specifically bind to at least a core region comprising VKYS (SEQ ID NO: 60).

In certain embodiments, the invention provides antibodies that bind to Loricrin, wherein said antibodies specifically bind to a region comprising 8, 9, 10, 11, 12 or more of the amino acids 95 to 109, 120 to 134, 135 to 148, and/or 168 to 182 of human Loricrin sequence shown in SEQ ID NO: 42. Typically, such antibodies specifically bind to one or more regions comprising GSSGGGSGCFSSGGG (SEQ ID NO: 56). Typically, such antibodies specifically bind to at least one or more core regions comprising CFS (SEQ ID NO: 61).

In certain embodiments, the invention provides antibodies that bind to Loricrin, wherein said antibodies specifically bind to a region comprising 8, 9, 10, 11, 12, 13, 14, 15 or more of the amino acids 262 to 280 of human Loricrin sequence shown in SEQ ID NO: 42. Typically, such antibodies specifically bind to a region comprising GIGSGCI-ISGGGSVCGGGS (SEQ ID NO: 57).

In certain embodiments, the invention provides antibodies that bind to Loricrin, wherein said antibodies specifically bind to a region comprising 8, 9, 10, 11, 12, 13, 14, 15 or more of the amino acids 279 to 297 of human Loricrin sequence shown in SEQ ID NO: 42. Typically, such antibodies specifically bind to a region comprising GSSGGGGGGSSVGGSGSGK (SEQ ID NO: 58).

In certain embodiments, the invention provides antibodies that bind to Loricrin, wherein said antibodies specifically bind to a region comprising 5, 6, 7, 8 or more of the amino acids 298 to 308 of human Loricrin sequence shown in SEQ ID NO: 42. Typically, such antibodies specifically bind to a region comprising GVCICHQTQQK (SEQ ID NO: 59).

In certain embodiments, the antibody specifically binds to:
(i) amino acids 2-20 of human Loricrin (SEQ ID NO:42);
(ii) amino acids 73-91 of human Loricrin (SEQ ID NO:42);
(iii) amino acids 95-109 of human Loricrin (SEQ ID NO:42);
(iv) amino acids 120-134 of human Loricrin (SEQ ID NO:42);
(v) amino acids 135-148 of human Loricrin (SEQ ID NO:42);
(vi) amino acids 168-182 of human Loricrin (SEQ ID NO:42);
(vii) amino acids 262-280 of human Loricrin (SEQ ID NO: 42);
(viii) amino acids 279-297 of human Loricrin (SEQ ID NO: 42); and/or
(ix) amino acids 298-308 of human Loricrin (SEQ ID NO: 42).

In certain embodiments, the invention provides a method of labelling Loricrin in a tissue sample overlying a primary melanoma, comprising:
(a) contacting the tissue sample with a monoclonal antibody against Loricrin as defined herein; and
(b) visualising the antibody against Loricrin in the tissue sample with a reagent that generates a detectable signal.

The tissue sample may comprise at least a portion of a peri-tumoral epidermis overlying the primary melanoma and the method comprises determining the expression of Loricrin in the stratum corneum of the epidermis.

Unexpectedly, the combination of consistent and distinct expression patterns of the anti-Ambra-1 and Loricrin antibodies describes herein allows rapid and accurate identification of subjects having decreased or loss of expression of Ambra-1 and/or Loricrin. Thus, the combined use of the anti-Ambra-1 and Loricrin antibodies provides improved methods for determining whether a subject with melanoma has an increased risk of metastasis.

Methods of Treatment

Certain aspects of the present invention provide methods of determining a treatment regime for a subject suffering from melanoma, comprising determining the expression of Ambra-1 (and optionally Loricrin) as described herein.

Aptly, the method further comprises comparing the expression of Ambra-1 (and optionally Loricrin) as described herein.

If expression of Ambra-1 (and optionally Loricrin) is normal or increased, a normal recognized care pathway may be followed.

A "normal recognized care pathway", as will be known to those skilled in the art, will be understood as meaning that a wider excision of the scar left by excision of the primary melanoma is carried out on the subject. The size of the wider excision will be determined by a clinician or surgeon, based on the Breslow depth of the primary melanoma. A normal recognized care pathway may further comprise regular (e.g. every 3-12 months) clinical assessment of the subject for up to 5 years. In embodiments where the primary melanoma is stage 2b or 2c, the normal recognized care pathway may further comprise carrying out a staging CT scan on the subject, from the head to the pelvis, at the time of diagnosis. Some treatment centers offer staging sentinel lymph node biopsy of all stage 2a, 2b and 2c tumors. Thus, in some embodiments, the normal recognized care pathway may further comprise carrying out a sentinel lymph node biopsy.

If expression of Ambra-1 (and optionally Loricrin) is decreased or lost, a systemic anti-cancer treatment regime may be followed.

In some embodiments, a systemic anti-cancer treatment regime comprises administering a therapeutic agent to the subject. Typically, the therapeutic agent is capable of inhibiting, preventing or delaying metastasis of melanoma.

In some embodiments, the therapeutic agent is a chemotherapeutic agent. Any suitable chemotherapeutic agent may be administered to the subject. As used herein, a "chemotherapeutic agent" means any therapeutic agent useful for the treatment of cancer, and encompasses small molecules as well as biological agents, such as antibodies.

In some embodiments, the chemotherapeutic agent is selected from Dacarbazine (DTIC), Temozolomide, Nab-paclitaxel, Paclitaxel, Carmustine (BCNU), Cisplatin, Carboplatin, Vinblastine, interleukin 2, interferon alpha, or any combination thereof.

In some embodiments, the chemotherapeutic agent is a biological agent such as an anti-PD and/or anti-CTLA4 therapy. For example, the biological agent may be selected from ipilumab, nivolumab, pembrolizumab and/or any combination thereof. For example, the biological agent may be selected from nivolumab and ipilimumab. In some embodiments, the biological agent is a B-Raf inhibitor, such as vemurafenib and/or dabrafenib. In certain embodiments, the biological agent is nivolumab and/or ipilimumab; dabrafenib and/or trametinib; vemurafenib and/or cobimetinib; and/or any combination thereof.

Thus, in certain embodiments the invention provides a method of treating a subject suffering from melanoma comprising administering a therapeutic agent to a subject identified as having decreased or loss of expression of Ambra-1 (and optionally Loricrin) by methods described herein.

In certain embodiments, the invention provides a therapeutic agent as described herein for use in a method of treating melanoma in a subject, wherein said subject has been identified as having an increased risk of metastasis according to any method described herein.

Ideally, a subject identified as having an increased risk of metastasis is treated as soon as possible to minimize the chances of development of metastasis. Thus, in some embodiments the method or treatment regime is for preventing, inhibiting or delaying metastasis or decreasing the risk of metastasis in the subject.

In some embodiments, a subject is treated immediately or shortly after being identified as having an increased risk of metastasis.

In some embodiments, treatment with the therapeutic agent is carried out after surgery to excise the primary melanoma.

In some embodiments, a method of treatment or a treatment regime may further include one or more of: intensified imaging (e.g. CT scan, PET, MRI, X-ray) of the subject; discussion and/or offering of, or carrying out, a sentinel lymph node biopsy; partial or complete lymphadenectomy; inclusion of the subject in clinical trials; and radiation therapy.

In some embodiments, a therapeutic agent is administered to the subject no more than 12 weeks, no more than 10 weeks, no more than 6 weeks, no more than 4 weeks, no more than 2 weeks or no more than 1 week after the subject is identified as having a decrease or loss of expression of Ambra-1 in the tissue sample.

Non-limiting routes of administration of the therapeutic agent include by oral, intravenous, intraperitoneal, subcutaneous, intramuscular, topical, intradermal, intranasal or intrabronchial administration (for example as effected by inhalation). In some embodiments, the therapeutic agent is administered parenterally, e.g., intravenously. Common modes of administration by which the therapeutic agent may be administered include, for example, administration as a bolus dose or as an infusion over a set period.

A therapeutic agent may be administered in an amount effective to prevent, inhibit or delay the development of metastasis.

Suitable doses and dosage regimes for a given subject and therapeutic agent can be determined using a variety of different methods, such as body-surface area or body-weight, or in accordance with specialist literature and/or individual hospital protocols. Doses may be further adjusted following consideration of a subject's neutrophil count, renal and hepatic function, and history of any previous adverse effects to the therapeutic agent. Doses may also differ depending on whether a therapeutic agent is used alone or in combination.

The skilled person will recognize that further modes of administration, dosages of therapeutic agents and treatment regimens can be determined by the treating physician according to methods known in the art.

Assays and Kits

Certain aspects of the present invention provide in vitro assays for predicting an increased risk of metastasis in a subject suffering from melanoma.

Aptly, the assay comprises contacting a tissue sample overlying a primary melanoma with an antibody against Ambra-1 as described herein. In the assay, the presence of Ambra-1 creates an Ambra-1-antibody complex. The assay may further comprise detecting and/or quantifying the Ambra-1-antibody complex.

Typically, the step of detecting and/or quantifying the Ambra-1-antibody complex comprises contacting the tissue sample(s) (or the section(s) or portion(s) thereof) with at least one capture agent. Typically, a capture agent which binds specifically to the antibody of the invention is used to detect and/or quantify the Ambra-1-antibody complex.

In some embodiments, the capture agent comprises a binding moiety and a detection moiety.

In some embodiments, the binding moiety is a secondary antibody which binds specifically to the antibody against Ambra-1. For example, the binding moiety may be a universal anti-IgG antibody that is capable of binding to the antibody against Ambra-1 (e.g. a flag sequence of the antibody).

In some embodiments, the binding moiety is an enzyme (e.g. alkaline phosphatase) which binds specifically to the antibody against Ambra-1.

In some embodiments, the method further comprises one or more wash steps to remove unbound antibodies and, optionally, unbound capture agents.

Typically, a suitable detection moiety is selected from a fluorescent moiety, a luminescent moiety, a bioluminescent moiety, a radioactive material, a colorimetric moiety, a nanoparticle having suitable detectable properties, a chromogenic moiety, biotin or an enzyme.

Suitable fluorescent moieties include fluorescent proteins (such as phycoerythrin (PE), peridinin-chlorophyll-protein complex (PerCP) and allophycocyanin (APC)) fluorescent dyes (such as Fluorescein Isothiocyanate (FITC), rhodamines (Rs) and cyanines (Cys)), fluorescent tandem complexes (such as Allophycocyanin-Cyanine 7 (APC-Cy7), Peridinin-Chlorophyll-Protein complex-Cyanine 5 (PerCP-cy5) and Phycoerythrin-Texas Red (PE-TexasRed)), and nanocrystals (such as QDot 525, QDot 545 and QDot 625). The presence of Ambra-1-antibody complexes can be detected using fluorescence microscopy via the use of fluorescent ligands or a capture agent comprising a fluorescent detection moiety.

In embodiments where the detection moiety comprises an enzyme, the presence of the Ambra-1-antibody complex can be detected and/or quantified by detecting and/or quantifying the reaction product of a reaction of a substrate catalyzed by the enzyme. In these embodiments, the method further comprises adding a substrate of the enzyme and detecting and/or quantifying the product of the reaction performed on the substrate by the enzyme. For example, the reaction may result in the production of a colored precipitate, which would be detected using light microscopy. Suitable enzymes include, for example, alkaline phosphatase and horseradish peroxidase. A chromogenic substrate of alkaline phosphatase is PNPP (p-Nitrophenyl Phosphate, Disodium Salt). PNPP produces a yellow water-soluble reaction product that absorbs light at 405 nm. Chromogenic substrates of horseradish peroxidase include ABTS (2,2'-Azinobis [3-ethylbenzothiazoline-6-sulfonic acid]-diammonium salt), which yields a green reaction product, OPD (o-phenylenediamine dihydrochloride) which yields a yellow-orange reaction product, and TMB (3,3',5,5'-tetramethylbenzidine) soluble substrates yield a blue colour when detecting HRP. Other suitable enzyme-substrate combinations, methods of detecting the Ambra-1-antibody complexes, and suitable detection moieties will be known to those skilled in the art.

In certain embodiments, the antibody against Ambra-1 or the capture agent is immobilized on a solid phase surface, for example a microarray, slide, well or bead.

In certain embodiments, the expression of Ambra-1 is detected and/or quantified by visual assessment, for example, microscopy. In other embodiments, the expression of Ambra-1 is detected and/or quantified by an automated slide scanner.

In certain embodiments, the method of detecting and/or quantifying the Ambra-1-antibody complex comprises outputting, optionally on a computer, an indication of whether the one or more complexes are present or absent, and this indicates whether the subject suffering from melanoma has an increased risk of metastasis.

In certain embodiments, the invention further comprises contacting the tissue sample with an antibody against Loricrin as described herein, where the presence of Loricrin creates a Loricrin-antibody complex and detecting and/or quantifying the Loricrin-antibody complex. The Loricrin-antibody complex may be detected and/or quantified as described herein for the Ambra-1-antibody complex.

The invention also provides a kit for predicting an increased risk of developing metastasis of a subject suffering from melanoma, the kit comprising an antibody against Ambra-1 as described herein. In some embodiment, the kit further comprises an antibody against Loricrin as described herein.

In certain embodiments, the kit further comprises instructions for using the kit to predict the risk of metastasis in a subject suffering from melanoma.

In certain embodiments, the kit further comprises at least one capture agent. Typically, a capture agent comprises a detection moiety and/or a binding moiety as described herein.

In certain embodiments, the detection moiety is an enzyme (e.g. alkaline phosphatase) and the kit further comprises a substrate of the enzyme.

Typically, the kit may further comprise one or more additional components such as reagents and/or apparatus necessary for carrying out an in vitro assay, e.g. buffers, fixatives, wash solutions, blocking reagents, diluents, chromogens, enzymes, substrates, test tubes, plates, pipettes etc.

The kit of certain embodiments of the invention may advantageously be used for carrying out a method of certain embodiments of the invention and could be employed in a variety of applications, for example in the diagnostic field or as a research tool. It will be appreciated that the parts of the kit may be packaged individually in vials or in combination in containers or multi-container units. Typically, manufacture of the kit follows standard procedures which are known to the person skilled in the art.

EXAMPLES

Example 1—Production of Anti-Ambra-1 and Anti-Loricrin Antibodies

Anti-Ambra-1 and Loricrin antibodies were produced using BioRad HuCAL PLATINUM® antibody generation technology and CysDisplay® technology. HUCAL stands for 'Human Combinatorial antibody library', which is a synthetic (generated by de novo gene synthesis) antibody library containing human antibody gene sequences covering more than 95% of the human structural gene repertoire (45 billion antibodies) that are cloned in *E. coli* phagemid vectors. Each *E. coli* phage contains one of the 45 billion antibody genes and displays the corresponding antibody on their surface in Fab format, by means of a disulfide linkage between Fab and gene III protein (CysDisplay).

Antigens of Ambra-1 (a synthesized peptide) and Loricrin (native human antigen) were used to isolate the antibodies described herein. The antigens were immobilized on to a solid support (i.e., ELISA microtiter plates or covalently coupled to magnetic beads), before the HuCAL library presented on phage was incubated with the antigens. Non-specific antibodies were removed by washing and specific antibody phages eluted by adding a reducing agent.

CysDisplay technology, where the Fab antibody fragment is linked to the phage by a disulphide bond that is easily cleavable rather than a conventional peptide bond, was used to allow more efficient elution of high affinity phages with reducing agents during antibody selection (Bio-Rad). This ensured that high affinity antibodies were not lost during selection, a common problem with more traditional panning phage display methods.

The specific antibody phages were used to infect an *E. coli* culture along with helper phages, allowing the enriched antibody phage library to be used for subsequent rounds of panning (usually 2-3 rounds of enrichment panning).

After panning, the phagemid DNA encoding the enriched antibody population was isolated as a pool and subcloned into a Fab expression vector containing antibiotic resistance. The vector format chosen was a bivalent Fab (Fab-A-FH) formed with dimerization of bacterial alkaline phosphatase, with two tags Flag (DYKDDDK) and His 6 (His6). *E. coli* was then transformed with the Fab expression vector ligation mixture and plated on agar plates containing antibiotic. Each growing colony represents a monoclonal antibody and was picked and grown in a 384 well microtiter plate. Antibody expression was induced and the culture harvested and lysed to release the antibodies.

Culture lysates were screened primarily for specific antigen binding to antigens by indirect ELISA. 95 ELISA-positive antibody clones, derived from the primary screening, were ranked according to their binding strength (koff-rate determination; 'secondary screening') as measured by Bio-Layer Interferometry using the Pall ForteBio Octet® System. Antibodies were then selected according to both antigen specificity and binding strength. Hits from the primary or secondary antibody screening procedures were sequenced to identify unique antibodies. The Fab antibodies with unique sequences were expressed in *E. coli* and purified using one-step affinity chromatography. Purified antibodies were tested by QC ELISA for required specificity. This QC ELISA screen was performed on native as well as denatured antigen due to the final antibody application of immunohistochemistry, where antigens during the tissue processing may be denatured, as well as immobilized control proteins Glutathione S-transferase, BSA (carrier protein), N1-CD33-His6 (the ectodomain of human CD33 fused to the N1 domain of the g3p filamentous phage M13) used for calculation of background. Purity was assessed by Coomassie® staining of a sodium dodecyl sulfate-polyacrylamide gel (SDS-PAGE) and concentration measured by UV absorbance at 280 nm.

Figure 1:
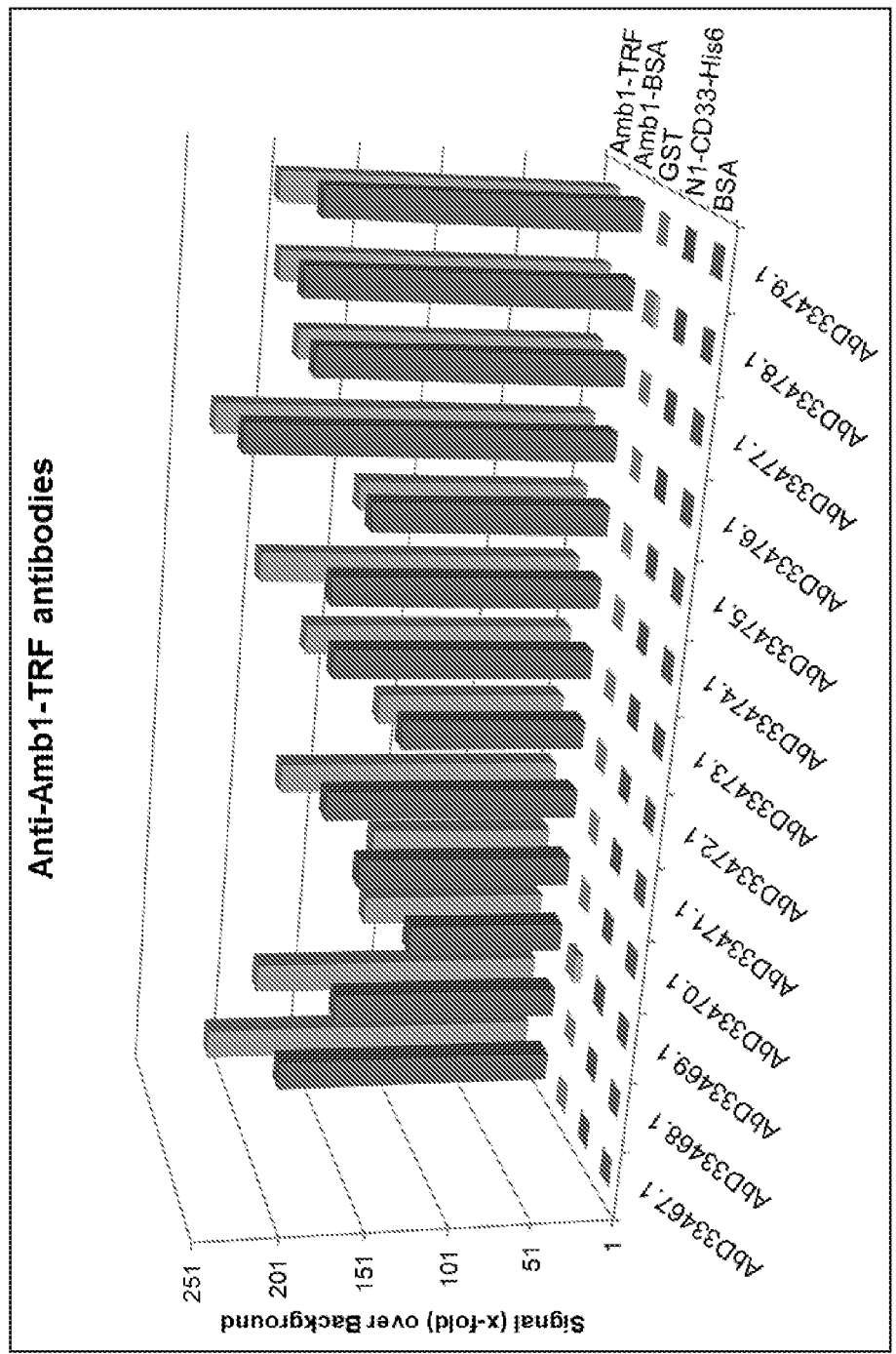
FIG. 1 shows identification of recombinant monoclonal fragment antibodies against human Ambra-1 by ELISA. All HuCAL antibodies have specificity to Ambra-1 peptide in native/denatured form, with no/little cross reactivity to control proteins.
Figure 2:
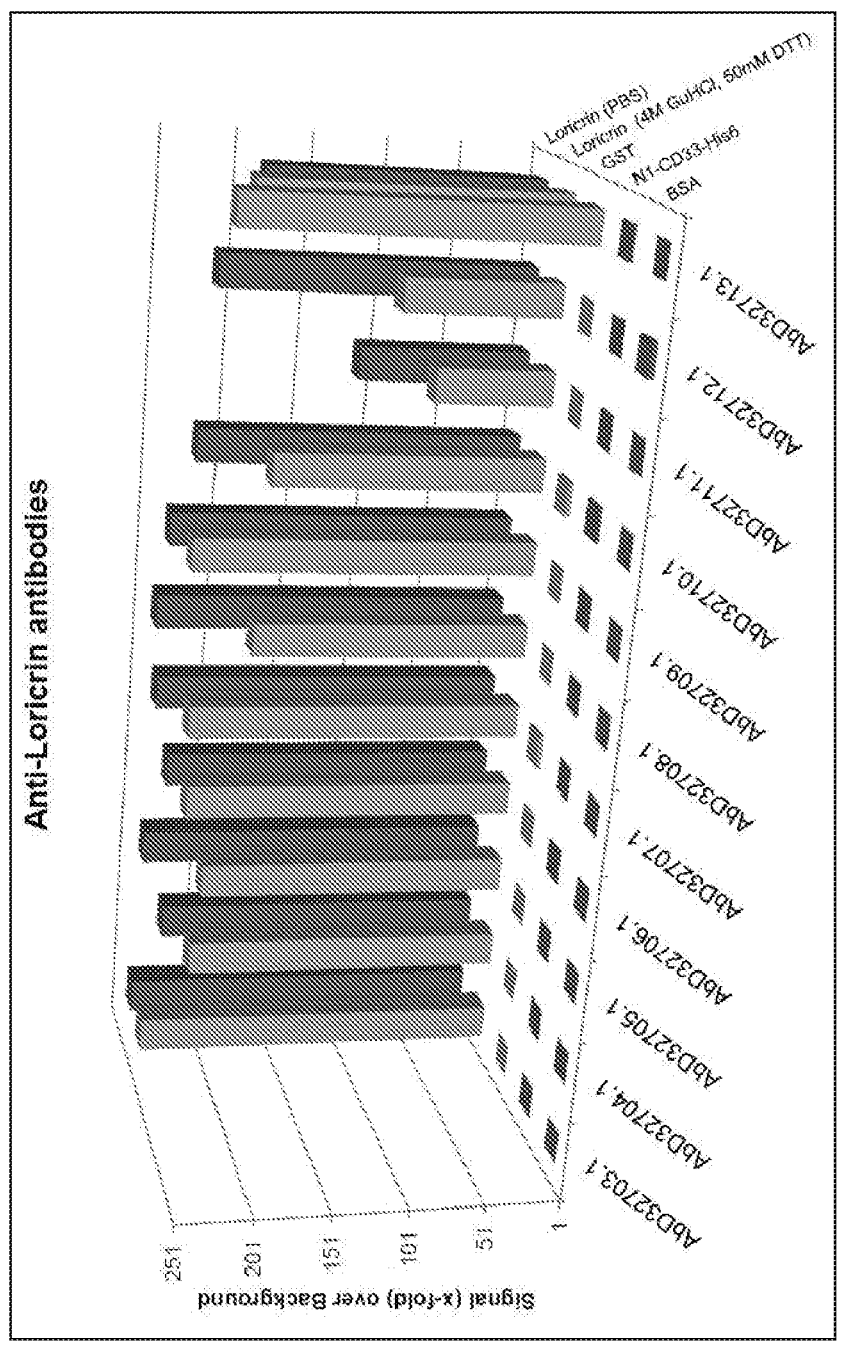
FIG. 2 shows identification of recombinant monoclonal fragment antibodies against human Loricrin by ELISA. All HuCAL antibodies have specificity to Loricrin antigen in native/denatured form, with no/little cross reactivity to control proteins, apart from AbD32713.1 which showed binding to GST and was subsequently omitted from validation on this basis.
Figure 3:
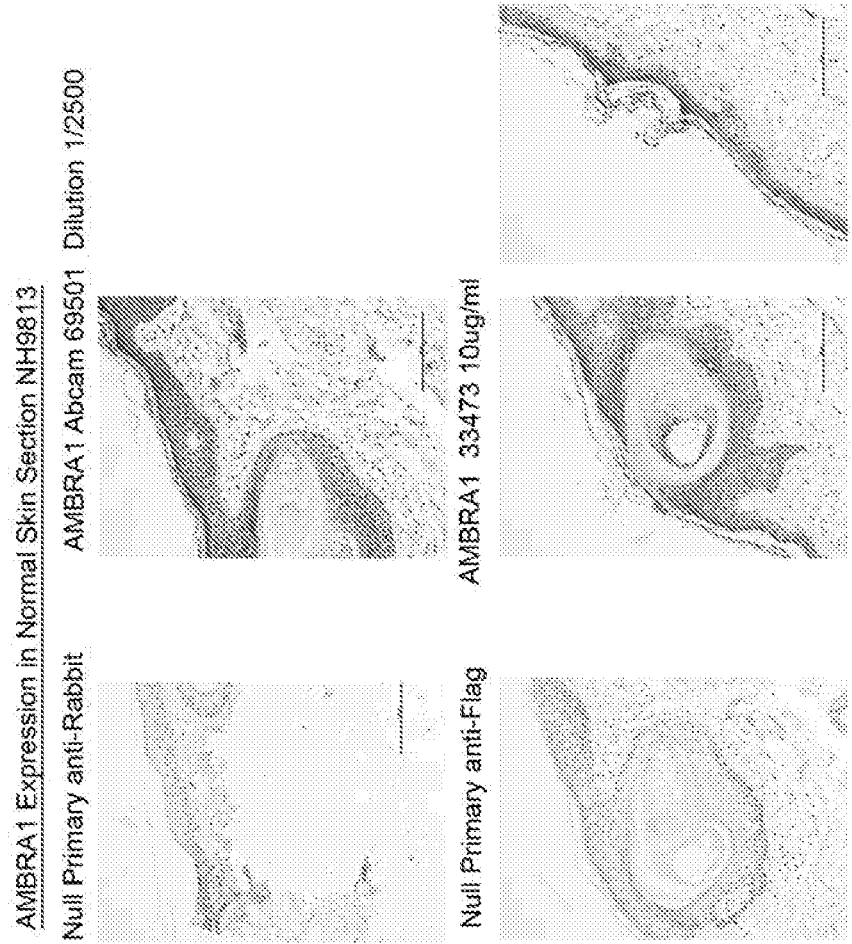
FIG. 3 shows example photomicrographs of Ambra-1 expression in normal skin tissue NH9813 using Abcam antibody ab69501 and HuCAL antibody 33473.
Figure 4:
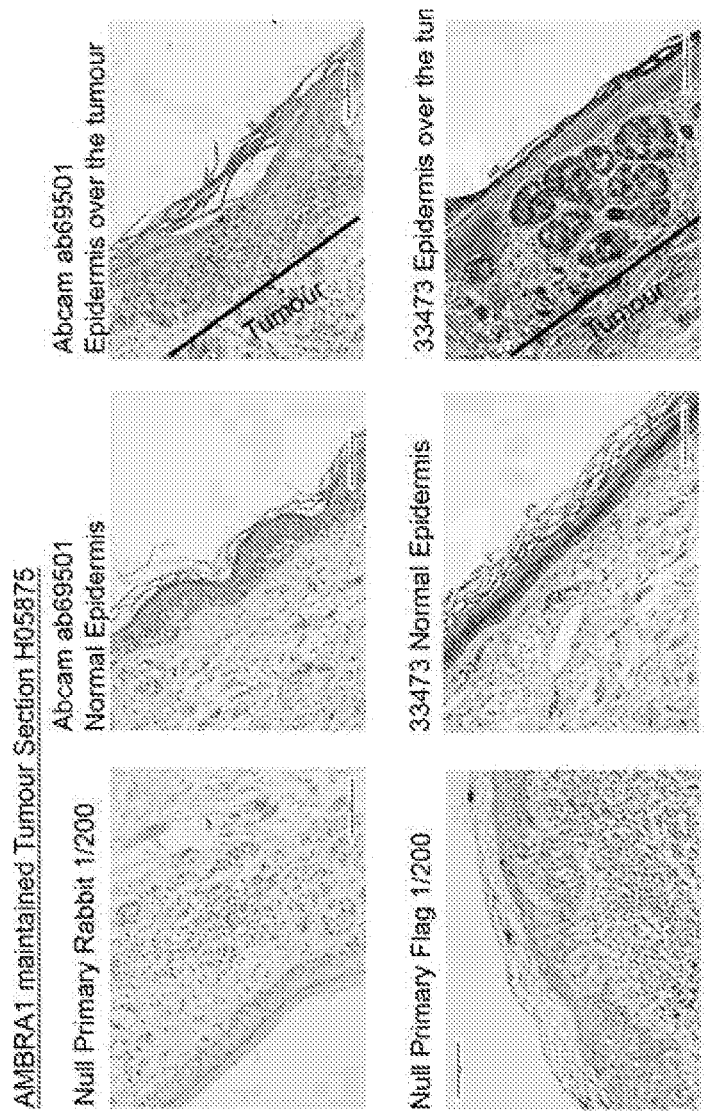
FIG. 4 shows example photomicrographs of Ambra-1 expression in a stage I melanoma tissue with maintained Ambra-1 expression in epidermis overlying the tumor, detected using Abcam antibody ab69501 (diluted 1/2500) and HuCAL antibody 33473 (10 µg/ml).
Figure 5:
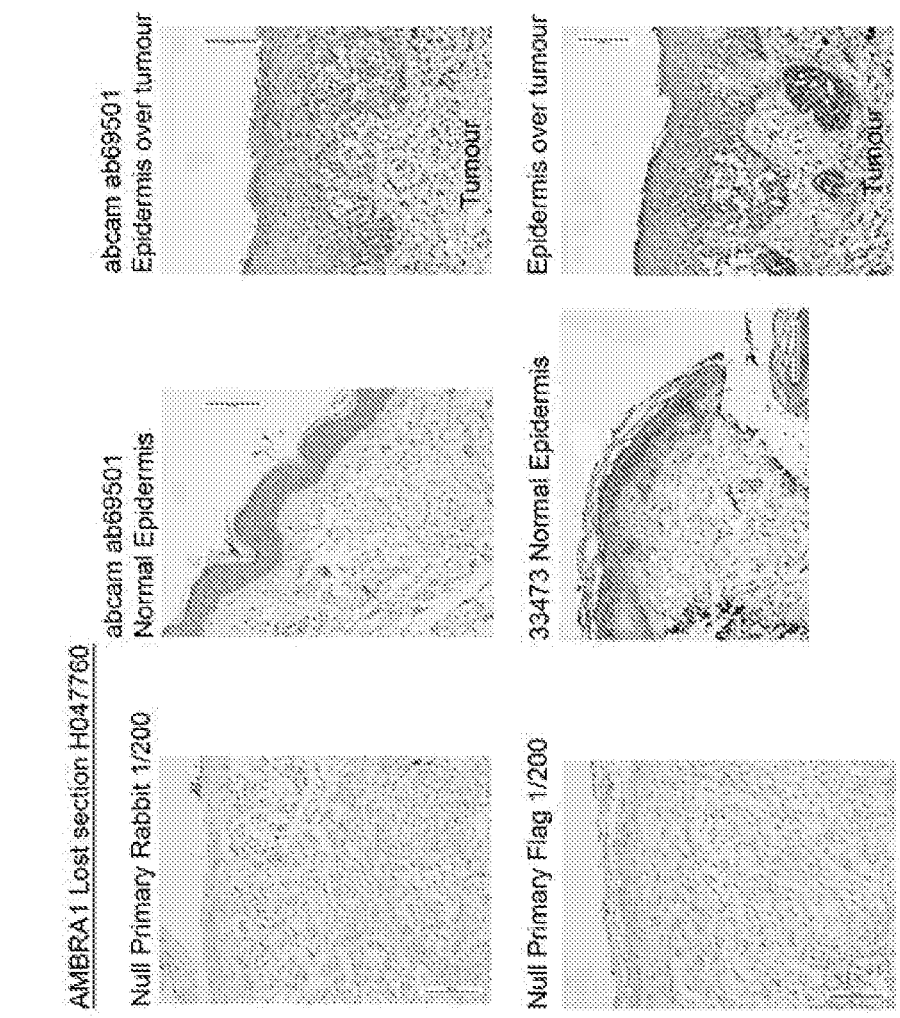
FIG. 5 shows example photomicrographs of Ambra-1 expression in a stage I melanoma tissue with Ambra-1 expression lost in epidermis overlying the tumor, detected using Abcam antibody ab69501 (diluted 1/2500) and HuCAL antibody 33473 (10 µg/ml).
Figure 6:
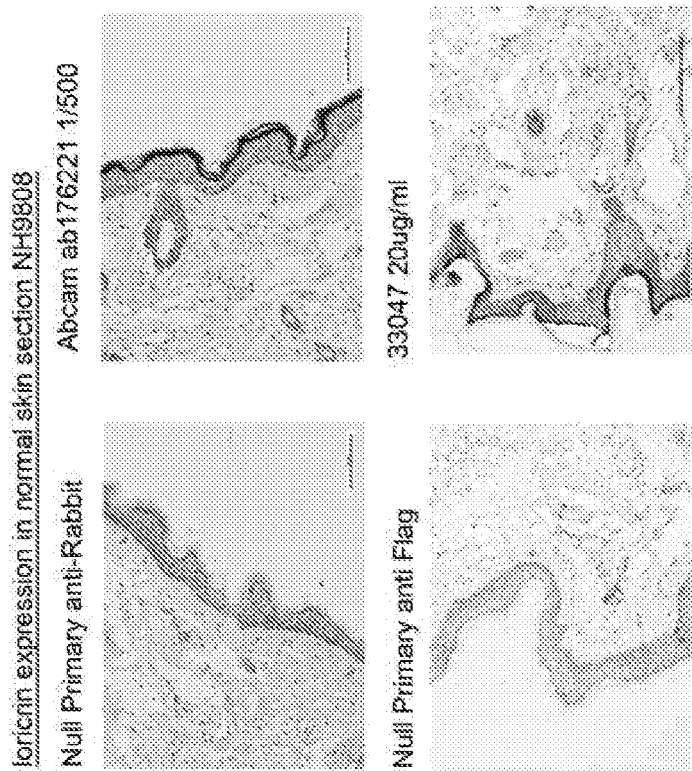
FIG. 6 shows example photomicrographs of Loricrin expression in Normal skin Tissue NH9808 using Abcam antibody ab176221 (diluted 1/500) and HuCAL antibody 33047 (20 µg/ml).
Figure 7:
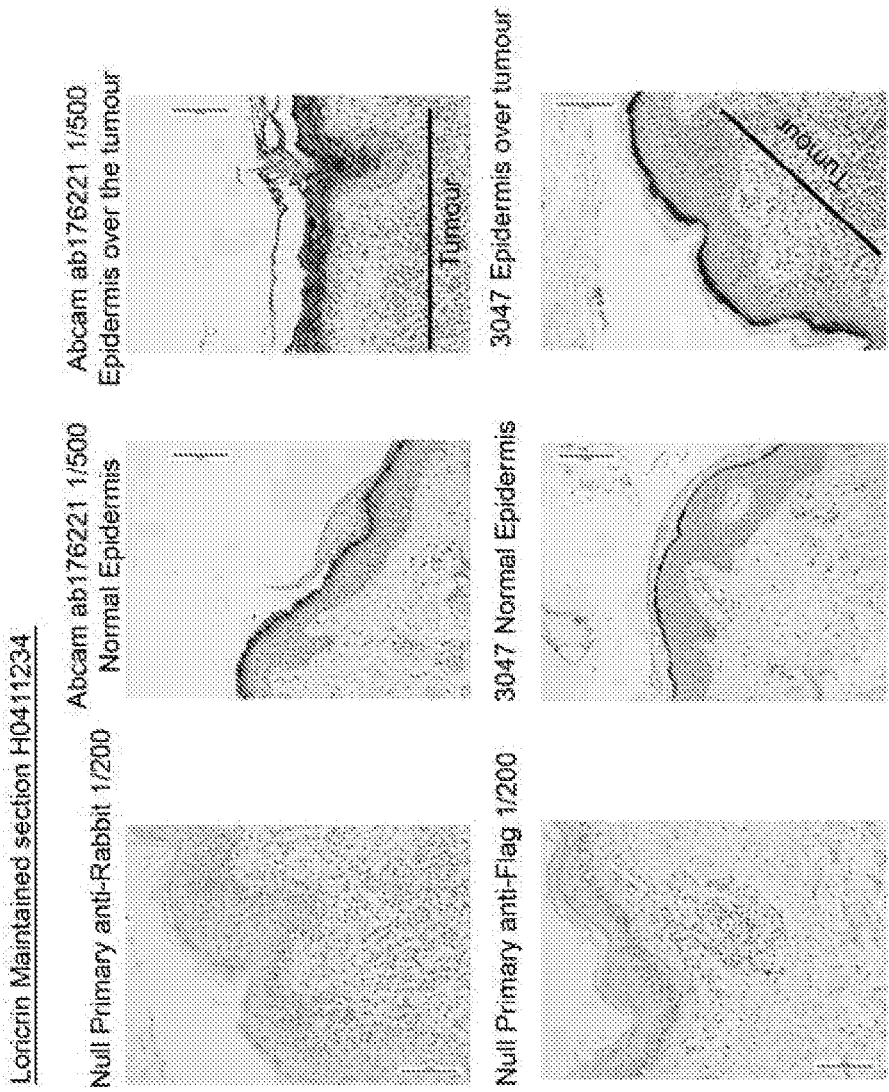
FIG. 7 shows example photomicrographs of Loricrin expression in a stage I melanoma tissue with maintained Loricrin expression in epidermis overlying the tumor, detected using Abcam antibody ab176221 (diluted 1/500) and HuCAL antibody 3047 (20 µg/ml).
Figure 8:
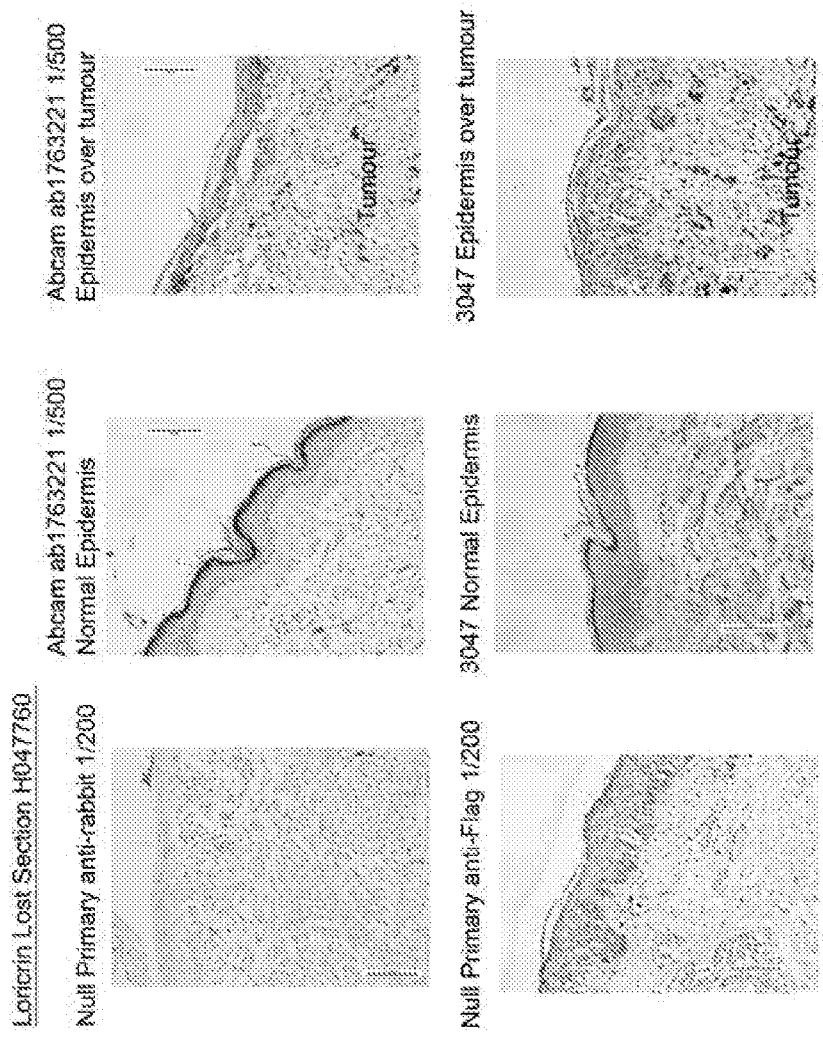
FIG. 8 shows example photomicrographs of Loricrin expression in a stage I melanoma tissue with Loricrin expression lost in epidermis overlying the tumor, detected using Abcam antibody ab176221 (diluted 1/500) and HuCAL antibody 3047 (20 µg/ml).

13 Ambra-1 and 15 loricrin recombinant monoclonal antibody Fab fragments were obtained and used for subsequent validation (FIGS. 1 and 2).

Example 2—Validation of Anti-Ambra-1 and Anti-Loricrin Antibodies

The recombinant human HuCAL antibody fragment antibodies were validated in the first instance using immunohistochemistry protocols on normal skin tissue (where Ambra-1 and Loricrin are expressed) and in a selection of AJCC stage I melanoma tumor tissue (where expression of both AMBRA-1 and Loricrin is maintained in the epidermis overlying the tumor or lost). In all instances the staining of the HuCAL antibodies were compared to commercially available Ambra-1 and Loricrin antibodies by Abcam in the same tissue. Negative control of omitting the primary antibody and using anti-Flag (HuCAL antibodies) or anti-Rabbit (Abcam antibodies) secondary antibodies was also included in each instance.

Materials and Methods

An optimised staining protocol for the Ambra-1 and Loricrin antibodies is described briefly below:

Antigen retrieval buffer 10 mM Tris HCL Ph 9.

Positive control: normal skin section normal epidermis adjacent to tumour in melanoma sections.

Negative controls: Null primaries of normal skin NH9808 and all tumours.

Use research antibody for Loricrin Abcam Ab176322 1/500, 1 hr room temperature, secondary anti-rabbit 1/200 from Rabbit VECTASTAIN Elite ABC HRP Kit (VECTOR laboratories).

Use research antibody for AMBRA-1 Abcam Ab69501 1/2500 1 hr room temperature, secondary anti-rabbit 1/200 from Rabbit VECTASTAIN Elite ABC HRP Kit (VECTOR laboratories).

Test conditions: AMBRA-1 and Loricrin HUCAL antibodies chosen at 20 ug/ml 1 hr room temperature. Secondary antibody used Sigma anti-flag HRP A8592 at 1/200 concentration as optimised for each antibody.

All tissue sections formalin fixed paraffin embedded, cut at 5 μm and baked.

Deparaffinise Sections:
1. Place slides in metal rack and incubate in Histoclear 20 mins.
2. Dip slides in: 100% ethanol for 5 secs, 75% for 5 secs, 50% for 5 secs, dH2O for 5 secs.

Antigen Retrieval:
3. Place slides in plastic rack, with blank slides around the edges to even out the heat.
4. Place in buffer (10 Mm Tris HCl PH 9) and heat in microwave.
5. Allow to cool slowly in buffer solution for 15 minutes.

Permeabilize Cells:
6. Place slides on flat metal tray, draw around sections with hydrophobic pen and allow to dry.
7. Incubate sections with PBS/T (PBS+0.05% Tween 20) for 3 mins to rehydrate sections.
8. Incubate slides in 0.2% Triton X-100 in PBS/T for 10 mins.

Block Endogenous Peroxidase:
9. Wash with PBS/T
10. Incubate with 3% H2O2 in water for 10 min Endogenous Avidin/Biotin Blocking Step:
11. Wash with PBS/T
12. Block endogenous Avidin (Vector Labs Avidin/Biotin Blocking kit) for 15 mins
13. Wash with PBS/T
14. Block endogenous Biotin (Vector Labs Avidin/Biotin Blocking kit) for 15 mins Protein Blocking Step:
15. Wash with PBS/T
16. Incubate with appropriate 2% serum in PBS/T (2 drops in 5 ml) Normal mouse/goat serum (Sigma/Vector Labs) for 20 mins
17. Wash with PBS/T Primary Antibody:
1. Incubate with anti-Loricrin/anti AMBRA-1 primary antibody (in PBS/2% serum) 1 hr room temperature. Incubate positive control slide with research antibody abCam ab176322, ab69501 (PBS/2% serum) 1 hr room temperature.
2. 3× Wash with PBS/T Secondary Antibody:
3. Incubate with biotinylated anti rabbit/anti-flag secondary antibody.
4. Prepare ABC Reagent from Vectastain Elite kit, leave at room temperature for 30 min
a. 2.5 ml PBS+1 drop A+1 drop B
5. 3× Wash with PBS/T Staining:
6. Incubate with ABC reagent for 30 mins.
7. 3× Wash with PBS/T.
8. Prepare DAB substrate as per manufacturer's instructions (Vector, ImmPACT DAB EqV peroxidase substrate SK-4103). Mix an equal volume of DAB reagent 1 and 2, mix well before use (working solution can be stored for 1 week at 2-8° C.).
9. Incubate tissue sections with DAB substrate for 2 mins.
10. Rinse slides in water for 5 mins to stop peroxidase reaction.
11. Incubate in Meyer's Haemalum (hematoxylin) for 10 minutes.
12. Wash 10 min with frequent changes
13. Put slides in: 75% ethanol for 5 secs (blot firmly), 100% ethanol for 5 secs
14. Put slides in Histoclear to clean sections for 2 minutes.
15. Allow slides to dry and mount cover slips with DPX.

Results

Following immunohistochemical analysis, the recombinant human HuCAL antibody fragment for Ambra-1 Abd33473.1 (33473) and Loricrin AbD33047.1 (33047) were selected due to the physiologically relevant expression patterns and staining intensity.

Representative pictomicrographs are shown (see FIGS. 3 to 8), highlighting commercially available Abcam and the selected HuCAL Abd33473.1 and AbD33047.1 antibody staining in normal skin and stage I melanoma tumor tissue where expression of both Ambra-1 and Loricrin maintained or lost in the epidermis overlying the tumor. Importantly, the selected HuCAL Abd33473.1 and AbD33047.1 antibodies led to a more consistent and distinct pattern of expression as compared to the commercially available Abcam antibodies.

Figure 9:
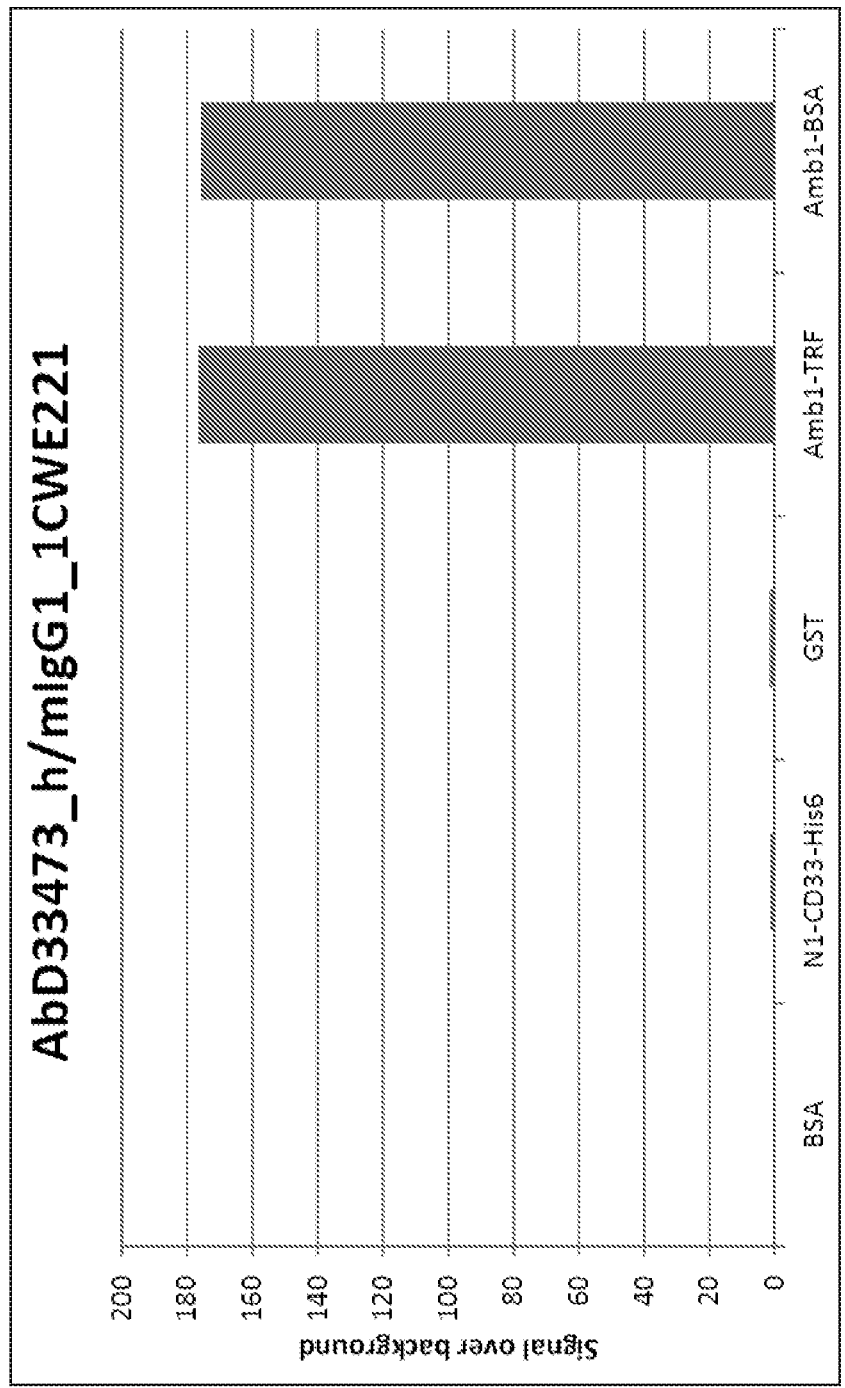
FIG. 9 shows ELISA results of recombinant monoclonal antibody AbD33473 against human Ambra-1.
Figure 10:
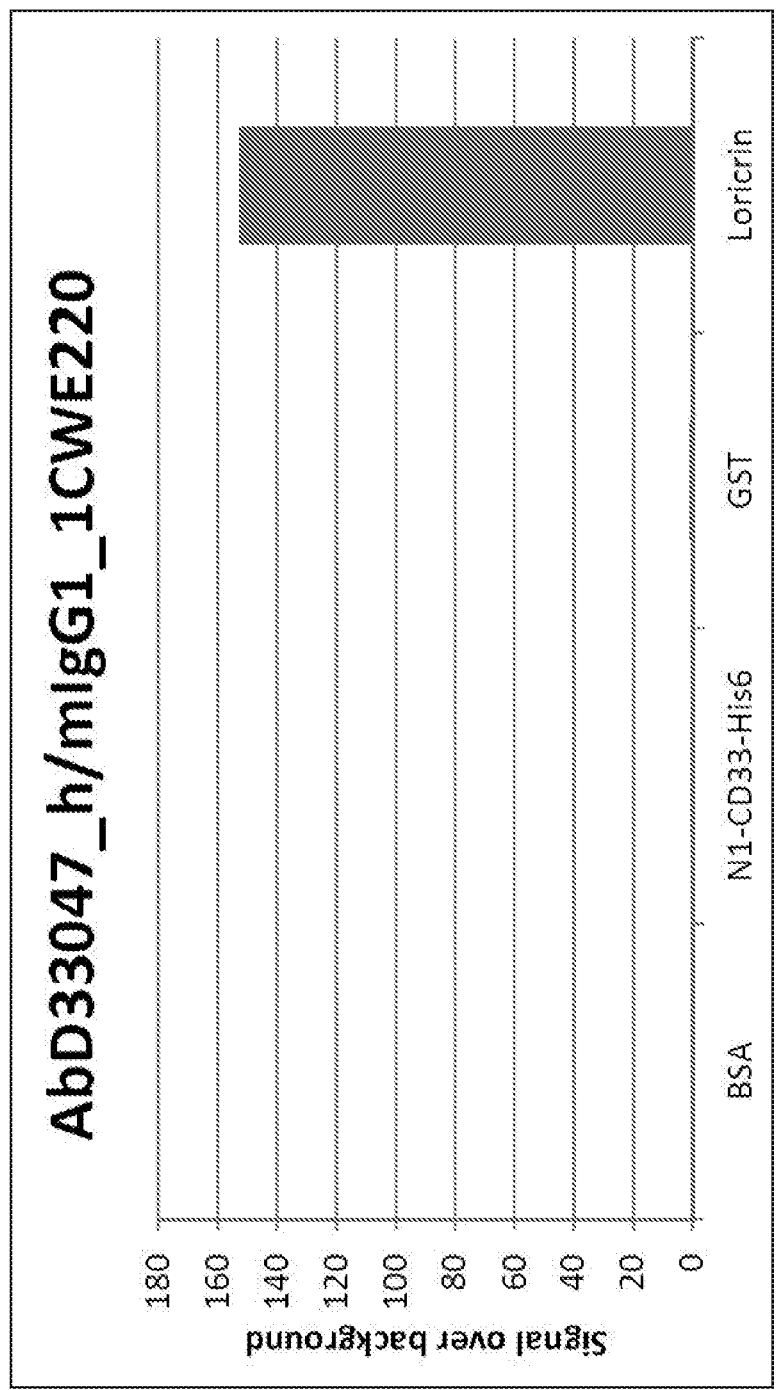
FIG. 10 shows ELISA results of recombinant monoclonal antibody AbD33047 against human Loricrin.

The HuCAL recombinant monoclonal Fab antibody against human Ambra-1 and Loricrin were converted into full length chimeric antibody with an IgG1 mouse Fc region to allow detection of antibodies by standard automated immunohistochemistry. This was achieved by sub-cloning the heavy and light chain genes of the Fab antibody into a vector with an IgG1 mouse constant region, followed by transient expression in mammalian HKB-11 cells, purification from HKB-11 supernatants by affinity chromatography and subsequent quality control by ELISA assay (FIGS. 9 and 10).

The full-length chimeric immunoglobulin antibodies against Ambra-1 and Loricrin were validated by automated immunohistochemistry in a small cohort of AJCC stage I melanoma tumors with AMBRA-1 and Loricrin maintained or lost in the epidermis overlying the tumor. Staining was performed using the Ventana Benchmark XT automated IHC staining instrument (Ventana Medical Systems Inc.) with ultraView Universal DAB Detection Kit (Ventana Medical Systems Inc.) or ultraView Universal Alkaline Phosphatase Red Detection Kit, (Ventana Medical Systems Inc.) according to the manufacturer's specifications. In all instances, the staining of the HuCAL antibodies were compared to commercially available Ambra-1 and Loricrin antibodies by Abcam in the same tissue (FIGS. 11 and 12).

In summary, the recombinant HuCAL antibody fragment Ambra-1 (AbD33473) stained keratinocytes cytoplasmically within the epidermis or normal skin/normal skin adjacent to the tumour, with intensity increasing upwards through the epidermis to the stratum corneum as expected in line with keratinocyte differentiation. This expression was either maintained or lost over the stage I melanoma tumour samples appropriately. Ambra-1 AbD33473 also consistently stained tumor cells, in contrast to the research grade antibodies. Thus, the selected AbD33473 antibody is capable of consistent and superior staining as compared to the research grade polyclonal antibodies.

Loricrin AbD33047 stained cytoplasmically the most differentiated top layer of keratinocytes in the stratum corneum of the epidermis, presenting as a thin line in normal skin/normal skin adjacent to the tumor. This line was either maintained or lost over the stage I melanoma tumor samples appropriately. Thus, the selected AbD33047 antibody allows improved detection of loricrin as compared to the research grade polyclonal antibodies.

Example 3—Epitope Mapping of Anti-Ambra-1 Antibodies

Epitopes of Ambra-1 recognized by anti-Ambra-1 antibodies were mapped using linear, conformational and replacement analysis epitope mapping (Pepscan Presto BV) using established techniques (Timmerman et al (2007). *J. Mol. Recognit.* 20: 283-299; Langedijk et al. (2011) *Analytical Biochemistry* 417: 149-155).

The anti-Ambra-1 antibody was tested on arrays with overlapping linear peptides and looped peptides, based on the C-terminal sequence of Ambra-1:
VSLPSAEGPTLHCELTNNNHLL-DGGSSRGDAAGPRGEPRNR (SEQ ID NO: 27)

The core epitope, based on overlapping peptides in the linear and looped arrays, was determined to be sequence $_{37}EPR_{39}$. A second binding site is apparent only in specific length peptides, and more pronounced in the looped peptide array. Binding to these residues may require a very specific conformation, which in the LOOP11 peptide mimics is provided readily, and can only be induced with the specific residue content in the LIN11 peptides. If so, this suggests that a secondary structure may be formed for recognition of these residues. This recognition occurs only in this length peptide. Thus, it is possible that specific residues need to be aligned precisely to be recognized. This may represent a structure such as a beta turn, in which some residues on opposite strands are required for the formation, allowing the proper positioning of the two identified residues in the loop tip. The location of the two residues in the center of the 11-mers also corroborates such a possibility. In conclusion, the main residues for binding are $_{37}EPR_{39}$, which may be aided by $_{23}DG_{24}$ in a specific conformation.

Details of the epitope information is summarized in the Table below. Core binding sites are listed based on overlap of peptides. Underlined sequence highlights the key residues deducted from the replacement analysis (REPNET):

| Anti-Ambra-1 | Epitope |
|---|---|
| REPNET | $_{23}$DGGSSRGDAAGPRG<u>EPRNR</u>$_{41}$ (SEQ ID NO: 28) |
| LIN | $_{37}$EPR$_{39}$ (SEQ ID NO: 31) <br> $_{13}$HLLDGGSSR$_{28}$ (SEQ ID NO: 29) |
| LOOP | $_{37}$EPR$_{39}$ (SEQ ID NO: 31) <br> $_{13}$NHLLDGGSSR$_{28}$ (SEQ ID NO: 30) |

Example 4—Epitope Mapping of Anti-Loricrin Antibodies

Epitopes of Loricrin recognized by anti-Loricrin antibodies were mapped using linear, conformational and replacement analysis epitope mapping (Pepscan Presto BV) using established techniques (Timmerman et al (2007). *J. Mol. Recognit.* 20: 283-299; Langedijk et al. (2011) *Analytical Biochemistry* 417: 149-155).

The anti-Loricrin antibody was tested on arrays with overlapping linear peptides and looped peptides, based on the full length sequence of Loricrin:

(SEQ ID NO: 42)
MSYQKKQPTPQPPVDCVKTSGGGGGGGSGGGGCGFFGGGGSGGGSSGSG

CGYSGGGGYSGGGCGGGSSGGGGGGIGGCGGGSGGSVKYSGGGGSSGGG

SGCFSSGGGGSGCFSSGGGGSSGGGSGCFSSGGGGSSGGGSGCFSSGGGG

FSGQAVQCQSYGGVSSGGSSGGGSGCFSSGGGGGSVCGYSGGGSGGGSGC

GGGSSGGSGSGYVSSQQVTQTSCAPQPSYGGGSSGGGGSGGSGCFSSGGG

GGSSGCGGGSSGIGSGCIISGGGSVCGGGSSGGGGGGSSVGGSGSGKGVP

ICHQTQQKQAPTWPSK

These studies identified a number of epitopes, as shown in the Table below. Especially significant epitope candidates, for which the highest binding signals were observed, are highlighted. Under the assumption that the binding intensity to the peptide models correlates with the importance of the epitope candidate in a full-length protein context, this indicates them being the main interaction sequences. In case of 73-GGGGIGGPGGGSGGSVKYS-91, double alanine mutation additionally indicated an importance of residues VKYS. Notably, the sequence of Loricrin includes a large degree of sequence similarity and recurring motifs. This results in peptide mimics with similar sequence for different regions (Seq #: 95-109; 120-134; 135-148; 168-182). This should especially be considered for recurring core sequences with lower intensity. These could potentially be so called secondary epitopes that exhibit binding purely due to sequence similarities. Minor peaks that fulfill these characteristics are indicated in the Table below. The recurring sequences that exhibit binding capabilities might also be of supportive nature to antibody binding in a full length Loricrin construct. A decrease in binding to peptides where residues CFS (Seq #: 103-105; 128-130; 143-145; 176-178) are mutated to alanine was observed, especially in case of 15-mer linear mimics. Together with the significant peak intensity and consecutive peptide sequences, this serves as an indication that at least one of the repeating sequences is pointing towards an epitope. Interestingly, the described binding sequence is not or to a varying degree observed in the conformational peptide mimics. This possibly points towards an epitope that does not adapt a defined secondary structure.

| SEQ ID NO: 42 | Epitope | |
|---|---|---|
| 2-20 | SYQKKQPTPGPPVDCVKTS (SEQ ID NO: 54) | Primary |
| 73-91 | GGGGIGGPGGGSGGS<u>VKYS</u> (SEQ ID NO: 55) | Primary |
| 95-109 | GSSGGGSGC<u>FS</u>SGGG (SEQ ID NO: 56) | Recurring |

-continued

| SEQ ID NO: 42 | Epitope | |
|---|---|---|
| 120-134 | GSSGGGSGCFSSGGG (SEQ ID NO: 56) | Recurring |
| 135-148 | GSSGGGSGCFSSGGG (SEQ ID NO: 56) | Recurring |
| 168-182 | GSSGGGSGCFSSGGG (SEQ ID NO: 56) | Recurring |
| 262-280 | GIGSGCIISGGGSVCGGGS (SEQ ID NO: 57) | |

-continued

| SEQ ID NO: 42 | Epitope | |
|---|---|---|
| 279-297 | GSSGGGGGGSSVGGSGSGK (SEQ ID NO: 58) | Primary |
| 298-308 | GVCICHQTQQK (SEQ ID NO: 59) | Primary |

The reader's attention is directed to all papers and documents which are filed concurrently with or before this specification in connection with this application and which are open to public inspection with this specification, and the contents of all such papers and documents are incorporated herein by reference.

The invention claimed is:

1. An in vitro assay for predicting an increased risk of metastasis in a subject suffering from melanoma, the assay comprising:
   contacting a tissue sample obtained from the subject with an antibody against Ambra-1, wherein the antibody against Ambra-1 comprises the following heavy chain variable domain complementarity determining regions (CDRs):
   (a) HCDR1 comprising the amino acid sequence of SEQ ID NO:1;
   (b) HCDR2 comprising the amino acid sequence of SEQ ID NO:2; and
   (c) HCDR3 comprising the amino acid sequence of SEQ ID NO:3; and
   wherein the antibody against Ambra-1 comprises the following light chain variable domain complementarity determining regions (CDRs):
   (a) LCDR1 comprising the amino acid sequence of SEQ ID NO:4;
   (b) LCDR2 comprising the amino acid sequence of SEQ ID NO:5; and
   (c) LCDR3 comprising the amino acid sequence of SEQ ID NO:6,
   wherein the tissue sample comprises tissue overlying a primary melanoma and the presence of Ambra-1 creates an Ambra-1-antibody complex; and
   detecting and/or quantifying the Ambra-1-antibody complex, wherein optionally:
   (a) the tissue sample comprises keratinocytes overlying the primary melanoma and the Ambra-1-antibody complex is detected in the keratinocytes; and/or
   (b) the Ambra-1-antibody complex is detected and/or quantified by visual assessment or by an automated slide scanner.

2. A kit for predicting an increased risk of developing metastasis of a subject suffering from melanoma, the kit comprising an antibody against Ambra-1,
   wherein the antibody against Ambra-1 comprises the following heavy chain variable domain complementarity determining regions (CDRs):
   (a) HCDR1 comprising the amino acid sequence of SEQ ID NO:1;
   (b) HCDR2 comprising the amino acid sequence of SEQ ID NO:2; and
   (c) HCDR3 comprising the amino acid sequence of SEQ ID NO:3; and
   wherein the antibody against Ambra-1 comprises the following light chain variable domain complementarity determining regions (CDRs):
   (a) LCDR1 comprising the amino acid sequence of SEQ ID NO:4;
   (b) LCDR2 comprising the amino acid sequence of SEQ ID NO:5; and
   (c) LCDR3 comprising the amino acid sequence of SEQ ID NO:6,
   wherein optionally the kit further comprises at least one capture agent, wherein the at least one capture agent comprises a detection moiety and/or a binding moiety specific for the antibody against Ambra-1.

3. A method for determining whether a subject with melanoma has an increased risk of metastasis, the method comprising: (i) determining the expression of Ambra-1 in a tissue sample obtained from the subject by contacting the tissue sample with a monoclonal antibody against Ambra-1 and visualizing the antibody in the tissue sample with a reagent that generates a detectable signal, wherein the tissue sample comprises tissue overlying a primary melanoma; and (ii) comparing the expression obtained in (i) with a reference tissue or levels obtained therefrom, wherein a decrease in the expression of Ambra-1 in the tissue sample compared to the reference tissues or levels, or a loss of expression of Ambra-1 in the tissue sample, is indicative of an increased risk of metastasis; and wherein the antibody against Ambra-1 comprises the following heavy chain variable domain complementarity determining regions (CDRs): (a) HCDR1 comprising the amino acid sequence of SEQ ID NO:1; (b) HCDR2 comprising the amino acid sequence of SEQ ID NO:2; and (c) HCDR3 comprising the amino acid sequence of SEQ ID NO:3; and the following light chain variable domain complementarity determining regions (CDRs): (d) LCDR1 comprising the amino acid sequence of SEQ ID NO:4; (e) LCDR2 comprising the amino acid sequence of SEQ ID NO:5; and (f) LCDR3 comprising the amino acid sequence of SEQ ID NO: 6.

4. The method of claim 3, wherein: (a) the tissue sample comprises at least a portion of a peri-tumoral epidermis overlying the primary melanoma; (b) the tissue sample comprises keratinocytes overlying the primary melanoma and the method comprises determining the expression of Ambra-1 in the keratinocytes; and/or (c) the tissue sample is a biopsy, or a section thereof, obtained from the subject.

5. The method of claim 3, wherein the antibody against Ambra-1 comprises the following:
   heavy chain variable domain framework regions (FRs):
   (i) HCFR1 comprising the amino acid sequence of SEQ ID NO:7;
   (ii) HCFR2 comprising the amino acid sequence of SEQ ID NO:8;
   (iii) HCFR3 comprising the amino acid sequence of SEQ ID NO 9; and
   (iv) HCFR4 comprising the amino acid sequence of SEQ ID NO:10.

6. The method of claim 3, wherein the antibody against Ambra-1 comprises the following light chain variable domain FRs:
   (i) LCFR1 comprising the amino acid sequence of SEQ ID NO:11;
   (ii) LCFR2 comprising the amino acid sequence of SEQ ID NO:12;
   (iii) LCFR3 comprising the amino acid sequence of SEQ ID NO:13; and
   (iv) LCFR4 comprising the amino acid sequence of SEQ ID NO:14.

7. The method of claim 3, wherein the antibody against Ambra-1 comprises:
   (a) a VH sequence of SEQ ID NO:15, or a sequence having at least 95% sequence identity to the amino acid sequence of SEQ ID NO:15; and/or
   (b) a VL sequence of SEQ ID NO:16, or a sequence having at least 95% sequence identity to the amino acid sequence of SEQ ID NO:16; or
   (c) a Fab fragment comprising a Fd chain sequence of SEQ ID NO: 17 and/or light chain sequence of SEQ ID NO: 18; and/or
   (d) the following heavy chain variable domain and light chain variable domain FRs:
   (vii) HCFR1 comprising the amino acid sequence of SEQ ID NO:7;
   (viii) HCFR2 comprising the amino acid sequence of SEQ ID NO:8;
   (ix) HCFR3 comprising the amino acid sequence of SEQ ID NO:9;
   (x) HCFR4 comprising the amino acid sequence of SEQ ID NO:10;
   (xi) LCFR1 comprising the amino acid sequence of SEQ ID NO:11;
   (xii) LCFR2 comprising the amino acid sequence of SEQ ID NO:12;
   (xiii) LCFR3 comprising the amino acid sequence of SEQ ID NO:13; and
   (xiv) LCFR4 comprising the amino acid sequence of SEQ ID NO:14.

8. A method for determining a treatment regime for a subject suffering from melanoma, the method comprising: (i) determining the expression of Ambra-1 in a tissue sample obtained from the subject by contacting the tissue sample with a monoclonal antibody against Ambra-1 and visualizing the antibody in the tissue sample with a reagent that generates a detectable signal, wherein the tissue sample comprises tissue overlying a primary melanoma; and (ii) comparing the expression obtained in (i) with a reference tissue or levels obtained therefrom, and (iii) (a) if expression of Ambra-1 is normal, following a normal recognized care pathway, or (b) if expression of Ambra-1 is decreased or lost, treating the subject with a systemic anticancer treatment regime, wherein the antibody against Ambra-1 comprises the following heavy chain variable domain complementarity determining regions (CDRs): (a) HCDR1 comprising the amino acid sequence of SEQ ID NO:1; (b) HCDR2 comprising the amino acid sequence of SEQ ID NO:2; and (c) HCDR3 comprising the amino acid sequence of SEQ ID NO:3; and the following light chain variable domain complementarity determining regions (CDRs): (d) LCDR1 comprising the amino acid sequence of SEQ ID NO:4; (e) LCDR2 comprising the amino acid sequence of SEQ ID NO:5; and (f) LCDR3 comprising the amino acid sequence of SEQ ID NO:6.

9. The method of claim 8, wherein:
   (i) the tissue sample comprises keratinocytes overlying the primary melanoma and the method comprises determining the expression of Ambra-1 in the keratinocytes;
   (ii) the antibody against Ambra-1 specifically binds to:
   (a) amino acids 1280-1281 and/or 1294-1296 of human Ambra-1 (SEQ ID NO:21);
   (b) amino acids 1277-1285 and/or 1294-1296 of human Ambra-1 (SEQ ID NO:21); and/or
   (c) amino acids 1280-1296 of human Ambra-1 (SEQ ID NO:21);
   (iii) the systemic anti-cancer treatment regime is for preventing, inhibiting or delaying metastasis or decreasing the risk of metastasis in the subject; and/or
   (iv) the systemic anti-cancer treatment regime comprises administering a therapeutic agent to the subject.

10. A method of treating a subject suffering from melanoma, the method comprising: (i) determining the expression of Ambra-1 in a tissue sample obtained from the subject using a monoclonal antibody against Ambra-1, wherein the tissue sample comprises tissue overlying a primary melanoma; and (ii) comparing the expression obtained in (i) with a reference tissue or levels obtained therefrom, and If there is a decrease in the expression of Ambra-1 in the tissue sample compared to the reference tissue or levels, or a loss of expression of Arnbra-1, administering a therapeutic agent to the subject, wherein the antibody against Ambra-1 comprises the following heavy chain variable domain complementarity determining regions (CDRs): (a) HCDR1 comprising the amino acid sequence of SEQ ID NO:1; (b) HCDR2 comprising the amino acid sequence of SEQ ID NO:2; and (c) HCDR3 comprising the amino acid sequence of SEQ ID NO:3; and the following light chain variable domain complementarity determining regions (CDRs): (d) LCDR1 comprising the amino acid sequence of SEQ ID NO:4; (e) LCDR2 comprising the amino acid sequence of SEQ ID NO:5; and (f) LCDR3 comprising the amino acid sequence of SEQ ID NO:6.

11. The method of claim 10, wherein:
   (i) the tissue sample comprises keratinocytes overlying the primary melanoma and the method comprises determining the expression of Ambra-1 in the keratinocytes;
   (ii) the antibody against Ambra-1 specifically binds to:
   (a) amino acids 1280-1281 and/or 1294-1296 of human Ambra-1 (SEQ ID NO:21);
   (b) amino acids 1277-1285 and/or 1294-1296 of human Ambra-1 (SEQ ID NO:21); and/or
   (c) amino acids 1280-1296 of human Ambra-1 (SEQ ID NO:21); and/or
   (iii) the therapeutic agent is:
   (a) a chemotherapeutic agent, optionally selected from Dacarbazine (DTIC), Temozolomide, Nab-paclitaxel, Paclitaxel, Carmustine (BCNU), Cisplatin, Carboplatin, Vinblastine, interleukin 2, interferon alpha, antibodies and B-Raf inhibitors, or
   (b) a biological agent, optionally selected from:
   (1) nivolumab and/or ipilimumab;
   (2) dabrafenib and/or trametinib;
   (3) vemurafenib and/or cobimetinib; and/or
   (4) any combination thereof.

12. The method of claim 10, wherein the therapeutic agent is administered to the subject no more than 12 weeks after determining a decrease or loss of expression of Ambra-1 in the tissue sample.

13. The method of claim 3, wherein:
(a) the reference levels are levels of Ambra-1 expression that are characteristic of normal tissue;
(b) the reference tissue comprises normal tissue, optionally wherein the normal tissue is epidermis from a site which does not include a primary melanoma;
(c) the reference tissue is an internal reference;
(d) the normal tissue is from a site adjacent to the primary melanoma;
(e) the expression of Ambra-1 in the tissue sample is from about 25% to about 75% of the respective reference level;
(f) the expression of Ambra-1 in the tissue sample is less than about 25% of the respective reference level; and/or
(g) the expression of Ambra-1 in the tissue sample is determined by visual assessment or by an automatic slide scanner.

14. A method of treating a subject suffering from melanoma, the method comprising administering a therapeutic agent to the subject, wherein the subject has been identified as having decreased or a loss of expression of Ambra-1 after determining the expression of Ambra-1 in a tissue sample obtained from the subject by contacting the tissue sample with a monoclonal antibody against Ambra-1 and visualizing the antibody in the tissue sample with a reagent that generates a detectable signal, wherein the antibody against Ambra-1 comprises the following heavy chain variable domain complementarity determining regions (CDRs): (a) HCDR1 comprising the amino acid sequence of SEQ ID NO:1; (b) HCDR2 comprising the amino acid sequence of SEQ ID NO:2; and (c) HCDR3 comprising the amino acid sequence of SEQ ID NO:3; and the following light chain variable domain complementarity determining regions (CDRs): (d) LCDR1 comprising the amino acid sequence of SEQ ID NO:4; (e) LCDR2 comprising the amino acid sequence of SEQ ID NO:5; and (f) LCDR3 comprising the amino acid sequence of SEQ ID NO:6, wherein the method is for inhibiting metastasis or decreasing the risk of metastasis in the subject.

15. The method of claim 14, wherein the subject, prior to identification, was ineligible for therapeutic agent treatment and/or wherein the therapeutic agent is administered to the subject no more than 12 weeks after the subject has been identified as having decreased or loss of expression of Ambra-1 in the tissue sample,
wherein optionally the therapeutic agent is a chemotherapeutic agent, optionally selected from:
(i) Dacarbazine (DTIC), Temozolomide, Nab-paclitaxel, Paclitaxel, Carmustine (BCNU), Cisplatin, Carboplatin, Vinblastine, interleukin 2, interferon alpha, antibodies and B-Raf inhibitors; or
(ii) nivolumab and/or ipilimumab; dabrafenib and/or trametinib; vemurafenib and/or cobimetinib and/or any combination thereof.

16. The method of claim 1, wherein: (a) the subject is suffering from American Joint Commission on Cancer (AJCC) stage 1, stage 2, stage 3 or stage 4 melanoma; (b) the subject is suffering from AJCC stage 1a, stage 1b, stage 2a, stage 2b or stage 2c melanoma; and/or (c) the subject has an ulcerated melanoma.

\* \* \* \* \*

SEQUENCE LISTING

```
<160> NUMBER OF SEQ ID NOS: 61

<210> SEQ ID NO 1
<211> LENGTH: 5
<212> TYPE: PRT
<213> ORGANISM: Artificial Sequence
<220> FEATURE:
<223> OTHER INFORMATION: A synthetic HCDR1 of the anti-Ambra-1 antibody

<400> SEQUENCE: 1

Ser Tyr Trp Ile His
1               5

<210> SEQ ID NO 2
<211> LENGTH: 17
<212> TYPE: PRT
<213> ORGANISM: Artificial Sequence
<220> FEATURE:
<223> OTHER INFORMATION: A synthetic HCDR2 of the anti-Ambra-1 antibody

<400> SEQUENCE: 2

Thr Ile Phe Pro Ser Arg Ser Tyr Thr Thr Tyr Ser Pro Ser Phe Gln
1               5                   10                  15

Gly

<210> SEQ ID NO 3
<211> LENGTH: 13
<212> TYPE: PRT
<213> ORGANISM: Artificial Sequence
<220> FEATURE:
<223> OTHER INFORMATION: A synthetic HCDR3 of the anti-Ambra-1 antibody

<400> SEQUENCE: 3

Asp Thr Pro Ser Thr Ala Leu Lys Ser Pro Phe Asp Tyr
1               5                   10

<210> SEQ ID NO 4
<211> LENGTH: 13
<212> TYPE: PRT
<213> ORGANISM: Artificial Sequence
<220> FEATURE:
<223> OTHER INFORMATION: A synthetic LCDR1 of the anti-Ambra-1 antibody

<400> SEQUENCE: 4

Ser Gly Ser Ser Ser Asn Ile Gly Tyr Asn Tyr Val Tyr
1               5                   10

<210> SEQ ID NO 5
```

-continued

```
<211> LENGTH: 7
<212> TYPE: PRT
<213> ORGANISM: Artificial Sequence
<220> FEATURE:
<223> OTHER INFORMATION: A synthetic LCDR2 of the anti-Ambra-1 antibody

<400> SEQUENCE: 5

Glu Asn Asn Lys Arg Pro Ser
1               5

<210> SEQ ID NO 6
<211> LENGTH: 11
<212> TYPE: PRT
<213> ORGANISM: Artificial Sequence
<220> FEATURE:
<223> OTHER INFORMATION: A synthetic LCDR3 of the anti-Ambra-1 antibody

<400> SEQUENCE: 6

Ser Ser Trp Asp Ser His Ser Asn Ser Tyr Val
1               5                   10

<210> SEQ ID NO 7
<211> LENGTH: 30
<212> TYPE: PRT
<213> ORGANISM: Artificial Sequence
<220> FEATURE:
<223> OTHER INFORMATION: A synthetic HCFR1 of the anti-Ambra-1 antibody

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser
            20                  25                  30

<210> SEQ ID NO 8
<211> LENGTH: 14
<212> TYPE: PRT
<213> ORGANISM: Artificial Sequence
<220> FEATURE:
<223> OTHER INFORMATION: A synthetic HCFR2 of the anti-Ambra-1 antibody

<400> SEQUENCE: 8

Trp Val Arg Gln Met Pro Gly Lys Gly Leu Glu Trp Met Gly
1               5                   10

<210> SEQ ID NO 9
<211> LENGTH: 32
<212> TYPE: PRT
<213> ORGANISM: Artificial Sequence
<220> FEATURE:
<223> OTHER INFORMATION: A synthetic HCFR3 of the anti-Ambra-1 antibody

<400> SEQUENCE: 9

Gln Val Thr Ile Ser Ala Asp Lys Ser Ile Ser Thr Ala Tyr Leu Gln
1               5                   10                  15

Trp Ser Ser Leu Lys Ala Ser Asp Thr Ala Met Tyr Tyr Cys Ala Arg
            20                  25                  30

<210> SEQ ID NO 10
<211> LENGTH: 11
<212> TYPE: PRT
<213> ORGANISM: Artificial Sequence
<220> FEATURE:
<223> OTHER INFORMATION: A synthetic HCFR4 of the anti-Ambra-1 antibody

<400> SEQUENCE: 10
```

Trp Gly Gln Gly Thr Leu Val Thr Val Ser Ser
1               5                   10

<210> SEQ ID NO 11
<211> LENGTH: 22
<212> TYPE: PRT
<213> ORGANISM: Artificial Sequence
<220> FEATURE:
<223> OTHER INFORMATION: A synthetic LCFR1 of the anti-Ambra-1 antibody

<400> SEQUENCE: 11

Asp Ile Val Leu Thr Gln Pro Pro Ser Val Ser Gly Ala Pro Gly Gln
1               5                   10                  15

Arg Val Thr Ile Ser Cys
            20

<210> SEQ ID NO 12
<211> LENGTH: 15
<212> TYPE: PRT
<213> ORGANISM: Artificial Sequence
<220> FEATURE:
<223> OTHER INFORMATION: A synthetic LCFR2 of the anti-Ambra-1 antibody

<400> SEQUENCE: 12

Trp Tyr Gln Gln Leu Pro Gly Thr Ala Pro Lys Leu Leu Ile Tyr
1               5                   10                  15

<210> SEQ ID NO 13
<211> LENGTH: 32
<212> TYPE: PRT
<213> ORGANISM: Artificial Sequence
<220> FEATURE:
<223> OTHER INFORMATION: A synthetic LCFR3 of the anti-Ambra-1 antibody

<400> SEQUENCE: 13

Gly Val Pro Asp Arg Phe Ser Gly Ser Lys Ser Gly Thr Ser Ala Ser
1               5                   10                  15

Leu Ala Ile Thr Gly Leu Gln Ala Glu Asp Glu Ala Asp Tyr Tyr Cys
            20                  25                  30

<210> SEQ ID NO 14
<211> LENGTH: 12
<212> TYPE: PRT
<213> ORGANISM: Artificial Sequence
<220> FEATURE:
<223> OTHER INFORMATION: A synthetic LCFR4 of the anti-Ambra-1 antibody

<400> SEQUENCE: 14

Phe Gly Gly Gly Thr Lys Leu Thr Val Leu Gly Gln
1               5                   10

<210> SEQ ID NO 15
<211> LENGTH: 122
<212> TYPE: PRT
<213> ORGANISM: Artificial Sequence
<220> FEATURE:
<223> OTHER INFORMATION: A synthetic VH domain of the anti-Ambra-1
      antibody

<400> SEQUENCE: 15

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Tyr
            20                  25                  30

Trp Ile His Trp Val Arg Gln Met Pro Gly Lys Gly Leu Glu Trp Met

```
                    35                  40                  45
Gly Thr Ile Phe Pro Ser Arg Ser Tyr Thr Tyr Ser Pro Ser Phe
            50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Thr Pro Ser Thr Ala Leu Lys Ser Pro Phe Asp Tyr Trp
                100                 105                 110

Gly Gln Gly Thr Leu Val Thr Val Ser Ser
            115                 120

<210> SEQ ID NO 16
<211> LENGTH: 112
<212> TYPE: PRT
<213> ORGANISM: Artificial Sequence
<220> FEATURE:
<223> OTHER INFORMATION: A synthetic VL domain of the anti-Ambra-1
      antibody

<400> SEQUENCE: 16

Asp Ile Val Leu Thr Gln Pro Pro Ser Val Ser Gly Ala Pro Gly Gln
1               5                   10                  15

Arg Val Thr Ile Ser Cys Ser Gly Ser Ser Asn Ile Gly Tyr Asn
                20                  25                  30

Tyr Val Tyr Trp Tyr Gln Gln Leu Pro Gly Thr Ala Pro Lys Leu Leu
            35                  40                  45

Ile Tyr Glu Asn Asn Lys Arg Pro Ser Gly Val Pro Asp Arg Phe Ser
        50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Trp Asp Ser His Ser
                85                  90                  95

Asn Ser Tyr Val Phe Gly Gly Gly Thr Lys Leu Thr Val Leu Gly Gln
            100                 105                 110

<210> SEQ ID NO 17
<211> LENGTH: 224
<212> TYPE: PRT
<213> ORGANISM: Artificial Sequence
<220> FEATURE:
<223> OTHER INFORMATION: A synthetic Fd chain (VH domain and constant
      domain) of the Fab region of the anti-Ambra-1 antibody

<400> SEQUENCE: 17

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Ser Ser Tyr
                20                  25                  30

Trp Ile His Trp Val Arg Gln Met Pro Gly Lys Gly Leu Glu Trp Met
            35                  40                  45

Gly Thr Ile Phe Pro Ser Arg Ser Tyr Thr Tyr Ser Pro Ser Phe
        50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Thr Pro Ser Thr Ala Leu Lys Ser Pro Phe Asp Tyr Trp
```

```
                100              105               110
Gly Gln Gly Thr Leu Val Thr Val Ser Ser Ala Ser Thr Lys Gly Pro
            115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
            195                 200                 205

His Lys Pro Ser Asn Thr Lys Val Asp Lys Lys Val Glu Pro Lys Ser
    210                 215                 220
```

<210> SEQ ID NO 18
<211> LENGTH: 215
<212> TYPE: PRT
<213> ORGANISM: Artificial Sequence
<220> FEATURE:
<223> OTHER INFORMATION: A synthetic light chain (VL domain and constant domain) of the Fab region of the anti-Ambra-1 antibody

<400> SEQUENCE: 18

```
Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Tyr Asn
            20                  25                  30

Tyr Val Tyr Trp Tyr Gln Gln Leu Pro Gly Thr Ala Pro Lys Leu Leu
        35                  40                  45

Ile Tyr Glu Asn Asn Lys Arg Pro Ser Gly Val Pro Asp Arg Phe Ser
50                  55                  60

Gly Ser Lys Ser Gly Thr Ser Ala Ser Leu Ala Ile Thr Gly Leu Gln
65                  70                  75                  80

Ala Glu Asp Glu Ala Asp Tyr Tyr Cys Ser Ser Trp Asp Ser His Ser
                85                  90                  95

Asn Ser Tyr Val Phe Gly Gly Gly Thr Lys Leu Thr Val Leu Gly Gln
            100                 105                 110

Pro Lys Ala Ala Pro Ser Val Thr Leu Phe Pro Pro Ser Ser Glu Glu
        115                 120                 125

Leu Gln Ala Asn Lys Ala Thr Leu Val Cys Leu Ile Ser Asp Phe Tyr
    130                 135                 140

Pro Gly Ala Val Thr Val Ala Trp Lys Ala Asp Ser Ser Pro Val Lys
145                 150                 155                 160

Ala Gly Val Glu Thr Thr Thr Pro Ser Lys Gln Ser Asn Asn Lys Tyr
                165                 170                 175

Ala Ala Ser Ser Tyr Leu Ser Leu Thr Pro Glu Gln Trp Lys Ser His
            180                 185                 190

Arg Ser Tyr Ser Cys Gln Val Thr His Glu Gly Ser Thr Val Glu Lys
        195                 200                 205

Thr Val Ala Pro Thr Glu Ala
    210                 215
```

<210> SEQ ID NO 19
<211> LENGTH: 2085

<212> TYPE: DNA
<213> ORGANISM: Artificial Sequence
<220> FEATURE:
<223> OTHER INFORMATION: A synthetic Fd chain of the Fab region and tags of the anti-Ambra-1 antibody

<400> SEQUENCE: 19

| | | | | | |
|---|---|---|---|---|---|
| gaagtgcaat | tggtgcagag | cggtgcggaa | gtgaaaaaac | cgggcgaaag | cctgaaaatt | 60 |
| agctgcaaag | ctccggata | tagcttctct | tcttactgga | tccattgggt | gcgccagatg | 120 |
| ccgggcaaag | gtctcgagtg | gatgggcact | atcttcccgt | ctcgtagcta | caccacttat | 180 |
| agcccgagct | ttcagggcca | ggtgaccatt | agcgcggata | aaagcatcag | caccgcgtat | 240 |
| ctgcaatgga | gcagcctgaa | agcgagcgat | accgcgatgt | attattgcgc | gcgtgacact | 300 |
| ccgtctactg | ctctgaaatc | tccgttcgat | tactggggcc | aaggcaccct | ggtgactgtt | 360 |
| agctcagcgt | cgaccaaagg | cccgagcgtg | tttccgctgg | ccccgagcag | caaaagcacc | 420 |
| agcggcggca | ccgccgcact | gggctgcctg | gtgaaagatt | atttcccgga | accagtgacc | 480 |
| gtgagctgga | acagcggtgc | cctgaccagc | ggcgtgcata | cctttccggc | ggtgctgcaa | 540 |
| agcagcggcc | tgtatagcct | gagcagcgtt | gtgaccgtgc | cgagcagcag | cctgggcacc | 600 |
| cagacctata | tttgcaacgt | caaccataaa | ccgagcaaca | ccaaagtcga | taaaaaagtc | 660 |
| gaaccgaaaa | gcgaattcaa | ggctgaaatg | cctgttctgg | aaaaccgggc | tgctcagggc | 720 |
| gatattacta | caccggcgg | tgctcgccgt | ttaacgggtg | atcagactgc | cgctctgcgt | 780 |
| gattctctta | gcgataaacc | tgcaaaaaat | attattttgc | tgattggcga | tgggatgggg | 840 |
| gactcggaaa | ttactgccgc | acgtaattat | gccgaaggtg | cgggcggctt | ttttaaaggt | 900 |
| atagatgcct | taccgcttac | cgggcaatac | actcactatg | cgctgaatag | aaaaaccggc | 960 |
| aaaccggact | acgtcaccag | ctcggctgca | tcagcaaccg | cctggtcaac | cggtgtcaaa | 1020 |
| acctataacg | cgcgctggg | cgtcgatatt | cacgaaaaag | atcacccaac | gattctggaa | 1080 |
| atggcaaaag | ccgcaggtct | ggcgaccggt | aacgtttcta | ccgcagagtt | gcaggatgcc | 1140 |
| acgcccgctg | cgctggtggc | acatgtgacc | tcgcgcaaat | gctacggtcc | gagcgcgacc | 1200 |
| agtgaaaaat | gtccgggtaa | cgctctggaa | aaaggcggaa | aaggatcgat | taccgaacag | 1260 |
| ctgcttaacg | ctcgtgccga | cgttacgctt | ggcggcggcg | caaaaacctt | tgctgaaacg | 1320 |
| gcaaccgctg | gtgaatggca | gggaaaaacg | ctgcgtgaac | aggcacaggc | gcgtggttat | 1380 |
| cagttggtga | gcgatgctgc | tcactgaac | tcggtgacgg | aagcgaatca | gcaaaaaccc | 1440 |
| ctgcttggcc | tgtttgctga | cggcaatatg | ccagtgcgct | ggctaggacc | gaaagcaacg | 1500 |
| taccatggca | atatcgataa | gcccgcagtc | acctgtacgc | caaatccgca | acgtaatgac | 1560 |
| agtgtaccaa | ccctggcgca | gatgaccgac | aaagccattg | aattgttgag | taaaaatgag | 1620 |
| aaaggctttt | tcctgcaagt | tgaaggtgcg | tcaatcgata | acaggatca | tgctgcgaat | 1680 |
| ccttgtgggc | aaattggcga | gacggtcgat | ctcgatgaag | ccgtacaacg | ggcgctggag | 1740 |
| ttcgctaaaa | aggagggtaa | cacgctggtc | atagtcaccg | ctgatcacgc | ccacgccagc | 1800 |
| cagattgttg | cgccggatac | caaagctccg | ggcctcaccc | aggcgctaaa | taccaaagat | 1860 |
| ggcgcagtga | tggtgatgag | ttacgggaac | tccgaagagg | attcacaaga | acataccggc | 1920 |
| agtcagttgc | gtattgcggc | gtatggcccg | catgccgcca | atgttgttgg | actgaccgac | 1980 |
| cagaccgatc | tcttctacac | catgaaagcc | gctctggggc | tgaaaggcgc | gccggactat | 2040 |
| aaagatgacg | atgacaaagg | cgcgccgcac | catcatcacc | atcac | | 2085 |

<210> SEQ ID NO 20
<211> LENGTH: 645
<212> TYPE: DNA
<213> ORGANISM: Artificial Sequence
<220> FEATURE:
<223> OTHER INFORMATION: A synthetic light chain of the Fab region of
      the anti-Ambra-1 antibody

<400> SEQUENCE: 20

```
gatatcgtgc tgacccagcc gccgagcgtg agcggtgcac cgggccagcg cgtgaccatt      60
agctgtagcg gcagcagcag caacattggt tacaactacg tgtactggta ccagcagctg     120
ccgggcacgg cgccgaaact gctgatctac gaaaacaaca aacgcccgag cggcgtgccg     180
gatcgcttta gcggatccaa aagcggcacc agcgccagcc tggcgattac cggcctgcaa     240
gcagaagacg aagcggatta ttactgctct tcttgggact ctcattctaa ctcttacgtg     300
tttggcggcg gcacgaagtt aaccgttctt ggccagccga agccgccccc aagcgtgacc     360
ctgtttccgc cgagcagcga agaactgcaa gccaacaaag ccaccctggt ttgcctgatc     420
agcgattttt atccgggtgc cgtgaccgtg gcctggaaag ccgatagcag cccggtgaaa     480
gccggcgtgg aaaccaccac cccgagcaaa cagagcaaca caaatatgc cgccagcagc      540 tatctgagcc tgaccccgga acagtggaaa agccatcgca gctatagttg tcaagtgacc     600
catgaaggca gcaccgtgga aaaaaccgtg gccccgaccg aggcc                     645
```

<210> SEQ ID NO 21
<211> LENGTH: 1298
<212> TYPE: PRT
<213> ORGANISM: Homo sapiens

<400> SEQUENCE: 21

```
Met Lys Val Val Pro Glu Lys Asn Ala Val Arg Ile Leu Trp Gly Arg
1               5                   10                  15

Glu Arg Gly Ala Arg Ala Met Gly Ala Gln Arg Leu Leu Gln Glu Leu
            20                  25                  30

Val Glu Asp Lys Thr Arg Trp Met Lys Trp Glu Gly Lys Arg Val Glu
        35                  40                  45

Leu Pro Asp Ser Pro Arg Ser Thr Phe Leu Leu Ala Phe Ser Pro Asp
    50                  55                  60

Arg Thr Leu Leu Ala Ser Thr His Val Asn His Asn Ile Tyr Ile Thr
65                  70                  75                  80

Glu Val Lys Thr Gly Lys Cys Val His Ser Leu Ile Gly His Arg Arg
                85                  90                  95

Thr Pro Trp Cys Val Thr Phe His Pro Thr Ile Ser Gly Leu Ile Ala
            100                 105                 110

Ser Gly Cys Leu Asp Gly Glu Val Arg Ile Trp Asp Leu His Gly Gly
        115                 120                 125

Ser Glu Ser Trp Phe Thr Asp Ser Asn Asn Ala Ile Ala Ser Leu Ala
    130                 135                 140

Phe His Pro Thr Ala Gln Leu Leu Leu Ile Ala Thr Ala Asn Glu Ile
145                 150                 155                 160

His Phe Trp Asp Trp Ser Arg Arg Glu Pro Phe Ala Val Val Lys Thr
                165                 170                 175

Ala Ser Glu Met Glu Arg Val Arg Leu Val Arg Phe Asp Pro Leu Gly
            180                 185                 190

His Tyr Leu Leu Thr Ala Ile Val Asn Pro Ser Asn Gln Gln Gly Asp
        195                 200                 205
```

```
Asp Glu Pro Glu Ile Pro Ile Asp Gly Thr Glu Leu Ser His Tyr Arg
    210                 215                 220
Gln Arg Ala Leu Leu Gln Ser Gln Pro Val Arg Arg Thr Pro Leu Leu
225                 230                 235                 240
His Asn Phe Leu His Met Leu Ser Ser Arg Ser Ser Gly Ile Gln Val
                245                 250                 255
Gly Glu Gln Ser Thr Val Gln Asp Ser Ala Thr Pro Ser Pro Pro Pro
            260                 265                 270
Pro Pro Pro Gln Pro Ser Thr Glu Arg Pro Arg Thr Ser Ala Tyr Ile
        275                 280                 285
Arg Leu Arg Gln Arg Val Ser Tyr Pro Thr Ala Glu Cys Cys Gln His
290                 295                 300
Leu Gly Ile Leu Cys Leu Cys Ser Arg Cys Ser Gly Thr Arg Val Pro
305                 310                 315                 320
Ser Leu Leu Pro His Gln Asp Ser Val Pro Ala Ser Ala Arg Ala
                325                 330                 335
Thr Thr Pro Ser Phe Ser Phe Val Gln Thr Glu Pro Phe His Pro
                340                 345                 350
Glu Gln Ala Ser Ser Thr Gln Gln Asp Gln Gly Leu Leu Asn Arg Pro
            355                 360                 365
Ser Ala Phe Ser Thr Val Gln Ser Ser Thr Ala Gly Asn Thr Leu Arg
370                 375                 380
Asn Leu Ser Leu Gly Pro Thr Arg Arg Ser Leu Gly Gly Pro Leu Ser
385                 390                 395                 400
Ser His Pro Ser Arg Tyr His Arg Glu Ile Ala Pro Gly Leu Thr Gly
                405                 410                 415
Ser Glu Trp Thr Arg Thr Val Leu Ser Leu Asn Ser Arg Ser Glu Ala
            420                 425                 430
Glu Ser Met Pro Pro Arg Thr Ser Ala Ser Ser Val Ser Leu Leu
        435                 440                 445
Ser Val Leu Arg Gln Gln Glu Gly Gly Ser Gln Ala Ser Val Tyr Thr
450                 455                 460
Ser Ala Thr Glu Gly Arg Gly Phe Pro Ala Ser Gly Leu Ala Thr Glu
465                 470                 475                 480
Ser Asp Gly Gly Asn Gly Ser Ser Gln Asn Asn Ser Gly Ser Ile Arg
                485                 490                 495
His Glu Leu Gln Cys Asp Leu Arg Arg Phe Phe Leu Glu Tyr Asp Arg
            500                 505                 510
Leu Gln Glu Leu Asp Gln Ser Leu Ser Gly Glu Ala Pro Gln Thr Gln
        515                 520                 525
Gln Ala Gln Glu Met Leu Asn Asn Ile Glu Ser Glu Arg Pro Gly
    530                 535                 540
Pro Ser His Gln Pro Thr Pro His Ser Ser Glu Asn Asn Ser Asn Leu
545                 550                 555                 560
Ser Arg Gly His Leu Asn Arg Cys Arg Ala Cys His Asn Leu Leu Thr
                565                 570                 575
Phe Asn Asn Asp Thr Leu Arg Trp Glu Arg Thr Thr Pro Asn Tyr Ser
            580                 585                 590
Ser Gly Glu Ala Ser Ser Ser Trp Gln Val Pro Ser Ser Phe Glu Ser
        595                 600                 605
Val Pro Ser Ser Gly Ser Gln Leu Pro Pro Leu Glu Arg Thr Glu Gly
    610                 615                 620
Gln Thr Pro Ser Ser Ser Arg Leu Glu Leu Ser Ser Ser Ala Ser Pro
```

```
            625                 630                 635                 640
Gln Glu Glu Arg Thr Val Gly Val Ala Phe Asn Gln Glu Thr Gly His
                645                 650                 655

Trp Glu Arg Ile Tyr Thr Gln Ser Ser Arg Ser Gly Thr Val Ser Gln
                660                 665                 670

Glu Ala Leu His Gln Asp Met Pro Glu Glu Ser Ser Glu Glu Asp Ser
                675                 680                 685

Leu Arg Arg Arg Leu Leu Glu Ser Ser Leu Ile Ser Leu Ser Arg Tyr
            690                 695                 700

Asp Gly Ala Gly Ser Arg Glu His Pro Ile Tyr Pro Asp Pro Ala Arg
705                 710                 715                 720

Leu Ser Pro Ala Ala Tyr Ala Gln Arg Met Ile Gln Tyr Leu Ser
                725                 730                 735

Arg Arg Asp Ser Ile Arg Gln Arg Ser Met Arg Tyr Gln Gln Asn Arg
                740                 745                 750

Leu Arg Ser Ser Thr Ser Ser Ser Ser Asp Asn Gln Gly Pro Ser
            755                 760                 765

Val Glu Gly Thr Asp Leu Glu Phe Glu Asp Phe Glu Asp Asn Gly Asp
        770                 775                 780

Arg Ser Arg His Arg Ala Pro Arg Asn Ala Arg Met Ser Ala Pro Ser
785                 790                 795                 800

Leu Gly Arg Phe Val Pro Arg Phe Leu Leu Pro Glu Tyr Leu Pro
                805                 810                 815

Tyr Ala Gly Ile Phe His Glu Arg Gly Gln Pro Gly Leu Ala Thr His
                820                 825                 830

Ser Ser Val Asn Arg Val Leu Ala Gly Ala Val Ile Gly Asp Gly Gln
            835                 840                 845

Ser Ala Val Ala Ser Asn Ile Ala Asn Thr Thr Tyr Arg Leu Gln Trp
        850                 855                 860

Trp Asp Phe Thr Lys Phe Asp Leu Pro Glu Ile Ser Asn Ala Ser Val
865                 870                 875                 880

Asn Val Leu Val Gln Asn Cys Lys Ile Tyr Asn Asp Ala Ser Cys Asp
                885                 890                 895

Ile Ser Ala Asp Gly Gln Leu Leu Ala Ala Phe Ile Pro Ser Ser Gln
                900                 905                 910

Arg Gly Phe Pro Asp Glu Gly Ile Leu Ala Val Tyr Ser Leu Ala Pro
            915                 920                 925

His Asn Leu Gly Glu Met Leu Tyr Thr Lys Arg Phe Gly Pro Asn Ala
        930                 935                 940

Ile Ser Val Ser Leu Ser Pro Met Gly Arg Tyr Val Met Val Gly Leu
945                 950                 955                 960

Ala Ser Arg Arg Ile Leu Leu His Pro Ser Thr Glu His Met Val Ala
                965                 970                 975

Gln Val Phe Arg Leu Gln Gln Ala His Gly Gly Glu Thr Ser Met Arg
                980                 985                 990

Arg Val Phe Asn Val Leu Tyr Pro  Met Pro Ala Asp Gln Arg Arg His
            995                 1000                1005

Val Ser  Ile Asn Ser Ala Arg  Trp Leu Pro Glu Pro  Gly Leu Gly
    1010                1015                1020

Leu Ala  Tyr Gly Thr Asn Lys  Gly Asp Leu Val Ile  Cys Arg Pro
    1025                1030                1035

Glu Ala  Leu Asn Ser Gly Val  Glu Tyr Tyr Trp Asp  Gln Leu Asn
    1040                1045                1050
```

```
Glu Thr Val Phe Thr Val His Ser Asn Ser Arg Ser Ser Glu Arg
    1055                1060                1065

Pro Gly Thr Ser Arg Ala Thr Trp Arg Thr Asp Arg Asp Met Gly
    1070                1075                1080

Leu Met Asn Ala Ile Gly Leu Gln Pro Arg Asn Pro Ala Thr Ser
    1085                1090                1095

Val Thr Ser Gln Gly Thr Gln Thr Leu Ala Leu Gln Leu Gln Asn
    1100                1105                1110

Ala Glu Thr Gln Thr Glu Arg Glu Val Pro Glu Pro Gly Thr Ala
    1115                1120                1125

Ala Ser Gly Pro Gly Glu Gly Glu Gly Ser Glu Tyr Gly Ala Ser
    1130                1135                1140

Gly Glu Asp Ala Leu Ser Arg Ile Gln Arg Leu Met Ala Glu Gly
    1145                1150                1155

Gly Met Thr Ala Val Val Gln Arg Glu Gln Ser Thr Thr Met Ala
    1160                1165                1170

Ser Met Gly Gly Phe Gly Asn Asn Ile Ile Val Ser His Arg Ile
    1175                1180                1185

His Arg Ser Ser Gln Thr Gly Thr Glu Pro Gly Ala Ala His Thr
    1190                1195                1200

Ser Ser Pro Gln Pro Ser Thr Ser Arg Gly Leu Leu Pro Glu Ala
    1205                1210                1215

Gly Gln Leu Ala Glu Arg Gly Leu Ser Pro Arg Thr Ala Ser Trp
    1220                1225                1230

Asp Gln Pro Gly Thr Pro Gly Arg Glu Pro Thr Gln Pro Thr Leu
    1235                1240                1245

Pro Ser Ser Ser Pro Val Pro Ile Pro Val Ser Leu Pro Ser Ala
    1250                1255                1260

Glu Gly Pro Thr Leu His Cys Glu Leu Thr Asn Asn His Leu
    1265                1270                1275

Leu Asp Gly Gly Ser Ser Arg Gly Asp Ala Ala Gly Pro Arg Gly
    1280                1285                1290

Glu Pro Arg Asn Arg
    1295

<210> SEQ ID NO 22
<211> LENGTH: 5
<212> TYPE: PRT
<213> ORGANISM: Artificial Sequence
<220> FEATURE:
<223> OTHER INFORMATION: A synthetic HCDR1 of the anti-Loricrin antibody

<400> SEQUENCE: 22

Asp Tyr Tyr Ile His
1               5

<210> SEQ ID NO 23
<211> LENGTH: 17
<212> TYPE: PRT
<213> ORGANISM: Artificial Sequence
<220> FEATURE:
<223> OTHER INFORMATION: A synthetic HCDR2 of the anti-Loricrin antibody

<400> SEQUENCE: 23

Val Ile Ser Pro Asn Ser Gly Lys Thr Asn Tyr Ala Gln Lys Phe Gln
1               5                   10                  15

Gly
```

<210> SEQ ID NO 24
<211> LENGTH: 11
<212> TYPE: PRT
<213> ORGANISM: Artificial Sequence
<220> FEATURE:
<223> OTHER INFORMATION: A synthetic HCDR3 of the anti-Loricrin antibody

<400> SEQUENCE: 24

Asp Leu Tyr Pro Asp Ser Ser Ala Phe Asp Ile
1               5                   10

<210> SEQ ID NO 25
<211> LENGTH: 11
<212> TYPE: PRT
<213> ORGANISM: Artificial Sequence
<220> FEATURE:
<223> OTHER INFORMATION: A synthetic LCDR1 of the anti-Loricrin antibody

<400> SEQUENCE: 25

Ser Gly Asp Asn Leu Gly Asp Lys Tyr Ala His
1               5                   10

<210> SEQ ID NO 26
<211> LENGTH: 7
<212> TYPE: PRT
<213> ORGANISM: Artificial Sequence
<220> FEATURE:
<223> OTHER INFORMATION: A synthetic LCDR2 of the anti-Loricrin antibody

<400> SEQUENCE: 26

Asp Asp Asn Glu Arg Pro Ser
1               5

<210> SEQ ID NO 27
<211> LENGTH: 9
<212> TYPE: PRT
<213> ORGANISM: Artificial Sequence
<220> FEATURE:
<223> OTHER INFORMATION: A synthetic LCDR3 of the anti-Loricrin antibody

<400> SEQUENCE: 27

Gln Ser Tyr Asp Ser Gly Asn Arg Val
1               5

<210> SEQ ID NO 28
<211> LENGTH: 30
<212> TYPE: PRT
<213> ORGANISM: Artificial Sequence
<220> FEATURE:
<223> OTHER INFORMATION: A synthetic HCFR1 of the anti-Loricrin antibody

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn
            20                  25                  30

<210> SEQ ID NO 29
<211> LENGTH: 14
<212> TYPE: PRT
<213> ORGANISM: Artificial Sequence
<220> FEATURE:
<223> OTHER INFORMATION: A synthetic HCFR2 of the anti-Loricrin antibody

<400> SEQUENCE: 29

Trp Val Arg Gln Ala Pro Gly Gln Gly Leu Glu Trp Met Gly
1               5                   10

<210> SEQ ID NO 30
<211> LENGTH: 32
<212> TYPE: PRT
<213> ORGANISM: Artificial Sequence
<220> FEATURE:
<223> OTHER INFORMATION: A synthetic HCFR3 of the anti-Loricrin antibody

<400> SEQUENCE: 30

Arg Val Thr Met Thr Arg Asp Thr Ser Ile Ser Thr Ala Tyr Met Glu
1               5                   10                  15

Leu Ser Arg Leu Arg Ser Glu Asp Thr Ala Val Tyr Tyr Cys Ala Arg
            20                  25                  30

<210> SEQ ID NO 31
<211> LENGTH: 11
<212> TYPE: PRT
<213> ORGANISM: Artificial Sequence
<220> FEATURE:
<223> OTHER INFORMATION: A synthetic HCFR4 of the anti-Loricrin antibody

<400> SEQUENCE: 31

Trp Gly Gln Gly Thr Leu Val Thr Val Ser Ser
1               5                   10

<210> SEQ ID NO 32
<211> LENGTH: 22
<212> TYPE: PRT
<213> ORGANISM: Artificial Sequence
<220> FEATURE:
<223> OTHER INFORMATION: A synthetic LCFR1 of the anti-Loricrin antibody

<400> SEQUENCE: 32

Asp Ile Glu Leu Thr Gln Pro Pro Ser Val Ser Val Ser Pro Gly Gln
1               5                   10                  15

Thr Ala Ser Ile Thr Cys
            20

<210> SEQ ID NO 33
<211> LENGTH: 15
<212> TYPE: PRT
<213> ORGANISM: Artificial Sequence
<220> FEATURE:
<223> OTHER INFORMATION: A synthetic LCFR2 of the anti-Loricrin antibody

<400> SEQUENCE: 33

Trp Tyr Gln Gln Lys Pro Gly Gln Ala Pro Val Leu Val Ile Tyr
1               5                   10                  15

<210> SEQ ID NO 34
<211> LENGTH: 32
<212> TYPE: PRT
<213> ORGANISM: Artificial Sequence
<220> FEATURE:
<223> OTHER INFORMATION: A synthetic LCFR3 of the anti-Loricrin antibody

<400> SEQUENCE: 34

Gly Ile Pro Glu Arg Phe Ser Gly Ser Asn Ser Gly Asn Thr Ala Thr
1               5                   10                  15

Leu Thr Ile Ser Gly Thr Gln Ala Glu Asp Glu Ala Asp Tyr Tyr Cys
            20                  25                  30

<210> SEQ ID NO 35

```
<211> LENGTH: 12
<212> TYPE: PRT
<213> ORGANISM: Artificial Sequence
<220> FEATURE:
<223> OTHER INFORMATION: A synthetic LCFR4 of the anti-Loricrin antibody

<400> SEQUENCE: 35

Phe Gly Gly Gly Thr Lys Leu Thr Val Leu Gly Gln
1               5                   10

<210> SEQ ID NO 36
<211> LENGTH: 120
<212> TYPE: PRT
<213> ORGANISM: Artificial Sequence
<220> FEATURE:
<223> OTHER INFORMATION: A synthetic VH domain of the anti-Loricrin
      antibody

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asp Tyr
            20                  25                  30

Tyr Ile His Trp Val Arg Gln Ala Pro Gly Gln Gly Leu Glu Trp Met
        35                  40                  45

Gly Val Ile Ser Pro Asn Ser Gly Lys Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Asp Leu Tyr Pro Asp Ser Ser Ala Phe Asp Ile Trp Gly Gln
            100                 105                 110

Gly Thr Leu Val Thr Val Ser Ser
        115                 120

<210> SEQ ID NO 37
<211> LENGTH: 108
<212> TYPE: PRT
<213> ORGANISM: Artificial Sequence
<220> FEATURE:
<223> OTHER INFORMATION: A synthetic VL domain of the anti-Loricrin
      antibody

<400> SEQUENCE: 37

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Asp Lys Tyr Ala
            20                  25                  30

His Trp Tyr Gln Gln Lys Pro Gly Gln Ala Pro Val Leu Val Ile Tyr
        35                  40                  45

Asp Asp Asn Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Gly Asn Arg Val
                85                  90                  95

Phe Gly Gly Gly Thr Lys Leu Thr Val Leu Gly Gln
            100                 105
```

```
<210> SEQ ID NO 38
<211> LENGTH: 222
<212> TYPE: PRT
<213> ORGANISM: Artificial Sequence
<220> FEATURE:
<223> OTHER INFORMATION: A synthetic Fd chain (VH domain and constant
      domain) of the Fab region of the anti-Loricrin antibody

<400> SEQUENCE: 38

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Asp Tyr
            20                  25                  30

Tyr Ile His Trp Val Arg Gln Ala Pro Gly Gln Gly Leu Glu Trp Met
        35                  40                  45

Gly Val Ile Ser Pro Asn Ser Gly Lys Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Glu Asp Thr Ala Val Tyr Tyr Cys
                85                  90                  95

Ala Arg Asp Leu Tyr Pro Asp Ser Ser Ala Phe Asp Ile Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser
    210                 215                 220

<210> SEQ ID NO 39
<211> LENGTH: 211
<212> TYPE: PRT
<213> ORGANISM: Artificial Sequence
<220> FEATURE:
<223> OTHER INFORMATION: A synthetic light chain (VL domain and constant
      domain) of the Fab region of the anti-Loricrin antibody

<400> SEQUENCE: 39

Asp Ile Glu Leu Thr Gln Pro Pro Ser Val Ser Val Ser Pro Gly Gln
1               5                   10                  15

Thr Ala Ser Ile Thr Cys Ser Gly Asp Asn Leu Gly Asp Lys Tyr Ala
            20                  25                  30

His Trp Tyr Gln Gln Lys Pro Gly Gln Ala Pro Val Leu Val Ile Tyr
        35                  40                  45

Asp Asp Asn Glu Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Glu
65                  70                  75                  80

Asp Glu Ala Asp Tyr Tyr Cys Gln Ser Tyr Asp Ser Gly Asn Arg Val
```

```
                    85                  90                  95
Phe Gly Gly Thr Lys Leu Thr Val Leu Gly Gln Pro Lys Ala Ala
                100                 105                 110

Pro Ser Val Thr Leu Phe Pro Pro Ser Ser Glu Glu Leu Gln Ala Asn
                115                 120                 125

Lys Ala Thr Leu Val Cys Leu Ile Ser Asp Phe Tyr Pro Gly Ala Val
            130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
                195                 200                 205

Thr Glu Ala
        210

<210> SEQ ID NO 40
<211> LENGTH: 2079
<212> TYPE: DNA
<213> ORGANISM: Artificial Sequence
<220> FEATURE:
<223> OTHER INFORMATION: A synthetic Fd chain of the Fab region and tags
      of the anti-Loricrin antibody

<400> SEQUENCE: 40
caggtgcaat tggtgcagag cggtgcggaa gtgaaaaaac cgggtgccag cgtgaaagtt        60
agctgcaaag cgtccggata ccttcaacga ctactaca tccattgggt gcgccaggcc        120
ccgggccagg gcctcgagtg gatgggcgtt atctctccga actctggcaa acgaactac        180 gcgcagaaat tcagggccg gtgaccatg acccgtgata ccagcattag caccgcgtat        240
atggaactga ccgtctgcg tagcgaagat acggccgtgt attattgcgc gcgtgacctg        300
tacccggact cttctgcttt cgatatctgg ggccaaggca ccctggtgac tgttagctca        360
gcgtcgacca aaggcccgag cgtgtttccg ctggccccga gcagcaaaag caccagcggc        420
ggcaccgccg cactgggctg cctggtgaaa gattatttcc cggaaccagt gaccgtgagc        480
tggaacagcg gtgccctgac cagcggcgtg cataccttc cggcggtgct gcaaagcagc        540
ggcctgtata gcctgagcag cgttgtgacc gtgccgagca gcagcctggg cacccagacc        600
tatatttgca acgtcaacca taaaccgagc aacaccaaag tcgataaaaa agtcgaaccg        660
aaaagcgaat tcaaggctga atgcctgtt ctggaaaaacc gggctgctca gggcgatatt        720 actcacccg gcgtgctcg ccgtttaacg ggtgatcaga ctgccgctct gcgtgattct        780
cttagcgata aacctgcaaa aaatattatt ttgctgattg gcgatgggat ggggactcg        840 gaaattactg ccgcacgtaa ttatgccgaa ggtgcgggcg gctttttta aggtatagat        900 gccttaccgc ttaccgggca atacactcac tatgcgctga atagaaaaac cggcaaaccg        960
gactacgtca ccagctcggc tgcatcagca accgcctggt caaccggtgt caaaaccta       1020 aacggcgcgc tgggcgtcga tattcacgaa aaagatcacc caacgattct ggaaatggca       1080
aaagccgcag gtctggcgac cggtaacgtt tctaccgcag agttgcagga tgccacgccc       1140
gctgcgctgg tggcacatgt gacctcgcgc aaatgctacg tccgagcgc gaccagtgaa       1200 aaatgtccgg gtaacgctct ggaaaaaggc ggaaaaggat cgattaccga acagctgctt       1260
```

```
aacgctcgtg ccgacgttac gcttggcggc ggcgcaaaaa cctttgctga aacggcaacc    1320
gctggtgaat ggcagggaaa aacgctgcgt gaacaggcac aggcgcgtgg ttatcagttg    1380
gtgagcgatg ctgcctcact gaactcggtg acggaagcga atcagcaaaa accctgcttt   1440
ggcctgtttg ctgacggcaa tatgccagtc gctggctag gaccgaaagc aacgtaccat    1500
ggcaatatcg ataagcccgc agtcacctgt acgccaaatc cgcaacgtaa tgacagtgta   1560
ccaaccctgg cgcagatgac cgacaaagcc attgaattgt tgagtaaaaa tgagaaaggc   1620 ttttcctgc aagttgaagg tgcgtcaatc gataaacagg atcatgctgc gaatccttgt    1680
gggcaaattg gcgagacggt cgatctcgat gaagccgtac aacgggcgct ggagttcgct   1740
aaaaaggagg gtaacacgct ggtcatagtc accgctgatc acgcccacgc cagccagatt   1800
gttgcgccgg ataccaaagc tccgggcctc acccaggcgc taaataccaa agatggcgca   1860
gtgatggtga tgagttacgg gaactccgaa gaggattcac aagaacatac cggcagtcag   1920
ttgcgtattg cggcgtatgg cccgcatgcc gccaatgttg ttggactgac cgaccagacc   1980
gatctcttct acaccatgaa agccgctctg ggctgaaag gcgcgccgga ctataaagat    2040
gacgatgaca aaggcgcgcc gcaccatcat caccatcac                          2079

<210> SEQ ID NO 41
<211> LENGTH: 633
<212> TYPE: DNA
<213> ORGANISM: Artificial Sequence
<220> FEATURE:
<223> OTHER INFORMATION: A synthetic the light chain of the Fab region
      of the anti-Loricrin antibody

<400> SEQUENCE: 41
gatatcgaac tgacccagcc gccgagcgtg agcgtgagcc cgggccagac cgcgagcatt     60
acctgtagcg gcgataacct gggtgacaaa tacgctcatt ggtaccagca gaaaccgggc    120
caggcgccgg tgctggtgat ctacgacgac aacgaacgtc cgagcggcat cccggaacgt    180
tttagcggat ccaacagcgg caacaccgcg accctgacca ttagcggcac ccaggcggaa    240
gacgaagcgg attattactg ccagtcttac gactctggta acgtgtgtt tggcggcggc     300 acgaagttaa ccgttcttgg ccagccgaaa gccgccccaa gcgtgaccct gtttccgccg    360
agcagcgaag aactgcaagc caacaaagcc accctggttt gcctgatcag cgattttat     420 ccgggtgccg tgaccgtggc ctggaaagcc gatagcagcc cggtgaaagc cggcgtggaa    480
accaccaccc cgagcaaaca gagcaacaac aaatatgccg ccagcagcta tctgagcctg    540 accccgaac agtggaaaag ccatcgcagc tatagttgtc aagtgaccca tgaaggcagc     600
accgtggaaa aaccgtggc cccgaccgag gcc                                   633

<210> SEQ ID NO 42
<211> LENGTH: 312
<212> TYPE: PRT
<213> ORGANISM: Homo sapiens

<400> SEQUENCE: 42

Met Ser Tyr Gln Lys Lys Gln Pro Thr Pro Gln Pro Pro Val Asp Cys
1               5                   10                  15

Val Lys Thr Ser Gly Gly Gly Gly Gly Gly Gly Ser Gly Gly Gly
            20                  25                  30

Gly Cys Gly Phe Phe Gly Gly Gly Ser Gly Gly Gly Ser Ser Gly
        35                  40                  45

Ser Gly Cys Gly Tyr Ser Gly Gly Gly Gly Tyr Ser Gly Gly Gly Cys
```

```
                50             55              60
Gly Gly Gly Ser Ser Gly Gly Gly Gly Ile Gly Cys
 65              70              75              80

Gly Gly Gly Ser Gly Gly Ser Val Lys Tyr Ser Gly Gly Ser
                 85              90              95

Ser Gly Gly Gly Ser Gly Cys Phe Ser Gly Gly Gly Ser Gly
                100             105             110

Cys Phe Ser Gly Gly Gly Ser Ser Gly Gly Ser Gly Cys
         115             120             125

Phe Ser Gly Gly Gly Gly Ser Ser Gly Gly Ser Gly Cys Phe
         130             135             140

Ser Gly Gly Gly Gly Phe Ser Gly Gln Ala Val Gln Cys Gln Ser
145             150             155             160

Tyr Gly Gly Val Ser Ser Gly Gly Ser Ser Gly Gly Ser Gly Cys
                 165             170             175

Phe Ser Gly Gly Gly Gly Ser Val Cys Gly Tyr Ser Gly Gly
                 180             185             190

Gly Ser Gly Cys Gly Gly Gly Ser Ser Gly Gly Ser Gly Gly Tyr
         195             200             205

Val Ser Ser Gln Gln Val Thr Gln Thr Ser Cys Ala Pro Gln Pro Ser
 210             215             220

Tyr Gly Gly Gly Ser Ser Gly Gly Gly Ser Gly Gly Ser Gly Cys
225             230             235             240

Phe Ser Ser Gly Gly Gly Gly Ser Ser Gly Cys Gly Gly Gly Ser
                 245             250             255

Ser Gly Ile Gly Ser Gly Cys Ile Ile Ser Gly Gly Gly Ser Val Cys
         260             265             270

Gly Gly Gly Ser Ser Gly Gly Gly Gly Ser Ser Val Gly Gly
         275             280             285

Ser Gly Ser Gly Lys Gly Val Pro Ile Cys His Gln Thr Gln Gln Lys
         290             295             300

Gln Ala Pro Thr Trp Pro Ser Lys
305             310

<210> SEQ ID NO 43
<211> LENGTH: 8
<212> TYPE: PRT
<213> ORGANISM: Artificial Sequence
<220> FEATURE:
<223> OTHER INFORMATION: A synthetic exemplary epitope tag

<400> SEQUENCE: 43

Asp Tyr Lys Asp Asp Asp Asp Lys
 1               5

<210> SEQ ID NO 44
<211> LENGTH: 14
<212> TYPE: PRT
<213> ORGANISM: Artificial Sequence
<220> FEATURE:
<223> OTHER INFORMATION: A synthetic exemplary epitope tag

<400> SEQUENCE: 44

Gly Lys Pro Ile Pro Asn Pro Leu Leu Gly Leu Asp Ser Thr
 1               5                  10

<210> SEQ ID NO 45
<211> LENGTH: 8
```

```
<212> TYPE: PRT
<213> ORGANISM: Artificial Sequence
<220> FEATURE:
<223> OTHER INFORMATION: A synthetic exemplary epitope tag

<400> SEQUENCE: 45

Trp Ser His Pro Gln Phe Glu Lys
1               5

<210> SEQ ID NO 46
<211> LENGTH: 19
<212> TYPE: PRT
<213> ORGANISM: Artificial Sequence
<220> FEATURE:
<223> OTHER INFORMATION: A synthetic peptide to which anti-Ambra-1
      antibodies were raised

<400> SEQUENCE: 46

Cys Gly Gly Ser Ser Arg Gly Asp Ala Ala Gly Pro Arg Gly Glu Pro
1               5                   10                  15

Arg Asn Arg

<210> SEQ ID NO 47
<211> LENGTH: 6
<212> TYPE: PRT
<213> ORGANISM: Artificial Sequence
<220> FEATURE:
<223> OTHER INFORMATION: A synthetic His6 tag

<400> SEQUENCE: 47

His His His His His His
1               5

<210> SEQ ID NO 48
<211> LENGTH: 41
<212> TYPE: PRT
<213> ORGANISM: Artificial Sequence
<220> FEATURE:
<223> OTHER INFORMATION: A synthetic Ambra-1 C-terminal sequence used
      for replacement analysis in epitope mapping

<400> SEQUENCE: 48

Val Ser Leu Pro Ser Ala Glu Gly Pro Thr Leu His Cys Glu Leu Thr
1               5                   10                  15

Asn Asn Asn His Leu Leu Asp Gly Gly Ser Ser Arg Gly Asp Ala Ala
            20                  25                  30

Gly Pro Arg Gly Glu Pro Arg Asn Arg
        35                  40

<210> SEQ ID NO 49
<211> LENGTH: 19
<212> TYPE: PRT
<213> ORGANISM: Artificial Sequence
<220> FEATURE:
<223> OTHER INFORMATION: A synthetic REPNET epitope of the Anti-Ambra-1
      antibodies

<400> SEQUENCE: 49

Asp Gly Gly Ser Ser Arg Gly Asp Ala Ala Gly Pro Arg Gly Glu Pro
1               5                   10                  15

Arg Asn Arg

<210> SEQ ID NO 50
<211> LENGTH: 9
<212> TYPE: PRT
```

```
<213> ORGANISM: Artificial Sequence
<220> FEATURE:
<223> OTHER INFORMATION: A synthetic LIN epitope of the Anti-Ambra-1
      antibodies

<400> SEQUENCE: 50

His Leu Leu Asp Gly Gly Ser Ser Arg
1               5

<210> SEQ ID NO 51
<211> LENGTH: 10
<212> TYPE: PRT
<213> ORGANISM: Artificial Sequence
<220> FEATURE:
<223> OTHER INFORMATION: A synthetic LOOP epitope of the Anti-Ambra-1
      antibodies

<400> SEQUENCE: 51

Asn His Leu Leu Asp Gly Gly Ser Ser Arg
1               5                   10

<210> SEQ ID NO 52
<211> LENGTH: 4
<212> TYPE: PRT
<213> ORGANISM: Artificial Sequence
<220> FEATURE:
<223> OTHER INFORMATION: A synthetic core epitope of the Anti-Ambra-1
      antibodies

<400> SEQUENCE: 52

Glu Pro Arg Asn
1

<210> SEQ ID NO 53
<211> LENGTH: 3
<212> TYPE: PRT
<213> ORGANISM: Artificial Sequence
<220> FEATURE:
<223> OTHER INFORMATION: A synthetic core epitope of the Anti-Ambra-1
      antibodies

<400> SEQUENCE: 53

Glu Pro Arg
1

<210> SEQ ID NO 54
<211> LENGTH: 19
<212> TYPE: PRT
<213> ORGANISM: Artificial Sequence
<220> FEATURE:
<223> OTHER INFORMATION: A synthetic epitope of the Anti- Loricrin
      antibodies

<400> SEQUENCE: 54

Ser Tyr Gln Lys Lys Gln Pro Thr Pro Gly Pro Pro Val Asp Cys Val
1               5                   10                  15

Lys Thr Ser

<210> SEQ ID NO 55
<211> LENGTH: 19
<212> TYPE: PRT
<213> ORGANISM: Artificial Sequence
<220> FEATURE:
<223> OTHER INFORMATION: A synthetic epitope of the Anti- Loricrin
      antibodies

<400> SEQUENCE: 55
```

```
Gly Gly Gly Gly Ile Gly Gly Pro Gly Gly Ser Gly Gly Ser Val
1               5                   10                  15

Lys Tyr Ser

<210> SEQ ID NO 56
<211> LENGTH: 15
<212> TYPE: PRT
<213> ORGANISM: Artificial Sequence
<220> FEATURE:
<223> OTHER INFORMATION: A synthetic epitope of the Anti- Loricrin
      antibodies

<400> SEQUENCE: 56

Gly Ser Ser Gly Gly Gly Ser Gly Cys Phe Ser Ser Gly Gly Gly
1               5                   10                  15

<210> SEQ ID NO 57
<211> LENGTH: 19
<212> TYPE: PRT
<213> ORGANISM: Artificial Sequence
<220> FEATURE:
<223> OTHER INFORMATION: A synthetic epitope of the Anti- Loricrin
      antibodies

<400> SEQUENCE: 57

Gly Ile Gly Ser Gly Cys Ile Ile Ser Gly Gly Gly Ser Val Cys Gly
1               5                   10                  15

Gly Gly Ser

<210> SEQ ID NO 58
<211> LENGTH: 19
<212> TYPE: PRT
<213> ORGANISM: Artificial Sequence
<220> FEATURE:
<223> OTHER INFORMATION: A synthetic epitope of the Anti- Loricrin
      antibodies

<400> SEQUENCE: 58

Gly Ser Ser Gly Gly Gly Gly Gly Gly Ser Ser Val Gly Gly Ser Gly
1               5                   10                  15

Ser Gly Lys

<210> SEQ ID NO 59
<211> LENGTH: 11
<212> TYPE: PRT
<213> ORGANISM: Artificial Sequence
<220> FEATURE:
<223> OTHER INFORMATION: A synthetic epitope of the Anti- Loricrin
      antibodies

<400> SEQUENCE: 59

Gly Val Cys Ile Cys His Gln Thr Gln Gln Lys
1               5                   10

<210> SEQ ID NO 60
<211> LENGTH: 4
<212> TYPE: PRT
<213> ORGANISM: Artificial Sequence
<220> FEATURE:
<223> OTHER INFORMATION: A synthetic core epitope of the Anti- Loricrin
      antibodies

<400> SEQUENCE: 60

Val Lys Tyr Ser
1
```

```
<210> SEQ ID NO 61
<211> LENGTH: 3
<212> TYPE: PRT
<213> ORGANISM: Artificial Sequence
<220> FEATURE:
<223> OTHER INFORMATION: A synthetic core epitope of the Anti- Loricrin
      antibodies

<400> SEQUENCE: 61

Cys Phe Ser
1
```